(12) United States Patent
Seidah et al.

(10) Patent No.: US 8,338,568 B2
(45) Date of Patent: Dec. 25, 2012

(54) CHIMERIC PCSK9 PROTEINS, CELLS COMPRISING SAME, AND ASSAYS USING SAME

(75) Inventors: Nabil G. Seidah, Ile des Soeurs (CA); Jean Davignon, Montreal (CA); Genevieve Dubuc, Longueuil (CA); Lise Bernier, Montreal (CA); Michel Tremblay, Mascouche (CA)

(73) Assignee: Adaerata, Limited Partnership, Montreal (CA)

( * ) Notice: Subject to any disclaimer, the term of this patent is extended or adjusted under 35 U.S.C. 154(b) by 0 days.

(21) Appl. No.: 13/460,029

(22) Filed: Apr. 30, 2012

(65) Prior Publication Data

US 2012/0237945 A1    Sep. 20, 2012

Related U.S. Application Data

(62) Division of application No. 12/300,148, filed as application No. PCT/CA2007/000794 on May 8, 2007, now Pat. No. 8,187,833.

(60) Provisional application No. 60/746,692, filed on May 8, 2006.

(51) Int. Cl.
  *C07K 14/435* (2006.01)
(52) U.S. Cl. ........................ 530/350; 435/226
(58) Field of Classification Search ............ None
  See application file for complete search history.

(56) References Cited

U.S. PATENT DOCUMENTS

| 6,025,155 A | 2/2000 | Hadlaczky |
| 6,077,677 A | 6/2000 | Hodgson |
| 6,204,023 B1 | 3/2001 | Robinson |
| 2002/0160970 A1 | 10/2002 | Hadlaczky |
| 2003/0083293 A1 | 5/2003 | Hadlaczky |
| 2004/0248177 A1 | 12/2004 | Abifadel |

FOREIGN PATENT DOCUMENTS

| EP | 1471152 A1 | 10/2004 |
| WO | WO/2004/097047 A1 | 11/2004 |
| WO | WO/2007/030937 | 3/2007 |
| WO | PCT/CA2007/000794 | 11/2008 |

OTHER PUBLICATIONS

EP Search report 07719719, Feb. 11, 2009, Adaerata Limited Part.
Abifadel et al., "Mutations in PCSK9 cause autosomal dominant hypercholesterolemia", (2003), Nat. Genet. 34:154-156.
Allard et al., "Novel mutations of the PCSK9 gene cause variable phenotype of autosomal dominant hypercholesterolemia", (2005), Hum. Mutat. 26:497.
Anderson et al., "Inhibition of HIV-1 gp160-dependent membrane fusion by a furin-directed alpha 1-antitrypsin variant", (1993), J. Biol. Chem. 268, No. 33: 24887-24891.
Attie A.D., 2004. "The mystery of PCSK9" (2004) Arterioscler. Thromb. Vasc. Biol., 24: 1337-1339.
Attie et al., "Dual regulation of the LDL receptor—some clarity and new questions", (2005), Cell Metab. 1:290-292.

(Continued)

*Primary Examiner* — Nashaat Nashed
(74) *Attorney, Agent, or Firm* — Goudreau Gage Dubuc; Julie Gauvreau

(57) ABSTRACT

A chimera protein comprising in the following order: a signal peptide, a proprotein convertase subtilisin/kexin type 9 preproprotein (PCSK9) sequence consisting of amino acid residues at positions 35 to 696 of SEQ ID NO: 38, a transmembrane domain and a cytosolic domain, wherein said cytosolic (CT) domain comprises a sequence able to recycle the protein from the cellular membrane to endosomes.

1 Claim, 26 Drawing Sheets

OTHER PUBLICATIONS

Bagshaw et al., "A proteomic analysis of lysosomal integral membrane proteins reveals the diverse composition of the organelle", (2005), Mol. Cell Proteomics 4:133-143.

Belkhiri et al., "A noninvasive cell-based assay for monitoring proteolytic activity within a specific subcellular compartment", (2002), Anal. Biochem. 306:237-246.

Benjannet et al., "Post-translational processing of beta-secretase (beta-amyloid-converting enzyme) and its ectodomain . . . ", (2001), J. Biol. Chem. 276, No. 14:10879-10887.

Benjannet et al., "NARC-1/PCSK9 and its natural mutants: zymogen cleavage and effects on the low density lipoprotein . . . ", (2004), J. Biol. Chem. 279, No. 47: 48865-48875.

Benjannet et al., "Alpha1-antitrypsin Portland inhibits processing of precursors mediated by proprotein convertases . . . " (1997), J. Biol. Chem. 272, No. 42: 26210-26218.

Benjannet et al., "The Proprotein Convertase (PC) PCSK9 is Inactivated by Furin and or PC5/6A . . . " (2006), J. Biol. Chem., vol. 281, No. 41:30561-30572.

Berge et al., " Missense Mutations in the PCSK9 Gene Are Associated With Hypocholesterolemia and Possibly . . . " (2006), Arterioscler. Thromb. Vasc. Biol. vol. 26: 1094-1100.

Bergeron et al., "Implication of proprotein convertases in the processing and spread of severe acute respiratory . . . ", (2005) Biochim. Biophys. Res. Commun. 326: 554-563.

Boycott et al., "Homozygous deletion of the very low density lipoprotein receptor gene causes autosomal recessive cerebellar . . . ", (2005), Am. J. Hum. Genet. 77: 477-483.

Cayman Chemicals PCSK9 human antibody # 10007185, Material Safety Data Sheet, Apr. 16, 2006.

Cheng et al., "Secreted site-1 protease cleaves peptides corresponding to luminal loop of sterol regulatory . . . ", (1999), J. Biol. Chem. 274, vol. 32: 22805-22812.

Choo et al., "SPdb—a signal peptide database", (2005), BMC Bioinformatics vol. 6: 249.

Cohen et al., "Low LDL cholesterol in individuals of African descent resulting from frequent nonsense mutations in PCSK9", (2005), Nat. Genet. 37:161-165.

Conesa et al., "Down-regulation of alphav/beta3 integrin via misrouting to lysosomes by overexpression of a beta3Lamp1 fusion protein", (2003), Biochem. J. 370:703-711.

Decroly et al., "Identification of the paired basic convertases implicated in HIV gp160 processing based . . . ", (1996), J Biol. Chem. 271:30442-30450.

Dubuc et al., "Statins upregulate PCSK9, the gene encoding the proprotein convertase neural . . . " (2004), Arterioscler. Thromb. Vasc. Biol. 24:1454-1459.

Essalmani et al., "Deletion of the gene encoding proprotein convertase 5/6 causes early embryonic lethality in the mouse" (2006), Mol. Cell Biol. 26:354-361.

Fasano et al., "A novel loss of function mutation of PCSK9 gene in white subjects with low-plasma . . . ", (2007), Arterioscler Thromb Vasc Biol. 27:677-681.

Fatemi S.H., "Reelin glycoprotein in autism and schizophrenia", (2005), Int. Rev. Neurobiol. 71:179-187.

Goudriaan et al., "Protection from obesity in mice lacking the VLDL receptor", (2001), Arterioscler Thromb Vasc Biol. vol. 21:1488-1493.

Henrich et al., "The crystal structure of the proprotein processing proteinase furin explains its stringent specificity", (2003), Nat. Struct. Biol. 10:520-526.

Hofmann et al., "TMBASE—A database of membrane spanning protein segments", (1993), Biol. Chem. Hoppe-Seyler 374, 166.

Horton et al., "Combined analysis of oligonucleotide microarray data from transgenic and knockout mice . . . ", (2003) Proc. Natl. Acad. Sci. U. S. A 100:12027-12032.

Jadot et al., "Characterization of the signal for rapid internalization of the bovine mannose 6-phosphate/insulin-like . . . ", (1992), J Biol. Chem. 267 No. 16:11069-11077.

Jin et al., "Proprotein covertases are responsible for proteolysis and inactivation of endothelial lipase", (2005), J Biol. Chem. 280:36551-36559.

Kohler et al., "Continuous cultures of fused cells secreting antibody of predefined specificity", (1975), Nature, vol. 256: 495-497.

Kotowski et al.,"A Spectrum of PCSK9 Alleles Contributes to Plasma Levels of Low-Density Lipoprotein Cholesterol", (2006), Am. J. Hum. Genet. 78:410-422.

Laird et al., "BACE1, a major determinant of selective vulnerability of the brain to amyloid-beta amyloidogenesis . . . ", (2005), J Neurosci. 25:11693-11709.

Lalanne et al., "Wild-type PCSK9 inhibits LDL clearance but does not affect apoB-containing lipoprotein production in mouse and . . . ", (2005), J. Lipid Res. 46:1312-1319.

Leren T.P. , "Mutations in the PCSK9 gene in Norwegian subjects with autosomal dominant hypercholesterolemia", (2004), Clin. Genet. 65:419-422.

Lindenbaum et al., "A mammalian artificial chromosome engineering system (ACE System) applicable to . . . " (2004), Nucleic Acids Research vol. 32 (21):e172.

Maxwell et al., "Adenoviral-mediated expression of Pcsk9 in mice results in a low-density lipoprotein . . . ", (2004), Proc. Natl. Acad. Sci. U. S. A 101: 7100-7105.

Maxwell et al., "Overexpression of PCSK9 accelerates the degradation of the LDLR in a post-endoplasmic . . . ", (2005), Proc. Natl. Acad. Sci. U. S. A 102: 2069-2074.

Maxwell et al., " Novel putative SREBP and LXR target genes identified by microarray analysis in liver of cholesterol-fed mice", (2003), J. Lipid Res. 44: 2109-2119.

Naoumova et al., "Severe hypercholesterolemia in four British families with the D374Y mutation in the PCSK9 gene . . . ", (2005), Arterioscler. Thromb. Vasc. Biol. 25:2654-2660.

Naureckiene et al., "Functional characterization of Narc 1, a novel proteinase related to proteinase K", (2003), Arch. Biochem. Biophys. 420: 55-67.

Nour et al., "Structure-Function Analysis of the Prosegment of the Proprotein Convertase PC5A", (2003), J. Biol. Chem. 278, No. 5: 2886-2895.

Nour et al., "The Cysteine-rich Domain of the Secreted Proprotein Convertases PC5A and PACE4 Functions as a Cell Surface . . . ", (2005), Mol. Biol. Cell 16: 5215-5226.

Park et al., Post-transcriptional regulation of low density lipoprotein receptor protein by proprotein convertase . . . , (2004), J. Biol. Chem. 279, No. 48: 50630-50638.

Pisciotta et al., "Additive effect of mutations in LDLR and PCSK9 genes on the phenotype of familial . . . ", (2006), Atherosclerosis 186: 433-440.

Pullikotil et al., "Development of protein-based inhibitors of the proprotein of convertase SKI-1/S1P: processing of SREBP-2 . . . ", (2004), J. Biol. Chem. 279:17338-17347.

Rashid et al., "Decreased plasma cholesterol and hypersensitivity to statins in mice lacking Pcsk9", (2005), Proc. Natl. Acad. Sci. U. S. A 102: 5374-5379.

Seidah et al., "The secretory proprotein convertase neural apoptosis-regulated convertase 1 . . . " (2003), Proc. Natl. Acad. Sci. U. S. A 100: 928-933.

Seidah et al., "Proprotein and prohormone convertases: a family of subtilases generating diverse bioactive polypeptides", (1999), Brain Res. 848: 45-62.

Seidah et al., "The proprotein convertases and their implication in sterol and/or lipid metabolism" (2006), Biological Chemistry,vol. 387: 871-877.

Seidah et al., "Mammalian subtilisin/kexin isozyme SKI-1: A widely expressed proprotein convertase . . . " (1999), Proc. Natl. Acad. Sci. U. S. A 96: 1321-1326.

Seidah et al., "Precursor convertases in the secretory pathway, cytosol and extracellular milieu", (2002), Essays Biochem. 38: 79-94.

Thomas G., "Furin at the cutting edge: from protein traffic to embryogenesis and disease", (2002), Nat. Rev. Mol. Cell Biol. 3: 753-766.

Timms et al., "A mutation in PCSK9 causing autosomal-dominant hypercholesterolemia in a Utah pedigree", (2004), Hum. Genet. 114: 349-353.

Vincent et al., "Chloroquine is a potent inhibitor of SARS coronavirus infection and spread", (2005), Virol. J 2: 69.

Wang et al., "Polymorphism in maternal LRP8 gene is associated with fetal growth", (2006), Am. J. Hum. Genet. 78: 770-777.

Zhao et al., Molecular characterization of loss-of-function mutations in PCSK9 . . . (2006), Am J Hum Genet. 79: 514-23.

Zhong et al., "The prosegments of furin and PC7 as potent inhibitors of proprotein convertases . . . ", (1999), J. Biol. Chem. 274: 33913-33920.

Donoghue et al., A novel Angiotensin-Converting Enzyme-Related Carboxypeptidase . . . , (2000), Circulation Research, vol. 87, No. 5: e1-e9.

Lambert et al., "PCSK9: a promising therapeutic target for dyslipidemias?", (2006), Trends in Endocrinology and Metabolism, vol. 17, No. 3: 79-81.

Maxwell et al., "Proprotein convertase subtilisin kexin 9: the third locus implicated in autosomal . . . ", Current Opinion in Lipidology, (2005) 16(2): 167-172.

Poirier et al., (2008), The Proprotein Convertase PCSK9 Induces the Degradation of Low Density Lipoprotein Receptor . . . , J. Biol. Chem., vol. 283, No. 4: 2363-2372.

Fig. 6

Possible inactivation of PCSK9 by Furin-like convertases

| Substrate | P8 | P6 | P4 | P2 | P1 | P1' | P4' |
|---|---|---|---|---|---|---|---|
| (h,m,r,xl) PCSK9 | E–D | G–T | R–F | H–R | ↓Q–A | S–K |
| (zf) PCSK9 | E–D | G–T | R–V | H–R | ↓Q–A | S–Q |
| (ck) PCSK9 | E–D | S–S | R–F | H–R | ↓Q–A | S–K |
| (tn) PCSK9 | V–G | E–A | G–G | H–R | ↓E–A | S–R |
| (fr) PCSK9 | V–E | K–G | G–G | H–R | ↓E–A | S–R |
| (h) (F216L) PCSK9 | E–D | G–T | R–L–H–R | ↓Q–A | S–K |
| (h) (R218S) PCSK9 | E–D | G–T | R–F | H–S | –Q–A | S–K |

216  
218

Human PCSK9 TM-CT ACE2

```
ATGGGCACCGTCAGCTCCAGGCGGTCCTGGTGGCCGCTGCCACTGCTGCTGCTGCTGCTGCTCCTGGGTCCC
GCGGGCGCCCGTGCGCAGGAGGACGAGGACGGCGACTACGAGGAGCTGGTGCTAGCCTTGCGTTCCGAGGAGGAC
GGCCTGGCCGAAGCACCCGAGCACGGAACCACAGCCACCTTCCACCGCTGCGCCAAGGATCCGTGGAGGTTGCCT
GGCACCTACGTGGTGGTGCTGAAGGAGGAGACCCACCTCTCGCAGTCAGAGCGCACTGCCCGCCGCCTGCAGGCC
CAGGCTGCCCGCCGGGGATACCTCACCAAGATCCTGCATGTCTTCCATGGCCTTCTTCCTGGCTTCCTGGTGAAG
ATGAGTGGCGACCTGCTGGAGCTGGCCTTGAAGTTGCCCCATGTCGACTACATCGAGGAGGACTCCTCTGTCTTT
GCCCAGAGCATCCCGTGGAACCTGGAGCGGATTACCCCTCCACGGTACCGGGCGGATGAATACCAGCCCCCCGAC
GGAGGCAGCCTGGTGGAGGTGTATCTCCTAGACACCAGCATACAGAGTGACCACCGGGAAATCGAGGGCAGGGTC
ATGGTCACCGACTTCGAGAATGTGCCCGAGGAGGACGGGACCCGCTTCCACAGACAGGCCAGCAAGTGTGACAGT
CATGGCACCCACCTGGCAGGGGTGGTCAGCGGCCGGGATGCCGGCGTGGCCAAGGGTGCCAGCATGCGCAGCCTG
CGCGTGCTCAACTGCCAAGGGAAGGGCACGGTTAGCGGCACCCTCATAGGCCTGGAGTTTATTCGGAAAAGCCAG
CTGGTCCAGCCTGTGGGGCCACTGGTGGTGCTGCTGCCCCTGGCGGGTGGGTACAGCCGCGTCCTCAACGCCGCC
TGCCAGCGCCTGGCGAGGGCTGGGGTCGTGCTGGTCACCGCTGCCGGCAACTTCCGAGACGATGCCTGCCTCTAC
TCCCCAGCCTCAGCTCCCGAGGTCATCACAGTTGGGGCCACCAATGCCCAGGACCAGCCGGTGACCCTGGGGACT
TTGGGGACCAACTTTGGCCGCTGTGTGGACCTCTTTGCCCCAGGGGAGGACATCATTGGTGCCTCCAGCGACTGC
AGCACCTGCTTTGTGTCACAGAGTGGGACATCACAGGCTGCTGCCCACGTGGCTGGCATTGCAGCCATGATGCTG
TCTGCCGAGCCGGAGCTCACCCTGGCCGAGTTGAGGCAGAGACTGATCCACTTCTCTGCCAAAGATGTCATCAAT
GAGGCCTGGTTCCCTGAGGACCAGCGGGTACTGACCCCCAACCTGGTGGCCGCCCTGCCCCCCAGCACCCATGGG
GCAGGTTGGCAGCTGTTTTGCAGGACTGTGTGGTCAGCACACTCGGGGCCTACACGGATGGCCACAGCCATCGCC
CGCTGCGCCCCAGATGAGGAGCTGCTGAGCTGCTCCAGTTTCTCCAGGAGTGGGAAGCGGCGGGGCGAGCGCATG
GAGGCCCAAGGGGGCAAGCTGGTCTGCCGGGCCCACAACGCTTTTGGGGGTGAGGGTGTCTACGCCATTGCCAGG
TGCTGCCTGCTACCCCAGGCCAACTGCAGCGTCCACACAGCTCCACCAGCTGAGGCCAGCATGGGGACCCGTGTC
CACTGCCACCAACAGGGCCACGTCCTCACAGGCTGCAGCTCCCACTGGGAGGTGGAGGACCTTGGCACCCACAAG
CCGCCTGTGCTGAGGCCACGAGGTCAGCCCAACCAGTGCGTGGGCCACAGGGAGGCCAGCATCCACGCTTCCTGC
TGCCATGCCCCAGGTCTGGAATGCAAAGTCAAGGAGCATGGAATCCCGGCCCCTCAGGAGCAGGTGACCGTGGCC
TGCGAGGAGGGCTGGACCCTGACTGGCTGCAGTGCCCTCCCTGGGACCTCCACGTCCTGGGGGCCTACGCCGTA
GACAACACGTGTGTAGTCAGGAGCCGGGACGTCAGCACTACAGGCAGCACCAGCGAAGAGGCCGTGACAGCCGTT
GCCATCTGCTGCCGGAGCCGGCACCTGGCGCAGGCCTCCCAGGAGCTCCAGACCGGTAAGCCTATCCCTAACCCT
CTCCTCGGTCTCGATTCTACGGGAGGAATATGGCTGATTGTTTTTGGAGTTGTGATGGGAGTGATAGTGGTTGGC
ATTGTCATCCTGATCTTCACTGGGATCAGAGATCGGAAGAAGAAAAATAAAGCAAGAAGTGGAGAAAATCCTTAT
GCCTCCATCGATATTAGCAAAGGAGAAAATAATCCAGGATTCCAAAACACTGATGATGTTCAGACCTCCTTTTAG
```

```
MGTVSSRRSWWPLPLLLLLLLLGPAGARAQEDEDGDYEELVLALRSEEDGLAEAPEHGTTATFHRCAKDPWRLP
GTYVVVLKEETHLSQSERTARRLQAQAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRVMVTDFENVPEEDGTRFHRQASKCDS
HGTHLAGVVSGRDAGVAKGASMRSLRVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGTLGTNFGRCVDLFAPGEDIIGASSDC
STCFVSQSGTSQAAAHVAGIAAMMLSAEPELTLAELRQRLIHFSAKDVINEAWFPEDQRVLTPNLVAALPPSTHG
AGWQLFCRTVWSAHSGPTRMATAIARCAPDEELLSCSSFSRSGKRRGERMEAQGGKLVCRAHNAFGGEVYAIAR
CCLLPQANCSVHTAPPAEASMGTRVHCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAVDNTCVVRSRDVSTTGSTSEEAVTAV
AICCRSRHLAQASQELQTGKPIPNPLLGLDSTGGIWLIVFGVVMGVIVVGIVILIFTGIRDRKKKNKARSGENPY
ASIDISKGENNPGFQNTDDVQTSF
```

Figure 16

Human PCSK9 TM-CT Lamp1

ATGGGCACCGTCAGCTCCAGGCGGTCCTGGTGGCCGCTGCCACTGCTGCTGCTGCTGCTGCTGCTCCTGGGTCCC
GCGGGCGCCCGTGCGCAGGAGGACGAGGACGGCGACTACGAGGAGCTGGTGCTAGCCTTGCGTTCCGAGGAGGAC
GGCCTGGCCGAAGCACCCGAGCACGGAACCACAGCCACCTTCCACCGCTGCGCCAAGGATCCGTGGAGGTTGCCT
GGCACCTACGTGGTGGTGCTGAAGGAGGAGACCCACCTCTCGCAGTCAGAGCGCACTGCCCGCCGCCTGCAGGCC
CAGGCTGCCCGCCGGGGATACCTCACCAAGATCCTGCATGTCTTCCATGGCCTTCTTCCTGGCTTCCTGGTGAAG
ATGAGTGGCGACCTGCTGGAGCTGGCCTTGAAGTTGCCCCATGTCGACTACATCGAGGAGGACTCCTCTGTCTTT
GCCCAGAGCATCCCGTGGAACCTGGAGCGGATTACCCCTCCACGGTACCGGGCGGATGAATACCAGCCCCCCGAC
GGAGGCAGCCTGGTGGAGGTGTATCTCCTAGACACCAGCATACAGAGTGACCACCGGGAAATCGAGGGCAGGGTC
ATGGTCACCGACTTCGAGAATGTGCCCGAGGAGGACGGGACCCGCTTCCACAGACAGGCCAGCAAGTGTGACAGT
CATGGCACCCACCTGGCAGGGGTGGTCAGCGGCCGGGATGCCGGCGTGGCCAAGGGTGCCGGCATGCGCAGCCTG
CGCGTGCTCAACTGCCAAGGGAAGGGCACGGTTAGCGGCACCCTCATAGGCCTGGAGTTTATTCGGAAAAGCCAG
CTGGTCCAGCCTGTGGGGCCACTGGTGGTGCTGCTGCCCCTGGCGGGTGGGTACAGCCGCGTCCTCAACGCCGCC
TGCCAGCGCCTGGCGAGGGCTGGGGTCGTGCTGGTCACCGCTGCCGGCAACTTCCGAGACGATGCCTGCCTCTAC
TCCCCAGCCTCAGCTCCCGAGGTCATCACAGTTGGGGCCACCAATGCCCAGGACCAGCCGGTGACCCTGGGGACT
TTGGGGACCAACTTTGGCCGCTGTGTGGACCTCTTTGCCCCAGGGGAGGACATCATTGGTGCCTCCAGCGACTGC
AGCACCTGCTTTGTGTCACAGAGTGGGACATCACAGGCTGCTGCCCACGTGGCTGGCATTGCAGCCATGATGCTG
TCTGCCGAGCGGAGCTCACCCTGGCCGAGTTGAGGCAGAGACTGATCCACTTCTCTGCCAAAGATGTCATCAAT
GAGGCCTGGTTCCCTGAGGACCAGCGGGTACTGACCCCCAACCTGGTGGCCGCCCTGCCCCCCAGCACCCATGGG
GCAGGTTGGCAGCTGTTTTGCAGGACTGTGTGGTCAGCACACTCGGGGCCTACACGGATGGCCACAGCCATCGCC
CGCTGCGCCCCAGATGAGGAGCTGCTGAGCTGCTCCAGTTTCTCCAGGAGTGGGAAGCGGCGGGGCGAGCGCATG
GAGGCCCAAGGGGGCAAGCTGGTCTGCCGGGCCCACAACGCTTTTGGGGGTGAGGGTGTCTACGCCATTGCCAGG
TGCTGCCTGCTACCCCAGGCCAACTGCAGCGTCCACACAGCTCCACCAGCTGAGGCCAGCATGGGGACCCGTGTC
CACTGCCACCAACAGGGCCACGTCCTCACAGGCTGCAGCTCCCACTGGGAGGTGGAGGACCTTGGCACCCACAAG
CCGCCTGTGCTGAGGCCACGAGGTCAGCCCAACCAGTGCGTGGGCCACAGGGAGGCCAGCATCCACGCTTCCTGC
TGCCATGCCCCAGGTCTGGAATGCAAAGTCAAGGAGCATGGAATCCCGGCCCCTCAGGAGCAGGTGACCGTGGCC
TGCGAGGAGGGCTGGACCCTGACTGGCTGCAGTGCCCTCCCTGGGACCTCCCACGTCCTGGGGGCCTACGCCGTA
GACAACACGTGTGTAGTCAGGAGCCGGGACGTCAGCACTACAGGCAGCACCAGCGAAGAGGCCGTGACAGCCGTT
GCCATCTGCTGCCGGAGCCGGCACCTGGCGCAGGCCTCCCAGGAGCTCCAGACCGGTAAGCCTATCCCTAACCCT
CTCCTCGGTCTCGATTCTACGGGAGGACTGATCCCCATCGCTGTGGGTGGTGCCCTGGCGGGGCTGGTCCTCATC
GTCCTCATCGCCTACCTCGTCGGCAGGAAGAGGAGTCACGCAGGCTACCAGACTATCTAG

MGTVSSRRSWWPLPLLLLLLLLLGPAGARAQEDEDGDYEELVLALRSEEDGLAEAPEHGTTATFHRCAKDPWRLP
GTYVVVLKEETHLSQSERTARRLQAQAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRVMVTDFENVPEEDGTRFHRQASKCDS
HGTHLAGVVSGRDAGVAKGAGMRSLRVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGTLGTNFGRCVDLFAPGEDIIGASSDC
STCFVSQSGTSQAAAHVAGIAAMMLSAEPELTLAELRQRLIHFSAKDVINEAWFPEDQRVLTPNLVAALPPSTHG
AGWQLFCRTVWSAHSGPTRMATAIARCAPDEELLSCSSFSRSGKRRGERMEAQGGKLVCRAHNAFGGEGVYAIAR
CCLLPQANCSVHTAPPAEASMGTRVHCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAVDNTCVVRSRDVSTTGSTSEEAVTAV
AICCRSRHLAQASQELQTGKPIPNPLLGLDSTGGLIPIAVGGALAGLVLIVLIAYLVGRKRSHAGYQTI

Figure 17

Human PCSK9 TM-CT LDLR

```
ATGGGCACCGTCAGCTCCAGGCGGTCCTGGTGGCCGCTGCCACTGCTGCTGCTGCTGCTGCTCCTGGGTCCC
GCGGGCGCCCGTGCGCAGGAGGACGAGGACGGCGACTACGAGGAGCTGGTGCTAGCCTTGCGTTCCGAGGAGGAC
GGCCTGGCCGAAGCACCCGAGCACGGAACCACAGCCACCTTCCACCGCTGCGCCAAGGATCCGTGGAGGTTGCCT
GGCACCTACGTGGTGGTGCTGAAGGAGGAGACCCACCTCTCGCAGTCAGAGCGCACTGCCCGCCGCCTGCAGGCC
CAGGCTGCCCGCCGGGGATACCTCACCAAGATCCTGCATGTCTTCCATGGCCTTCTTCCTGGCTTCCTGGTGAAG
ATGAGTGGCGACCTGCTGGAGCTGGCCTTGAAGTTGCCCCATGTCGACTACATCGAGGAGGACTCCTCTGTCTTT
GCCCAGAGCATCCCGTGGAACCTGGAGCGGATTACCCCTCCACGGTACCGGGCGGATGAATACCAGCCCCCCGAC
GGAGGCAGCCTGGTGGAGGTGTATCTCCTAGACACCAGCATACAGAGTGACCACCGGGAAATCGAGGGCAGGGTC
ATGGTCACCGACTTCGAGAATGTGCCCGAGGAGGACGGGACCCGCTTCCACAGACAGGCCAGCAAGTGTGACAGT
CATGGCACCCACCTGGCAGGGGTGGTCAGCGGCCGGGATGCCGGCGTGGCCAAGGGTGCCGGCATGCGCAGCCTG
CGCGTGCTCAACTGCCAAGGGAAGGGCACGGTTAGCGGCACCCTCATAGGCCTGGAGTTTATTCGGAAAAGCCAG
CTGGTCCAGCCTGTGGGGCCACTGGTGGTGCTGCTGCCCCTGGCGGGTGGGTACAGCCGCGTCCTCAACGCCGCC
TGCCAGCGCCTGGCGAGGGCTGGGGTCGTGCTGGTCACCGCTGCCGGCAACTTCCGAGACGATGCCTGCCTCTAC
TCCCCAGCCTCAGCTCCCGAGGTCATCACAGTTGGGGCCACCAATGCCCAGGACCAGCCGGTGACCCTGGGGACT
TTGGGGACCAACTTTGGCCGCTGTGTGGACCTCTTTGCCCCAGGGGAGGACATCATTGGTGCCTCCAGCGACTGC
AGCACCTGCTTTGTGTCACAGAGTGGGACATCACAGGCTGCTGCCCACGTGGCTGGCATTGCAGCCATGATGCTG
TCTGCCGAGCCGGAGCTCACCCTGGCCGAGTTGAGGCAGAGACTGATCCACTTCTCTGCCAAAGATGTCATCAAT
GAGGCCTGGTTCCCTGAGGACCAGCGGGTACTGACCCCCAACCTGGTGGCCGCCCTGCCCCCCAGCACCCATGGG
GCAGGTTGGCAGCTGTTTTGCAGGACTGTGTGGTCAGCACACTCGGGGCCTACACGGATGGCCACAGCCATCGCC
CGCTGCGCCCCAGATGAGGAGCTGCTGAGCTGCTCCAGTTTCTCCAGGAGTGGGAAGCGGCGGGGCGAGCGCATG
GAGGCCCAAGGGGGCAAGCTGGTCTGCCGGGCCCACAACGCTTTTGGGGGTGAGGGTGTCTACGCCATTGCCAGG
TGCTGCCTGCTACCCCAGGCCAACTGCAGCGTCCACACAGCTCCACCAGCTGAGGCCAGCATGGGGACCCGTGTC
CACTGCCACCAACAGGGCCACGTCCTCACAGGCTGCAGCTCCCACTGGGAGGTGGAGGACCTTGGCACCCACAAG
CCGCCTGTGCTGAGGCCACGAGGTCAGCCCAACCAGTGCGTGGGCCACAGGGAGGCCAGCATCCACGCTTCCTGC
TGCCATGCCCCAGGTCTGGAATGCAAAGTCAAGGAGCATGGAATCCCGGCCCCTCAGGAGCAGGTGACCGTGGCC
TGCGAGGAGGGCTGGACCCTGACTGGCTGCAGTGCCCTCCCTGGGACCTCCCACGTCCTGGGGGCCTACGCCGTA
GACAACACGTGTGTAGTCAGGAGCCGGGACGTCAGCACTACAGGCAGCACCAGCGAAGAGGCCGTGACAGCCGTT
GCCATCTGCTGCCGGAGCCGGCACCTGGCGCAGGCCTCCCAGGAGCTCCAGACCGGTAAGCCTATCCCTAACCCT
CTCCTCGGTCTCGATTCTACGGGAGGAGCTCTGTCCATTGTCCTCCCCATCGTGCTCCTCGTCTTCCTTTGCCTG
GGGGTCTTCCTTCTATGGAAGAACTGGCGGCTTAAGAACATCAACAGCATCAACTTTGACAACCCCGTCTATCAG
AAGACCACAGAGGATGAGGTCCACATTTGCCACAACCAGGACGGCTACAGCTACCCCTCGAGACAGATGGTCAGT
CTGGAGGATGACGTGGCGTGA
```

```
MGTVSSRRSWWPLPLLLLLLLLLGPAGARAQEDEDGDYEELVLALRSEEDGLAEAPEHGTTATFHRCAKDPWRLP
GTYVVVLKEETHLSQSERTARRLQAQAARRGYLTKILHVFHGLLPGFLVKMSGDLLELALKLPHVDYIEEDSSVF
AQSIPWNLERITPPRYRADEYQPPDGGSLVEVYLLDTSIQSDHREIEGRVMVTDFENVPEEDGTRFHRQASKCDS
HGTHLAGVVSGRDAGVAKGAGMRSLRVLNCQGKGTVSGTLIGLEFIRKSQLVQPVGPLVVLLPLAGGYSRVLNAA
CQRLARAGVVLVTAAGNFRDDACLYSPASAPEVITVGATNAQDQPVTLGTLGTNFGRCVDLFAPGEDIIGASSDC
STCFVSQSGTSQAAAHVAGIAAMMLSAEPELTLAELRQRLIHFSAKDVINEAWFPEDQRVLTPNLVAALPPSTHG
AGWQLFCRTVWSAHSGPTRMATAIARCAPDEELLSCSSFSRSGKRRGERMEAQGGKLVCRAHNAFGGEGVYAIAR
CCLLPQANCSVHTAPPAEASMGTRVHCHQQGHVLTGCSSHWEVEDLGTHKPPVLRPRGQPNQCVGHREASIHASC
CHAPGLECKVKEHGIPAPQEQVTVACEEGWTLTGCSALPGTSHVLGAYAVDNTCVVRSRDVSTTGSTEEAVTAV
AICCRSRHLAQASQELQTGKPIPNPLLGLDSTGGALSIVLPIVLLVFLCLGVFLLWKNWRLKNINSINFDNPVYQ
KTTEDEVHICHNQDGYSYPRQMVSLEDDVA
```

Figure 18

1. Pro-protein PCSK9 (with signal peptide) 1-692

MGTVSSRRSWWPLPLLLLLLLLLGPAGARAQEDEDGDYEELVLALRSEEDGLAEAPEHGTTATFHRCAKD
PWRLPGTYVVVLKEETHLSQSERTARRLQAQAARRGYLTKILHVFHGLLPGFLVKMSGDLLELALKLPHV
DYIEEDSSVFAQ*SIPWNLERITPPRYRADEYQPPDGGSLVEVYLLDTSIQSDHREIEGRVMVTDFENVPE*
*EDGTRFHR*QASKCDSHGTHLAGVVSGRDAGVAKGASMRSLRVLNCQGKGTVSGTLIGLEFIRKSQLVQPV
GPLVVLLPLAGGYSRVLNAACQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMMLSAEPELTLAELRQRLIHFSA
KDVINEAWFPEDQRVLTPNLVAALPPSTHGAGWQLFCRTVWSAHSGPTRMATAVARCAPDEELLSCSSFS
RSGKRRGERMEAQGGKLVCRAHNAFGGEGVYAIARCCLLPQANCSVHTAPPAEASMGTRVHCHQQGHVLT
GCSSHWEVEDLGTHKPPVLRPRGQPNQCVGHREASIHASCCHAPGLECKVKEHGIPAPQEQVTVACEEGW
TLTGCSALPGTSHVLGAYAVDNTCVVRSRDVSTTGSTSEGAVTAVAICCRSRHLAQASQELQ

2. Pro-protein PCSK9 (without signal peptide) 31-692

QEDEDGDYEELVLALRSEEDGLAEAPEHGTTATFHRCAKD
PWRLPGTYVVVLKEETHLSQSERTARRLQAQAARRGYLTKILHVFHGLLPGFLVKMSGDLLELALKLPHV
DYIEEDSSVFAQ*SIPWNLERITPPRYRADEYQPPDGGSLVEVYLLDTSIQSDHREIEGRVMVTDFENVPE*
*EDGTRFHR*QASKCDSHGTHLAGVVSGRDAGVAKGASMRSLRVLNCQGKGTVSGTLIGLEFIRKSQLVQPV
GPLVVLLPLAGGYSRVLNAACQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMMLSAEPELTLAELRQRLIHFSA
KDVINEAWFPEDQRVLTPNLVAALPPSTHGAGWQLFCRTVWSAHSGPTRMATAVARCAPDEELLSCSSFS
RSGKRRGERMEAQGGKLVCRAHNAFGGEGVYAIARCCLLPQANCSVHTAPPAEASMGTRVHCHQQGHVLT
GCSSHWEVEDLGTHKPPVLRPRGQPNQCVGHREASIHASCCHAPGLECKVKEHGIPAPQEQVTVACEEGW
TLTGCSALPGTSHVLGAYAVDNTCVVRSRDVSTTGSTSEGAVTAVAICCRSRHLAQASQELQ

3. PSCK9 amino acids 153 to 692 (active full-length form i.e. without signal peptide and prosegment)

*SIPWNLERITPPRYRADEYQPPDGGSLVEVYLLDTSIQSDHREIEGRVMVTDFENVPE*
*EDGTRFHR*QASKCDSHGTHLAGVVSGRDAGVAKGASMRSLRVLNCQGKGTVSGTLIGLEFIRKSQLVQPV
GPLVVLLPLAGGYSRVLNAACQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMMLSAEPELTLAELRQRLIHFSA
KDVINEAWFPEDQRVLTPNLVAALPPSTHGAGWQLFCRTVWSAHSGPTRMATAVARCAPDEELLSCSSFS
RSGKRRGERMEAQGGKLVCRAHNAFGGEGVYAIARCCLLPQANCSVHTAPPAEASMGTRVHCHQQGHVLT
GCSSHWEVEDLGTHKPPVLRPRGQPNQCVGHREASIHASCCHAPGLECKVKEHGIPAPQEQVTVACEEGW
TLTGCSALPGTSHVLGAYAVDNTCVVRSRDVSTTGSTSEGAVTAVAICCRSRHLAQASQELQ

4. PSCK9 amino acids 153 to 218 (N-terminal fragment produced by furin/PC5 cleavage)

*SIPWNLERITPPRYRADEYQPPDGGSLVEVYLLDTSIQSDHREIEGRVMVTDFENVPE*
*EDGTRFHR*

Figure 19

5. PSCK9 amino acids 219 to 692 (PCSK9-ΔN$_{218}$ : furin/PC5-cleaved form)

QASKCDSHGTHLAGVVSGRDAGVAKGASMRSLRVLNCQGKGTVSGTLIGLEFIRKSQLVQPV
GPLVVLLPLAGGYSRVLNAACQRLARAGVVLVTAAGNFRDDACLYSPASAPEVITVGATNAQDQPVTLGT
LGTNFGRCVDLFAPGEDIIGASSDCSTCFVSQSGTSQAAAHVAGIAAMMLSAEPELTAELRQRLIHFSA
KDVINEAWFPEDQRVLTPNLVAALPPSTHGAGWQLFCRTVWSAHSGPTRMATAVARCAPDEELLSCSSFS
RSGKRRGERMEAQGGKLVCRAHNAFGGEGVYAIARCCLLPQANCSVHTAPPAEASMGTRVHCHQQGHVLT
GCSSHWEVEDLGTHKPPVLRPRGQPNQCVGHREASIHASCCHAPGLECKVKEHGIPAPQEQVTVACEEGW
TLTGCSALPGTSHVLGAYAVDNTCVVRSRDVSTTGSTSEGAVTAVAICCRSRHLAQASQELQ

Figure 19 (continued)

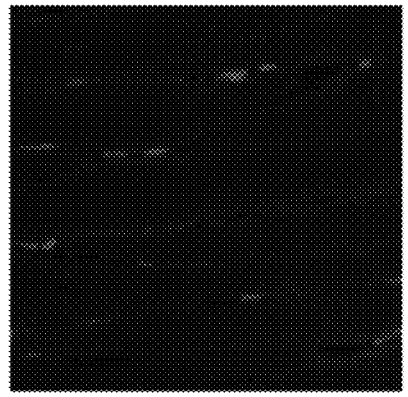
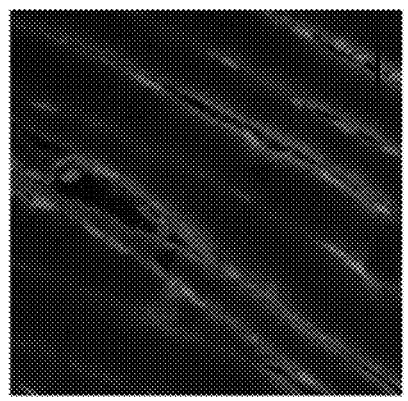
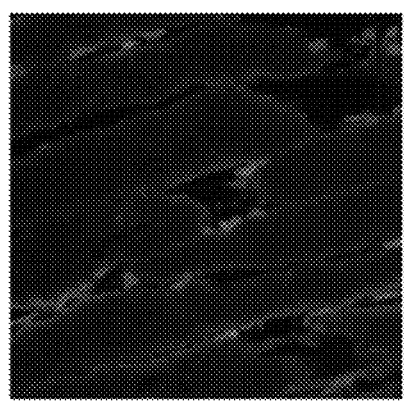
Fig. 21

CLUSTAL W (1.83) multiple sequence alignment

```
mouse        MGTHCSAWLRWPLLPLLPPLLLLLLLLCPTGAGAQ-DEDGDYEELMLALPSQEDGLADEA 59
rat          MGIRCSTWLRWPLS----PQLLLLLLLCPTGSRAQ-DEDGDYEELMLALPSQEDSLVDEA 55
human        MGTVSSRRSWWPLP----LLLLLLLLLGPAGARAQEDEDGDYEELVLALRSEEDGLAEAP 56
monkey       MGTVSSRRSWWPLP----LLLLLLLLLGPAGARAQEDEDGDYEELVLALRSEEDGLAEAP 56
              **  .*   ***       ******  *:*:   **   *********:***  *:**.*.:  .
consensus    MGXXXSXXXXWPLPXXXXXXXLLLLLLLXPXGXXAQXDEDGDYEELXLALXSXEDXLXXXX 60 mouse        AHVATATFRRCSKEAWRLPGTYIVVLMEETQRLQIEQTAHRLQTRAARRGYVIKVLHIFY
119
rat          SHVATATFRRCSKEAWRLPGTYVVVLMEETQRLQVEQTAHRLQTWAARRGYVIKVLHVFY
115
human        EHGTTATFHRCAKDPWRLPGTYVVVLKEETHLSQSERTARRLQAQAARRGYLTKILHVFH
116
monkey       EHGTTATFHRCAKDPWRLPGTYVVVLKEETHLSQSERTARRLQAQAARRGYLTKILHVFH
116
              *  :****:**:*:.:.********:*** ***:    *  *:**:***:  ******:  *:**:*:
consensus    XHXXTATFXRCXKXXWRLPGTYXVVLXEETXXXQXEXTAXRLQXXAARRGYXXKXLHXFX
120 mouse        DLFPGFLVKMSSDLLGLALKLPHVEYIEEDSFVFAQSIPWNLERIIPAWHQTEEDRSPDG
179
rat          DLFPGFLVKMSSDLLGLALKLPHVEYIEEDSLVFAQSIPWNLERIIPAWQQTEEDSSPDG
175
human        GLLPGFLVKMSGDLLELALKLPHVDYIEEDSSVFAQSIPWNLERITPPRYRADEYQPPDG
176
monkey       GLLPGFLVKMSGDLLELALKLPHVDYIEEDSSVFAQSIPWNLERITPPRYRADEYQPPDG
176
              .*:********.***  ********:****** ************* *.   :::*   .***
consensus    XLXPGFLVKMSXDLLXLALKLPHVXYIEEDSXVFAQSIPWNLERIXPXXXXXXXEXXXPDG
180 mouse        SSQVEVYLLDTSIQGAHREIEGRVTITDFNSVPEEDGTRFHRQASKCDSHGTHLAGVVSG
239
rat          SSQVEVYLLDTSIQSGHREIEGRVTITDFNSVPEEDGTRFHRQASKCDSHGTHLAGVVSG
235
human        GSLVEVYLLDTSIQSDHREIEGRVMVTDFENVPEEDGTRFHRQASKCDSHGTHLAGVVSG
236
monkey       GSLVEVYLLDTSIQSDHREIEGRVMVTDFENVPEEDGTRFHRQASKCDSHGTHLAGVVSG
236
              .*  **********.  ******* :***:.*****************************
consensus    XSXVEVYLLDTSIQXXHREIEGRVXXTDFXXVPEEDGTRFHRQASKCDSHGTHLAGVVSG
240 mouse        RDAGVAKGTSLHSLRVLNCQGKGTVSGTLIGLEFIRKSQLIQPSGPLVVLLPLAGGYSRI
299
rat          RDAGVAKGTSLHSLRVLNCQGKGTVSGTLIGLEFIRKSQLIQPSGPLVVLLPLAGGYSRI
295
human        RDAGVAKGASMRSLRVLNCQGKGTVSGTLIGLEFIRKSQLVQPVGPLVVLLPLAGGYSRV
296
```

FIG. 22

| | |
|---|---|
| monkey 296 | RDAGVAKGASMRSLRVLNCQGKGTVSGTLIGLEFIRKSQLVQPVGPLVVLLPLAGGYSRV |
| | \*\*\*\*\*\*\*\*:\*::\*\*\*\*\*\*\*\*\*\*\*\*\*\*\*\*\*\*\*\*\*\*\*\*\*:\*\* \*\*\*\*\*\*\*\*\*\*\*\*\*\*: |
| consensus 300 | RDAGVAKGXSXXSLRVLNCQGKGTVSGTLIGLEFIRKSQLXQPXGPLVVLLPLAGGYSRX |

| | |
|---|---|
| mouse 359 | LNAACRHLARTGVVLVAAAGNFRDDACLYSPASAPEVITVGATNAQDQPVTLGTLGTNFG |
| rat 355 | LNTACQRLARTGVVLVAAAGNFRDDACLYSPASAPEVITVGATNAQDQPVTLGTLGTNFG |
| human 356 | LNAACQRLARAGVVLVTAAGNFRDDACLYSPASAPEVITVGATNAQDQPVTLGTLGTNFG |
| monkey 356 | LNAACQRLARAGVVLVTAAGNFRDDACLYSPASAPEVITVGATNAQDQPVTLGTLGTNFG |
| | \*\*:\*\*::\*\*\*:\*\*\*\*\*:\*\*\*\*\*\*\*\*\*\*\*\*\*\*\*\*\*\*\*\*\*\*\*\*\*\*\*\*\*\*\*\*\*\*\*\*\*\*\*\*\* |
| consensus 360 | LNXACXXLARXGVVLVXAAGNFRDDACLYSPASAPEVITVGATNAQDQPVTLGTLGTNFG |

FIG.22 (continued)

```
mouse     RCVDLFAPGKDIIGASSDCSTCFMSQSGTSQAAAHVAGIVARMLSREPTLTLAELRQRLI
419
rat       RCVDLFAPGKDIIGASSDCSTCYMSQSGTSQAAAHVAGIVAMMLNRDPALTLAELRQRLI
415
human     RCVDLFAPGEDIIGASSDCSTCFVSQSGTSQAAAHVAGIAAMMLSAEPELTLAELRQRLI
416
monkey    RCVDLFAPGEDIIGASSDCSTCFVSQSGTSQAAAHVAGIAAMMLSAEPELTLAELRQRLI
416
          ********:*************::***************.* **. :* **********
consensus RCVDLFAPGXDIIGASSDCSTCXXSQSGTSQAAAHVAGIXAMMLXXXPXLTLAELRQRLI
420 mouse     HFSTKDVINMAWFPEDQQVLTPNLVATLPPSTHETGGQLLCRTVWSAHSGPTRTATATAR
479
rat       LFSTKDVINMAWFPEDQRVLTPNRVATLPPSTQETGGQLLCRTVWSAHSGPTRTATATAR
475
human     HFSAKDVINEAWFPEDQRVLTPNLVAALPPSTHGAGWQLFCRTVWSAHSGPTRMATAVAR
476
monkey    HFSAKDVINEAWFPEDQRVLTPNLVAALPPSTHGAGWQLFCRTVWSAHSGPTRMATAVAR
476
          **:***** ******:***** **:*****: :* **:************ ***.**
consensus XFSXKDVINXAWFPEDQXVLTPNXVAXLPPSTXXXGXQLXCRTVWSAHSGPTRXATAXAR
480 mouse     CAPEEELLSCSSFSRSGRRRGDWIEAIGGQQVCKALNAFGGEGVYAVARCCLVPRANCSI
539
rat       CAPEEELLSCSSFSRSGRRRGDRIEAIGGQQVCKALNAFGGEGVYAVARCCLLPRVNCSI
535
human     CAPDEELLSCSSFSRSGKRRGERMEAQGGKLVCRAHNAFGGEGVYAIARCCLLPQANCSV
536
monkey    CAPDEELLSCSSFSRSGKRRGERMEAQGGKLVCRAHNAFGGEGVYAIARCCLLPQANCSI
536
          ***:*************:***: :** **: **:* **********:*****:*****.***:
consensus CAPXEELLSCSSFSRSGXRRGXXXEAXGGXXVCXAXNAFGGEGVYAXARCCLXPXXNCSX
540 mouse     HNTPAARAGLETHVHCHQKDHVLTGCSFHWEVEDLSVRRQPALRSRRQPGQCVGHQAASV
599
rat       HNTPAARAGPQTPVHCHQKDHVLTGCSFHWEVENLRAQQQPLLRSRHQPGQCVGHQEASV
595
human     HTAPPAEASMGTRVHCHQQGHVLTGCSSHWEVEDLGTHKPPVLRPRGQPNQCVGHREASI
596
monkey    HTAPPAEAGMGTRVHCHQQGHVLTGCSSHWEVEDLGTHKPPMLRPRGQPNQCVGHREASI
596
          *.:*.*.*.   * *****:.****** ******:*  .:: *  **.* **.*****: **:
consensus HXXPXAXAXXXTXVHCHQXXHVLTGCSXHWEVEXLXXXXXPXLRXRXQPXQCVGHXXASX
600 mouse     YASCCHAPGLECKIKEHGISGPSEQVTVACEAGWTLTGCNVLPGASLTLGAYSVDNLCVA
659
rat       HASCCHAPGLECKIKEHGIAGPAEQVTVACEAGWTLTGCNVLPGASLPLGAYSVDNVCVA
655
human     HASCCHAPGLECKVKEHGIPAPQEQVTVACEEGWTLTGCSALPGTSHVLGAYAVDNTCVV
656
```

FIG.22 (continued)

```
monkey      HASCCRAPGLECKVKEHGIPAPQEQVTVACEEGWTLTGCSALPGTSHVLGAYAVDNTCVV
656
            :****:*******:*****..* ******** *******..***:*  ****:*** **.
consensus   XASCCXAPGLECKXKEHGIXXPXEQVTVACEXGWTLTGCXXLPGXSXXLGAYXVDNXCVX
660 mouse       RVHDTARADRTSGEATVAAAICCRSRPSAKASWVQ-  694
rat         RIRDAGRADRTSEEATVAAAICCRSRPSAKASWVHQ  691
human       RSRDVSTTGSTSEGAVTAVAICCRSRHLAQASQELQ  692
monkey      RSRDVSTAGSTSEEAVAAVAICCRSRHLAQASQELQ  692
            * :*.. :. **  *..*.******  *:**
consensus   RXXDXXXXXTSXXAXXAXAICCRSRXXAXASXXXX  696
```

CHIMERIC PCSK9 PROTEINS, CELLS COMPRISING SAME, AND ASSAYS USING SAME

CROSS REFERENCE TO RELATED APPLICATIONS

This application is a divisional application of U.S. patent application Ser. No. 12/300,148 filed on Aug. 5, 2009, now pending, which is a National Entry Application of PCT application No. PCT/CA2007/000794 filed on May 8, 2007 and published in English under PCT Article 21(2), which itself claims benefit of U.S. Provisional Application No. 60/746, 692, filed on May 8, 2006. All documents above are incorporated herein in their entirety by reference.

FIELD OF THE INVENTION

The present invention relates to chimeric proteins, cells comprising same, and assays using same. More specifically, the present invention is concerned with cell-based assays for identifying modulators of proprotein convertase subtilisin/kexin type 9 preproprotein (PCSK9).

REFERENCE TO SEQUENCE LISTING

Pursuant to 37 C.F.R. 1.821(c), a sequence listing is submitted herewith as an ASCII compliant text file named 12810_437—as amended Apr. 27, 2012_ST25.txt, created on Apr. 27, 2012 and having a size of 172 Kb kilobytes. The content of the aforementioned file is hereby incorporated by reference in its entirety.

BACKGROUND OF THE INVENTION

The Regulation of Processing within the Constitutive Secretory Pathway

The Proprotein Convertases (PCs) are responsible for the tissue-specific limited proteolysis of multiple polypeptide precursors, generating a large diversity of bioactive molecules (Seidah and Chretien, 1999; Seidah and Prat, 2002). Many cellular processing events involve an ordered cascade of cleavage events accomplished by one or more convertase(s) belonging to the PCs/SKI-1/PCSK9 mammalian subtilase family (Seidah and Chretien, 1999; Seidah and Prat, 2002; Seidah et al., 2003). This mammalian PC-family comprises nine members: PC1/3, PC2, furin, PC4, PACE4, PC5/6, PC7, SKI-1/S1P and NARC-1/PCSK9 (Seidah and Chretien, 1999; Seidah and Prat, 2002; Seidah et al., 2003). The first seven proteinases are basic amino acid specific PCs cleaving precursor proteins at single or paired basic residues within the motif (K/R)—(X)n-(K/R)↓, in which n=0, 2, 4 or 6 (Seidah and Chretien, 1999). These proteinases are phylogenetically more closely related to each other and to yeast kexin than to SKI-1/S1P or NARC-1/PCSK9, which belong to the pyrolysin (Seidah et al., 1999) and proteinase K (Seidah et al., 2003) subfamilies, respectively. The latter enzymes recognize the motifs R—X-(hydrophobic/aliphatic)-Z↓ (Seidah et al., 2006) and VFAQ↓ (SEQ ID NO: 116) (Benjannet et al., 2004), respectively. These enzymes have been implicated in a wide variety of functions regulating cellular homeostasis and a number of pathologies including cancer, inflammation, neurodegenerative diseases, atherosclerosis and viral infections. It was recently realized that some of these convertases play critical roles in the regulation of lipids and/or sterols (Seidah et al., 2006) either through the inactivation of lipoprotein lipases e.g., by PC5/6, PACE4 and furin (Jin et al., 2005), activation of specific membrane-bound transcription factors (SREBP-1 and -2) by SKI-1/S1P (Cheng et al., 1999), or by enhancing the degradation of the low density lipoprotein receptor (LDLR) by PCSK9 (Maxwell and Breslow, 2004; Benjannet et al., 2004; Park et al., 2004; Maxwell et al., 2005).

A number of factors regulate the processing of PCs themselves. First, convertases require removal of their inhibitory prosegment for activation (FIG. 1). Analysis of the biosynthesis of furin, PACE4, PC5, PC7, SKI-1, and PCSK9 revealed that they are synthesized as zymogens that undergo autocatalytic cleavage of their N-terminal inhibitory pro-segment, which seems to act both as a chaperone and an intramolecular inhibitor (Zhong et al., 1999; Nour et al., 2003; Seidah et al., 2003). Except for PC2, primary prosegment cleavage is necessary for most convertases to exit from the endoplasmic reticulum (ER). Overexpression of furin, PC5, and PC7 prosegments as independent domains confirmed their inhibitory potency and the presence of critical elements at their C-terminus. The design of two potent and specific-inhibitors of SKI-1 based on variants of either its prosegment or α1-PDX were reported (Pullikotil et al., 2004).

The second control element is the trafficking of these enzymes to different intracellular organelles. Dependant on the cognate substrate, constitutively secreted PCs cleave in the Golgi, trans Golgi network (TGN), endosomes or at the cell surface (FIG. 2). The modified serpin α1-PDX (Benjannet et al., 1997; Anderson et al., 1993) and the PC-prosegments (Zhong et al., 1999) inhibit the PCs within the constitutive secretory pathway.

Regulation and Processing of PCSK9

The regulation of PCSK9 activity could be achieved by various mechanisms, which among others could act at the level of: (i) its transcription where its mRNA levels are upregulated by SREBP-2, and downregulated by cholesterol (Maxwell et al., 2003; Dubuc et al., 2004) via a reduced level of activated nuclear SREBP-2 (Horton et al., 2003; Dubuc et al., 2004); (ii) its translation which may be controlled by specific factors; (iii) its post-translational modifications including its zymogen cleavage and/or activation, glycosylation, sulfation (Seidah et al., 2003; Benjannet et al., 2004), or possibly by other processing events resulting in its degradation (Seidah et al., 2003); (iv) its cellular localization and/or sorting of mature PCSK9; (v) its level of secretion; and possibly, (vi) its subsequent cellular re-uptake.

PCSK9/NARC-1 plays a role in cholesterol homeostasis. Indeed, point mutations in the PCSK9 gene within its coding exons (Attie, 2004) are associated with either familial hypercholesterolemia (Abifadel et al., 2003; Leren, 2004; Timms et al., 2004; Allard et al., 2005; Naoumova et al., 2005) or hypocholesterolemia (Cohen et al., 2005; Kotowski et al., 2006; Berge et al., 2006) phenotypes. This led to the classification of the PCSK9 gene as the third chromosomal locus associated with autosomal dominant familial hypercholesterolemia, with the LDLR and Apolipoprotein B (Apo B) comprising the other two loci (Abifadel et al., 2003). It is thus plausible that some of the single point mutations of PCSK9 associated with autosomal dominant familial dyslipidemias could enhance or abrogate one or more of the PCSK9 regulatory events (Attie and Seidah, 2005).

It should be noted that PCSK9 is mostly expressed in adult liver hepatocytes and in small intestinal enterocytes (Seidah et al., 2003). Its exact role in these tissues is still unknown, except that this convertase possibly enhances the rate of degradation of the endogenous hepatic and possibly intestinal LDLR. Although no PCSK9 inhibitor is yet known, potent PCSK9 siRNAs were identified that upregulate the LDLR (Benjannet et al., 2004). The lowering of the level of LDLR at the cell surface is thus a good indicator of the PCSK9 activity.
Natural Mutants of PCSK9 and Implication in Hypocholesterolemia It was suggested that some PCSK9 single point mutations result in a gain or enhanced function of PCSK9 on the degradation of LDLR in acidic compartments, possibly endosomes (Benjannet et al., 2004; Maxwell et al., 2005), while others would cause a loss of function (Cohen et al., 2005), and would be associated with the development of hyper- or hypocholesterolemia, respectively (Attie and Seidah, 2005; Kotowski et al., 2006). It was thus hypothesized that high levels of active PCSK9 are associated with a faster rate of degradation of the cell surface LDLR, resulting in increased amounts of circulating LDL-cholesterol, as the uptake of the latter in liver hepatocytes by the LDLR will be diminished accordingly, and vice versa. This would suggest that the level of cell surface LDLR is indirectly proportional to the level of hepatic and likely intestinal active PCSK9. This hypothesis is reinforced by the in vivo observations that in mice lacking a functional PCSK9 gene (PCSK9-knockout mice), the level of hepatocyte cell surface LDLR is greatly enhanced resulting in an ~50% drop in the level of circulating LDL-cholesterol (Rashid et al., 2005), whereas mice overexpressing PCSK9 result in higher levels of circulating LDL-cholesterol (Benjannet et al., 2004; Park et al., 2004; Maxwell and Breslow, 2004; Lalanne et al., 2005).

Examples of hypercholesterolemic-associated mutations include the Ser127-to-Arg (S127R) amino acid change. The S127R mutation is located between the primary and putative secondary zymogen processing sites of the PCSK9 propeptide; mutations in the catalytic subunit include Phe216-to-Leu (F216L), which is located close to the active site at His226 (Abifadel et al., 2003) and Arg218-to-Ser (R218S) (Allard et al., 2005). These and other new natural mutations reported in Table 1 below were biochemically analyzed and some of them were suggested to result in a gain of function, likely including a gain of proteolytic activity or a better co-localization with LDLR (Benjannet et al., 2004). However, the molecular mechanisms that underlie the dominance of the dyslipidemia trait caused by PCSK9 missense mutations is still unclear.
Regulation of Other Cell Surface Receptors by PCSK9

Only the LDLR was reported to be affected by PCSK9. The LDLR is part of the 7-member LDL receptor superfamily that included amongst others, very low density lipoprotein receptor (VLDLR) (Official Symbol: VLDLR and Entry gene ID: 7436, NCBI), apolipoprotein e receptor 2 (ApoER2) (Official Symbol: LRP8 and Entry gene ID: 7804, NCBI) and LRP (FIGS. 11 and 12). LRP, a member of the 7-member LDL receptor superfamily that includes amongst others, LDLR, very low density lipoprotein receptor (VLDLR) (Official Symbol: VLDLR and Entry gene ID: 7436, NCBI), apolipoprotein e receptor 2 (ApoER2) (Official Symbol: LRP8 and Entry gene ID: 7804, NCBI) (FIGS. 11 and 12), was found not to be affected by PCSK9 (Benjannet et al., 2004). There is a need to develop a cell system that would allow the identification of novel PCSK9 targets.
Implication of PCSK9 in Human Pathologies PCSK9 has clearly been involved in the regulation of LDL-cholesterol. Dyslipidemia is in fact the first dominant human pathology directly associated with mutations in a PC, namely in PCSK9. Since PCSK9 is also expressed in brain and gut (Seidah et al., 2003), it is plausible that mutations in PCSK9 may have other consequences aside from LDL-cholesterol regulation. Such pleiotropic effects were reported for other convertases. An example includes the β-secretase BACE1, which has been clearly implicated in Alzheimer's disease, but whose functions seems also to include memory and emotion regulation independent of its effect on the processing of β-amyloid precursor (Laird et al., 2005).

A definition of novel functions of PCSK9 would alert to potential mechanism-based side effects that may occur with PCSK9 inhibitors designed to decrease LDL-cholesterol levels. Thus, a sensitive assay for PCSK9 function is urgently needed, which may uncover new unsuspected functions of this enzyme.
In Vitro PCSK9 Assays Most of the in vitro assays designed for identifying proteinase inhibitors consist in the addition of the compound to a reaction mixture containing a purified enzyme and its substrate, and measuring the absence or reduction of the cleavage products observed when the mixture is incubated under similar conditions but without the inhibitory compound. However, since none of the existing methods allowed for the detection of an active enzymatic form of PCSK9, no such in vitro assays are yet available using PCSK9 for identifying PCSK9 inhibitors. Furthermore, some inhibitors active in vitro may not find utility in vivo because of their inability to enter the cell and reach the cellular compartments where PCSK9 is localized. There is thus a need for the development of cell-based assays specific for PCSK9 activities.
PCSK9 Cell-Based Assays Prior art cell-based assays for identifying convertase-inhibitory compounds produce false positives. For instance, Oh et al. 2004 described a cell-based assay for β-secretase activity using a target chimeric protein substrate containing three domains: an amino-terminal TM domain, a beta-site and an alkaline phosphatase (AP). In this assay, the activity of BACE on the chimera results in the release of AP in the culture medium. An inhibition of the BACE activity results in the absence of AP release in the culture medium. An absence of AP in the culture medium could result not only from the inhibition of the target substrate synthesis itself, but also from a variety of irrelevant cellular mechanisms including amongst others, the absence of target chimeric protein substrate expression itself, modification of chaperones, cellular trafficking, protein folding or even a pH change within the cells, etc. It is thus difficult to determine through their use whether the absence of detection of a specific signal resulted from enzyme inactivation or from another irrelevant reason.

Although a positive cell-based assay which targets cathepsin L in the lysosome and used for the identification of protease inhibitors was described (Belkhiri et al., 2002), this assay is not appropriate for the identification of PCSK9 inhibitors. Other positive cell-based assays measuring the increase of a signal molecule at the cell surface do not offer the appropriate sensitivity for screening due to the high background of the signal molecule already present at the cell surface. For instance, the measurement of re-appearance of LDLR at the surface of cells overexpressing wild type PCSK9 does not provide a sensitive positive screening for PCSK9 inhibitory compounds due to the LDLR background that still remains at the cell surface (Benjannet et al., 2004).

There is thus a need for an improved positive cell-based assay adapted to PCSK9.

The present invention seeks to meet these and other needs.

The present description refers to a number of documents, the content of which is herein incorporated by reference in their entirety.

SUMMARY OF THE INVENTION

Five classes of proteinases are known, including the Serine (Ser), Aspartic (Asp), Metallo, Cysteine (Cys) and Threonine (Thr) proteinases, estimated to contain a total of 500-600 members in the human and mouse genomes. Different proteinases digest their substrates within different specific cell compartments or extracellularly. For instance, the proteinases present in the proteasome (Asp, Ser and Thr proteinases) are active throughout the cytoplasm and the nucleus, caspases (Cys proteinases) are active in the cytoplasm, still other proteinases are active in the secretory and/or endocytic pathways.

The secretory and endocytic pathways of eukaryotic organelles consist of multiple compartments. Specific transport mechanisms are required to direct molecules to defined locations. The localization of proteins to specific membranes is complex and involves multiple interactions. All of the proteins that pass through the Golgi apparatus, except those that are retained there as permanent residents, are sorted in the trans Golgi network (TGN) according to their intended final destination. The terminology "secretory and endocytic pathways" is a generic term covering various pathways including that of proteins sorted to lysosomes (e.g. cathepsin B), the pathway of proteins recycled into earlier secretory compartments by recognition of a retention signal (e.g. KDEL (SEQ ID NO: 1) for the endoplasmic reticulum), the regulatory pathway and the constitutive secretory pathway.

The constitutive secretory pathway, is one by which proteins are secreted from the cells at a rate that is mostly limited by their rate of synthesis (FIG. 2). These proteins follow a pathway that goes through the endoplasmic reticulum (ER), the Golgi, the TGN and finally through the cell surface. Some of the constitutively secreted proteins however could once at the cell surface be re-internalized via early endosomes and then directed towards either 1) the TGN once again, 2) lysosomes; or even 3) be recycled to the cell surface for another round of sorting. This trafficking is intimately associated with sorting motifs found within the cytoplasmic tail of these usually membrane-bound proteins. PCs including Furin, PC5A, PC5B, PC7, PACE4, subtilisin-kexin isoenzyme SKI-1 and PCSK9 are mostly sorted through the constitutive secretory pathway.

Depending on the cognate substrate, constitutively secreted PCs may cleave them in the Golgi, the TGN, the endosomes, the cell surface or a combination of these locations. PCSK9 seems to enhance the degradation of the LDLR within acidic compartments, likely to be clathrin coated endosomes (Benjannet et al., 2004; Maxwell et al., 2005).

The present invention provides in a first aspect a cell-based assay for monitoring a PCSK9 activity and modulators thereof. In specific embodiments of the assay, the cell line harbors a very low to undetectable level of different cell surfaces molecules (herein referred as "detectors") the absence of which depends upon PCSK9 activity. The presence of PCSK9 inhibitors are detected by the reappearance of one or more detectors. The assay can be adapted to detect, in parallel or not, the presence of different cell surface detectors.

In certain embodiments, the cell-based assays of the present invention provide an increased level of sensitivity. In certain embodiments, the cell-based assays of the present invention provide fewer false positives. In certain embodiments, the cell-based assays of the present invention allow the detection of one or several independent detectors the presence of which is dependent on the PCSK9 regulatory pathway. In certain embodiments, the cell-based assays of the present invention provide not only identify compounds that are inhibitory to the catalytic activity of PCSK9 but also identify inhibitors other steps of the PCSK9 pathway, including upstream PCSK9 regulators.

The present invention relates to chimeras comprising an amino acid primary structure containing, from the N- to C-terminal amino acid sequence: 1) the PCSK9 sequence (either wild type, mutated form, or a combination thereof) or fragments thereof having an activity on the level of LDLR at the cell surface; followed by 2) a transmembrane domain (TM) for membrane anchoring which prevents the secretion of PCSK9; and 3) a cytoplasmic also referred to as "cytosolic" (CT) signal that allows the chimera, once it reaches the plasma membrane to be recycled through early endosomes. FIG. 3 schematically presents various forms of PCSK9 chimeras of the present invention.

The chimera containing a TM-CT (e.g. the TM-CT of ACE2, Lamp1 or LDLR) that includes one or more Y—X—X-hydrophobic motifs (Jadot et al., 1992) (e.g. the Y-A-S—I sequence (SEQ ID NO: 2) present in the CT of ACE2) are sorted from the cellular membrane towards endosomes/lysosomes. Such TM-CT-containing chimera are desirable for convertases that process their substrates in endosomes/acidic compartments such as PCSK9. Measurement of a LDLR decrease at the cell surface is a good indication that the PCSK9-chimera harbor characteristics appropriate for the present invention (FIG. 4).

The sequence of PCSK9 in the chimera could contain the wild type sequence or alternatively variants of PCSK9 identified as conferring to PCSK9 resistance to cleavage by other enzymes, thereby resulting in an increased PCSK9 activity. In this respect, the applicants obtained direct evidence that indeed the level of mature PCSK9 is under the control of proteolysis by one or more members of the basic-amino acid specific convertases including furin and PC5 (FIGS. 5 to 7).

Indeed, the Applicants observed that the secreted wild type PCSK9 could be found as an active full length protein (N1) or alternatively as a N-terminally ~8 kDa-truncated form (N2) (FIG. 5). Interestingly, this N2 form was either not observed or significantly decreased in experiments using the French mutants R218S and F216L, respectively (FIG. 5). This suggested that the presence of Arg218 may be critical for the production of the N2 form.

Sequence alignment of a variety of vertebrate PCSK9s showed a conservation of Arg218 which, in most cases, is found within a R—X—X—R (SEQ ID NO: 3) motif (FIG. 6) typical of a basic amino acid specific PC-recognition motif that is recognized by Furin/PC5-like enzymes (Seidah and Chretien, 1999). The mutation R218S completely disrupts this motif whereas the F216L affects the P3 position (FIG. 6, bottom).

Co-expression of the wild type PCSK9 with convertases as well as with β-secretase revealed that only the membrane-bound Furin form and, to a lesser extent, the PC5A are able to process the N1 form of PCSK9 into the N2 form, with the concomitant loss of the co-immunoprecipitated PCSK9 pro-segment (FIG. 7). The N2 form thus represents PCSK9 truncated of the first 218 amino acid sequence and is herein after referred as PCSK9-$\Delta N_{218}$. In addition, co-expression of the serpin α1-PDX completely abolishes the processing of PCSK9 into the truncated form (FIG. 7).

In agreement with these data, Furin is unable to process the R218S mutant and only partially processes the F216L mutant compared to wild type PCSK9 (FIG. 8). This led the Applicants to produce a PCSK9 molecule that can be more extensively processed at $Arg_{218}$ by the endogenous Furin, namely by replacing the wild type $RFHR_{218}\downarrow QA$ sequence (SEQ ID NO: 4) by an optimal Furin-recognition sequence $RRRR^{218}\downarrow EL$ (SEQ ID NO: 5), with the motifs $RFHR_{218}\downarrow EA$ (SEQ ID NO: 6) and $RFHR_{218}\downarrow EL$ (SEQ ID NO: 7) giving intermediate Furin-cleavability (FIG. 9).

Notice the absence of prosegment co-immunoprecipitating with the PCSK9-$\Delta N_{218}$ form produced with the RRRR$_{218}\downarrow$EL (SEQ ID NO: 5) sequence (FIG. 9), which would be predicted since such cleavage would remove the active site Asp$_{186}$.

Analysis of the activity of wild type PCSK9, of three mutants R218S, RRRR$_{218}$EL (SEQ ID NO: 5), H226A and of a truncated form of PCSK9 that included the Cys/His-rich domain of PCSK9 (CHRD) revealed that only the wild type and the R218S PCSK9 are active in enhancing the degradation of the LDLR (FIG. 10). Thus, PCSK9-$\Delta N_{218}$ is an inactive form of PCSK9 that is secreted from cells. In comparison, the active site mutant His229 which results in the zymogen propCSK9 remains in the ER (Benjannet et al., 2004). These forms provide ideal controls for the activity of PCSK9 in the secretory pathway, differentiating inhibitors that affect the protease activity of PCSK9 from those affecting other cellular processes.

The cleavage of PCSK9 by Furin and/or PC5A may provide a rationale behind the hypercholesterolemia phenotype associated with the French (F216L and R218S) mutations and hypocholesterolemia phenotype in Black African Americans associated with L253F mutation (Abifadel et al., 2003; Allard et al., 2005). Thus, PCSK9 processing by other PCs is a novel mechanism regulating the level of the active form of the enzyme, and may represent a general mechanism behind other mutations resulting in either hypercholesterolemia (loss of cleavage) or hypocholesterolemia (gain of cleavage). Table 1 below presents examples of such PCSK9 mutations (Abifadel et al., 2003; Allard et al., 2005; Pisciotta et al., 2005; Kotowski et al., 2006). This does not exclude the possibility that other mechanisms may be responsible for the phenotypes behind other mutations, such as cellular sorting, post-translational modifications and zymogen activation, etc.

The present invention provides cell-based tools useful for the identification of novel PCSK9 target cell surface receptors that could be used, in addition to the LDLR, as detector molecules in the cell-based screening assays. The fact that LDLR is part of the 7-member LDL receptor superfamily that included amongst others VLDLR, ApoER2 and LRP (FIG. 11) led the Applicants to test the hypothesis that PCSK9 may affect one or more of these LDLR-related proteins. While LRP was found not to be affected by PCSK9 (Benjannet et al., 2004), the two closely related LDLR-related proteins, VLDLR and ApoER2 (FIG. 12), were degraded in the presence of PCSK9 (FIG. 13). The expression of the [PCSK9-TM-CT] chimera of the present invention was found to be much more potent in enhancing the degradation of all three receptors, independently of the cell type tested (FIGS. 13 and 14).

VLDLR and/or ApoER2 have been implicated in a variety of diseases including schizophrenia and autism which implicates Reelin, the common ligand of both receptors (Fatemi, 2005), fetal growth restriction (Wang, 2006 for ApoER2), obesity (Goudriaan, 2001 for VLDLR), and the recessive form of non-progressive cerebellar ataxia found in the Hutterite population (Boycott, 2005 for VLDLR). PCSK9 could thus have implication in such VLDLR and ApoER2-associated diseases and identify PCSK9 as a novel potential therapeutic target in such VLDLR and ApoER2-associated diseases.

The methods of classifying or stratifying the subjects of the present invention into subgroups having different phenotypes enables a better characterization of PCSK9-associated diseases and eventually a better selection of treatment depending on the subgroup to which the subject belongs.

The present invention provides powerful tools for the design of potent cell-based assays that incorporate PCSK9 and/or any of its variants alone or in combination with chimeras (FIGS. 3 and 15).

Transgenic expression of PCSK9 in mouse liver resulted in a line that expresses >40 fold more PCSK9 than the endogenous enzyme in hepatocytes. The transgenic protein was tagged with a V5 at its C-terminus to differentiate it from the endogenous one. Analysis of mouse plasma samples revealed that PCSK9-V5 was secreted in blood and partially processed by Furin-like enzymes to generate PCSK9-$\Delta N_{218}$ as observed in cells and in human plasma. Interestingly, analysis of VLDLR levels in the muscle of these mice versus non-transgenic control littermates revealed that the level of VLDLR was decreased at least 3-fold in muscle. This is the first evidence that circulating PCSK9 can enhance the degradation of VLDLR in vivo and at distant sites away from those of its synthesis.

The present invention allows the identification of novel PCSK9-associated pathways and identifies PCSK9 as a potential target in these pathways-associated diseases.

The present invention provides cell-based assays that incorporate PCSK9 associated with an increased activity (FIG. 15).

The present invention provides cell-based assays that incorporate PCSK9 associated with an increased activity, and which may also incorporate chimera specifically cleaved by PCSK9 (FIG. 15) such as that described in co-pending application no. WO 2007/030937 filed Sep. 14, 2006.

The cell-based assays of the present invention advantageously mimic the environment in which inhibitors will have to work in vivo (i.e. using endogenous proteinases and selecting for cell-diffusible inhibitors effective in the secretory pathway). In specific embodiments, they are advantageously positive assays (i.e., selects for re-appearance of a signal molecule on the cell surface).

Cell-based assays according to specific embodiments of the present invention incorporate the use of multiple detector molecules providing to the assays a high level of sensitivity and specificity.

The assays of the present invention are able to discriminate compounds that are toxic to cells.

The present invention provides for the detection of specific PCSK9 activity through the use of one or multiple types of cell surface receptors/detector molecules.

The cell-based assays of the present invention allow for high throughput screening (HTS) of candidate compounds. Identification of PCSK9 with Enhanced Activities: PCSK9 Chimeric TM-CT Protein Proteins destined for location in the membrane contain a transmembrane domain comprising a stretch of 15 to 22 hydrophobic amino acids in an alpha helical secondary conformation. Several transmembrane domains are described and could be used in the present invention. TMbase™ is a database of transmembrane proteins (Hofmann K. et al. 1993) with their helical membrane-spanning (TM) domain. Without being so limited, they include that derived from the human angiotensin converting enzyme-2 (ACE2 i.e. the SARS-Corona Virus receptor), Lamp-1 and LDLR. The addition of a TM domain to the PCSK9 sequence prevents the secretion of the chimera into the extracellular medium.

Signals present within the cytoplasmic tail (CT) of several proteins determine whether or not it will be sorted through a particular secretory pathway. For example, signals determining TGN targeting of furin include amino acids of the cytoplasmic tail. Indeed, two independent targeting signals, which consist of the acidic peptide CPSDSEEDEG$_{783}$ (SEQ ID NO: 8) and the tetrapeptide YKGL$_{765}$ (SEQ ID NO: 9) (an example of Y—X—X-hydrophobic motif) were previously identified that control the recycling of the constitutively secreted Furin back from the cell surface to the TGN (Thomas, 2002). The YKGL (SEQ ID NO: 9) is a determinant for targeting from the cell surface to the endosomes, while the acidic peptide signal in the cytoplasmic tail is necessary and sufficient to localize the reporter molecule from the endosomes to the TGN. The chimera protein of the present invention combines signals present on the PCSK9 with those of a cytoplasmic tail that allow the chimera to be secreted via constitutive secretory pathway and be recycled in endosomes. The choice of a cytoplasmic tail signal relies on the ability of the protein to reach the cell surface and be recycled in endosomes. For this purpose a variety of CT in combination with different TM could be utilized such as the TM-CT from LDLR as this is one of the proteins targeted for enhanced degradation by PCSK9. Other members of the LDLR superfamily (FIG. 11), including those susceptible to PCSK9 (e.g. VLDLR and ApoER2) could also be used. However, this approach is not limited to TM-CTs of proteins that are targets of PCSK9-enhanced degradation and others TM-CTs could also be used including that of the SARS coronavirus receptor the angiotensin converting enzyme-2 (ACE2) (Bergeron et al., 2005; Vincent et al., 2005) or the lysosomal proteins such as LAMP-1 (Conesa et al., 2003) (FIG. 3).

N-Terminal Signal Sequence

Proteins destined for export, for location in a membrane and more generally for the secretory pathway contain a signal peptide comprising the first 20 or so amino acids at the N-terminal end and always includes a substantial number of hydrophobic amino acids. Several peptide signals are known and could be used in the present invention. For instance, SPdb, a signal peptide database lists a number of useful signal peptides (Choo et al. 2005). Without being so limited, useful signal peptides include those of human insulin, renin as well as those of PCs themselves amongst others.

Furin/PC5-Resistant and Sensitive PCSK9 Variants

The present invention demonstrates that the wild type PCSK9 sequence contains basic amino acid specific proprotein convertase cleavage motifs which could regulate the PCSK9 activities. PCSK9 variants described herein use specific naturally occurring (F216L and R218S mutants) or artificially modified (e.g. RRRR$^{218}$↓EL (SEQ ID NO: 5)) wild type furin/PC5 cleavage motifs, however the present invention is not limited to any of them. Any modification of the basic amino acid specific proprotein convertase cleavage motifs decreasing (e.g. F216L and R218S) or increasing (e.g. RRRR$^{218}$↓EL (SEQ ID NO: 5)) the cleavability of PCSK9 by furin, or PC5 can be used. However, this does not exclude the possibility that other mutations may hinder or enhance the cleavability of PCSK9 by other proprotein convertases.

Host Cells

Although the assays described herein use specific host cells, the present invention is not limited to any of them. Any cells, preferably human cells expressing the chimeric PCSK9 that is to be screened for modulators can be used. The use of human cells is preferred for selecting a modulator effective in human. Hence, any cells expressing a detector molecule could be used, including HuH7, HepG2, HEK293, LoVo-05 etc. . . .

The cell line would preferably express chimeric and/or variants of PCSK9 and present a very low to undetectable level of LDLR at the cell surface. The cells could either be used as transiently transfected cells or as stably selected clones or pools. The HuH7 cell line appears to be one of the best human cell lines to perform the assay as these cells are of hepatic origin, express endogenously PCSK9 and LDLR, and overexpression of PCSK9 in these cells causes the degradation of the LDLR. However any cell expressing LDLR and PCSK9 or an appropriate mutant thereof (e.g. PCSK9-R218S) could be used in specific embodiments of the present invention including stable HepG2. One of the advantages of using HepG2 cells is the absence of PC5 expression in these cells (Essalmani et al., 2006), although the present invention also suggests the use of a chimera resistant to PC5 (e.g. the R218S-PCSK9-[TM-CT]). In some specific assays, for instances in cases where host cells do not express PCSK9, purified recombinant PCSK9 proteins could also be added directly into the cell culture supernatant.

Cells Expressing a PCSK9 with Increased Intracellular Activities: Identification of Novel Detector Molecules Clones of cells of the present invention express a PCSK9 with increased cellular activities either due to the addition of an appropriate TM-CT, or due to mutations conferring to PCSK9 resistance to inactivation by other convertases (e.g. PC5 and furin), or due to any combination of these features. Preferably, these cells harbor a very low to undetectable level of LDLR at the cell surface.

These cells could be used to identify novel cell surface molecules that, similarly to LDLR, are also sensitive to the presence of the PCSK9. Cells expressing a PCSK9 with increased intracellular activities are well suited for proteomics and/or genomics studies aimed at defining the pathways affected by PCSK9. Genomics and proteomics analyses may compare cells overexpressing a super active PCSK9 to cells expressing any inactive PCSK9 variant (e.g. RRRREL-TM-CT chimera). Examples of proteomic analyses include the characterization by FACS analysis (Vincent et al., 2005) and/or Mass spectrometry (MS/MS) of the proteins that are missing at the cell surface (e.g., VLDLR and ApoER2) or endosomes/lysosomes in cells expressing super active PCSK9 (Bagshaw et al., 2005).

These novel identified cell surface molecules sensitive to PCSK9 could then be further used as detector molecules in cell-based assays. These novel detector molecules could be used either from endogenous expression or from stably or transiently transfected expressing cells.

These novel cell surface PCSK9-sensitive molecules identify PCSK9 as well as the PCSK9 pathway as novel target(s) in the treatment or prevention of their related human disease. For example amongst others, VLDLR and ApoER2 have been implicated in schizophrenia and autism because of their binding to Reelin (Fatemi, 2005), PCSK9 could also have implication in VLDLR and ApoER2-associated diseases.

Cells Expressing a PCSK9 with Increased Cellular Activities: Cell-Based Screening Assays Clones of cells of the present invention express a PCSK9 with increased cellular activities either due to the addition of an appropriate TM-CT, or due to mutations conferring to PCSK9 resistance to inactivation by other convertases (e.g. PC5, furin), or due to any combination of these features. These cells harbor a very low to undetectable level of one or a combination of detector molecules at the cell surface (~10% or less of the level measured with a control cell expressing an inactive PCSK9, e.g., RRRREL (SEQ ID NO: 5)—PCSK9) (e.g. LDLR (FIG. 10), VLDLR, ApoER2). These cells are perfectly adapted to the screening of PCSK9 inhibitory compounds.

PCSK9-[TM-CT of Lamp1] is a more powerful chimera to enhance the degradation of the LDLR, as compared to PCSK9-[TM-CT of ACE2] and PCSK9-[TM-CT of LDLR] (FIG. 4), although all three are much more effective than the wild type (WT) PCSK9. Accordingly, without being so limited, any one of them could be used in cell-based assays to screen for PCSK9 modulating molecules including PCSK9 inhibitors.

Detector Molecules at the Surface of Cells: Selection of Inhibitory Compounds

In the presence of compounds that inhibit the PCSK9 activities, detector molecules will reappear at the cell surface. Inhibition of the functional activity of PCSK9 implies that the compound is able to enter the cell and reach the endosomes or other compartments. This does not exclude however that some compounds may alternatively inhibit a PCSK9 activity at the cell surface or outside the cell. In any cases, such a positive selection procedure ensures that the screening identifies only compounds that are not toxic to cells.

The compounds could modify a step of the PCSK9 pathway, including the activity of an upstream regulator (e.g. by increasing the activity of furin on PCSK9 degradation). The compounds could also inhibit the catalytic site of the enzyme or other allosteric sites that impact on the productive catalytic activity or functions of the convertase. These compounds can then be tested in vitro to better define their exact mechanism of action.

However, it is also conceivable that some compounds will act in cellular compartments that control the folding and/or trafficking of the convertase, e.g., in the ER. It is less likely that the cell-based assays of the present invention will select such non specific PCSK9 inhibitors because they are likely to affect other proteins and likely lead to cellular stress and death. Such compounds would less likely be picked up by the cell-based assays of the present invention.

Although the assays described herein use specific detection tools, the present invention should not be so limited. Any method measuring specifically the presence of a detector molecule, or variant thereof should work. This includes measuring one or several detector molecules including LDLR, VLDLR, ApoER2 or any other detector molecule sensitive to the action of PCSK9. For instance, using specific monoclonal antibodies, either commercially available or produced using the detector molecule sequence, the level of each detector molecule could be estimated by antibodies labelled with a variety of light emitting systems, e.g., fluorochromes or chemiluminescent probes.

DEFINITION

As used herein the terms "proteinase" refers to an enzyme that breaks down proteins into their component peptides.

As used herein the terms 'PCSK9 activity' refers to detectable enzymatic, biochemical or cellular activity attributable to PCSK9. Without being so limited, such activities include the effect of PCSK9 on reducing the level of LDLR (or VLDLR or ApoER2) at the cell surface, and/or the PCSK9 proteinase activity itself.

As used herein the terms "PCSK9-associated disease or condition" refer to diseases or conditions resulting in part from a defective PCSK9 activity and diseases resulting in part from a defective activity of a PCSK9 target such as LDLR, VLDLR or ApoER2. Similarly, as used herein the terms "LDLR-associated disease or condition", VLDLR-associated disease or condition" and "ApoER2-associated disease or condition" refer to diseases resulting in part from a defective LDLR activity, a defective VLDLR activity or a defective ApoER2 activity, respectively. For instance, as defined herein, hypercholesterolemia is an LDLR-associated condition while fetal growth restriction is a ApoER2-associated disease and the recessive form of non-progressive cerebellar ataxia found in the Hutterite population is a VLDLR-associated disease. Without being so limited, PCSK9-associated diseases or conditions include cardiovascular diseases such as hypercholesterolemia, atherosclerosis, stroke and ischemia; schizophrenia, autism; fetal growth restriction; obesity; and a recessive form of non-progressive cerebellar ataxia.

As used herein, the term "modulator" refers to a compound that increases or decreases the PCKS9 activity. It includes proteins, peptides and small molecules.

As used herein, the term "PCSK9 inhibitor" includes any compound able to directly or indirectly reduce the transcription, translation, or activity of PCSK9. It includes intracellular as well as extracellular PCSK9 inhibitors. Without being so limited, such inhibitors include siRNA, antisense molecules, proteins, peptides, small molecules, antibodies, etc.

As used herein the term "subject" is meant to refer to any mammal including human, mice, rat, dog, cat, pig, cow, monkey, horse, etc. In a particular embodiment, it refers to a human.

As used herein the terminology "biological sample" refers to any solid or liquid sample isolated from a living being. In a particular embodiment, it refers to any solid or liquid sample isolated from a human. Without being so limited it includes a biopsy material, blood, saliva, synovial fluid, urine, amniotic fluid and cerebrospinal fluid.

As used herein the terminology "blood sample" is meant to refer to blood, plasma or serum.

As used herein the terminology "control blood sample" is meant to refer to a blood sample of a subject known not to suffer from the PCSK9-associated disease under scrutiny in the assay. In specific embodiments, it is the sample of a subject not to suffer from a PCSK9-associated disease. In particular embodiments where dyslipidemia is under scrutiny, it thus refers to a subject known not to suffer from dyslipidemia.

As used herein the term "purified" in the expression "purified polypeptide" means altered "by the hand of man" from its natural state (i.e. if it occurs in nature, it has been changed or removed from its original environment) or it has been synthesized in a non-natural environment (e.g., artificially synthesized). These terms do not require absolute purity (such as a homogeneous preparation) but instead represents an indication that it is relatively more pure than in the natural environment. For example, a protein/peptide naturally present in a living organism is not "purified", but the same protein separated (about 90-95% pure at least) from the coexisting materials of its natural state is "purified" as this term is employed herein.

Similarly, as used herein, the term "purified" in the expression "purified antibody" is simply meant to distinguish man-made antibody from an antibody that may naturally be produced by an animal against its own antigens. Hence, raw serum and hybridoma culture medium containing anti-PCSK9-$\Delta N_{218}$ antibody are "purified antibodies" within the meaning of the present invention.

As used herein, the term "ligand" broadly refers to natural, synthetic or semi-synthetic molecules. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The ligand appropriate for the present invention can be selected and screened by a variety of means including random screening, rational selection and by rational design using for example protein or ligand modeling methods such as computer modeling. The terms "rationally selected" or "rationally designed" are meant to define compounds which have been chosen based on the configuration of interacting domains of the present invention. As will be understood by the person of ordinary skill, macromolecules having non-naturally occurring modifications are also within the scope of the term "ligand". For example, peptidomimetics, well known in the pharmaceutical industry and generally referred to as peptide analogs can be generated by modeling as mentioned above.

Antibodies

As used herein, the term "anti-PCSK9-ΔN$_{218}$ antibody" or "immunologically specific anti-PCSK9-ΔN$_{218}$ antibody" refers to an antibody that specifically binds to (interacts with) a PCSK9-ΔN$_{218}$ protein and displays no substantial binding to other naturally occurring proteins other than the ones sharing the same antigenic determinants as the PCSK9-ΔN$_{218}$ protein. The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g. Fab and Fab' fragments) which inhibit or neutralize their respective interaction domains in Hyphen and/or are specific thereto.

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ¹⁄₁₀ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum et al., 2004).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

As used herein, the term "a" or "the" means "at least one".

As used herein, the term "PCSK9 sequence" refers to a sequence having PCSK9 catalytic activity, and/or having the ability to traffic through its normal secretory pathway and to lower the protein level of LDLR at the cell surface. As used herein, it is not limited to the native PCSK9 sequence but encompasses any functional recombinant or mutant sequence, having preserved ability to reduce the level of LDLR (or other detector molecule) at the cell surface.

As used herein, the term "high enough" when referring the homology between a candidate surface receptor and a known cell surface receptor directly regulated by PCSK9 refers to more than 50% identity overall.

More specifically, in accordance with the present invention, there is provided a chimera protein comprising in the following order: a signal peptide, a proprotein convertase subtilisin/kexin type 9 preproprotein (PCSK9) sequence consisting of amino acid residues at positions 35 to 696 of SEQ ID NO: 38, a transmembrane domain and a cytosolic domain, wherein said cytosolic (CT) domain comprises a sequence able to recycle the protein from the cellular membrane to endosomes.

In a specific embodiment of the chimera, the PCSK9 sequence is as set forth in SEQ ID NO: 33. In another specific embodiment of the chimera, the PCSK9 sequence consists of amino acid residues at positions 35 to 694 of SEQ ID NO: 35. In another specific embodiment of the chimera, the PCSK9 sequence consists of amino acid residues at positions 35 to 691 of SEQ ID NO: 36. In another specific embodiment of the chimera, the PCSK9 sequence consists of amino acid residues at positions 31 to 692 of SEQ ID NO: 37. In another specific embodiment, the chimera further comprises at least one mutation associated with hypercholesterolemia. In another specific embodiment, the chimera further comprises at least one mutation associated with hypocholesterolemia. In another specific embodiment of the chimera, the PCSK9 sequence includes a basic amino acid specific proprotein convertases (PC)-recognition motif that comprises at least one mutation that reduces its recognition by furin/Proprotein convertase 5 (PC5)-like enzymes as compared to that of a wild-type PCSK9 sequence. In another specific embodiment of the chimera, the at least one mutation is selected from the group consisting of a substitution of phenylalanine for a leucine at position 220 of SEQ ID NO: 38 and a substitution of arginine for a serine at position 222 of SEQ ID NO: 38. In another specific embodiment of the chimera, the at least one mutation is a substitution of phenylalanine for a leucine at position 220 of SEQ ID NO: 38. In another specific embodiment of the chimera, the at least one mutation is a substitution of arginine for a serine at position 222 of SEQ ID NO: 38. In another specific embodiment of the chimera, the PCSK9 sequence includes a basic amino acid specific proprotein convertases (PC)-recognition motif that comprises at least one mutation that increases its recognition by furin/proprotein convertase 5 (PC5)-like enzymes as compared to that of a wild-type PCSK9 sequence. In another specific embodiment of the chimera, the at least one mutation is a substitution of phenylalanine for an arginine at position 220, a substitution of histidine for an arginine at position 221, a substitution of glutamine for an glutamic acid at position 223, and a substitution of an alanine for a leucine at position 224 of SEQ ID NO: 38. In another specific embodiment of the chimera, the transmembrane domain and the cytosolic domain are as set forth in SEQ ID NO: 22. In another specific embodiment of the chimera, the transmembrane domain and the cytosolic domain are as set forth in SEQ ID NO: 25. In another specific embodiment of the chimera, the transmembrane domain and the cytosolic domain are as set forth in SEQ ID NO: 28. In another specific embodiment, the amino acid sequence of the chimera is as set forth in SEQ ID NO: 20. In another specific embodiment, the chimera is encoded by a nucleotide sequence as set forth in SEQ ID NO: 19. In another specific embodiment, the amino acid sequence of the chimera is as set forth in SEQ ID NO: 24. In another specific embodiment, the chimera is encoded by a nucleotide sequence as set forth in SEQ ID NO: 23. In another specific embodiment, the amino acid sequence of the chimera is as set forth in SEQ ID NO: 27. In another specific embodiment, the chimera is encoded by a nucleotide sequence as set forth in SEQ ID NO: 26.

In accordance with another aspect of the present invention, there is provided a cell expressing the chimera protein of the present invention. In another embodiment, the cell expresses the chimera as a transiently transfected cell. In another embodiment, the cell expresses the chimera as a stably transfected cell. In another embodiment, the cell further expresses at its cell surface a low level of any one of a very low density lipoprotein receptor (VLDLR), a low density lipoprotein receptor (LDLR) and an apolipoprotein e receptor 2 (ApoER2).

In accordance with another aspect of the present invention, there is provided a cell-based assay for identifying a proprotein convertase subtilisin/kexin type 9 preproprotein (PCSK9) inhibitor, which comprises the steps of: (a) providing the cell of the present invention; and (b) comparing the cell surface expression of at least one PCSK9 target receptor, in the presence of a candidate inhibitor and in the absence thereof, whereby a higher level of the at least one receptor at the cell surface in the presence of the candidate inhibitor as compared to in the absence thereof is an indication that the candidate is a PCSK9 inhibitor.

In accordance with another aspect of the present invention, there is provided a cell-based assay for identifying a proprotein convertase subtilisin/kexin type 9 preproprotein (PCSK9) inhibitor, which comprises the steps of: (a) providing a cell expressing a PCSK9 having an increased resistance to a proprotein convertase (PC); and (b) comparing the cell surface expression of at least one PCSK9 target receptor, in the presence of a candidate inhibitor and in the absence thereof, whereby a higher level of the at least one receptor at the cell surface in the presence of the candidate inhibitor as compared to in the absence thereof is an indication that the candidate is a PCSK9 inhibitor.

In a specific embodiment of the cell-based assay, the PC is furin. In another specific embodiment of the cell-based assay, the PC is PC5. In another specific embodiment of the cell-based assay, the PCSK9 is as set forth in SEQ ID NO: 38 but includes at least one mutation selected from the group consisting of a substitution of phenylalanine for a leucine at position 220 and a substitution of arginine for a serine at position 222 of SEQ ID NO: 38. In another specific embodiment of the cell-based assay, the at least one PCSK9 target receptor is selected from the group consisting of a very low density lipoprotein receptor (VLDLR), a low density lipoprotein receptor (LDLR); an apolipoprotein receptor 2 (ApoER2), and a combination thereof. In another specific embodiment of the cell-based assay, the at least one PCSK9 target receptor is LDLR. In another specific embodiment of the cell-based assay, the at least one PCSK9 target receptor is VLDLR. In an other specific embodiment of the cell-based assay, the at least one PCSK9 target receptor is ApoER2.

In accordance with another aspect of the present invention, there is provided a method of identifying a cell surface receptor directly or indirectly regulated by PCSK9 comprising (a) providing a cell expressing the chimera protein of the present invention, and further expressing a candidate surface receptor; and (b) contacting the cell line with a PCSK9 inhibitor; whereby a higher level of expression of the candidate surface receptor in the presence of the inhibitor as compared to in the absence thereof is an indication that the candidate surface receptor is a cell surface receptor directly or indirectly regulated by PCSK9.

In accordance with another aspect of the present invention, there is provided a method of identifying a cell surface receptor for use in methods of the present invention: (a) comparing the amino acid sequence of a candidate cell surface receptor with that of at least one PCSK9 target receptor; whereby if the sequence homology between the candidate surface receptor and the PCSK9 target receptor is high enough, the candidate surface receptor is selected as a cell surface receptor for use in methods of the present invention.

In accordance with another aspect of the present invention, there is provided a method of identifying proprotein convertase subtilisin/kexin type 9 preproprotein (PCSK9) variant that has an increased activity in a cell as compared to a wild type PCSK9 comprising (a) testing a candidate PCSK9 variant for its resistance to furin, whereby a candidate PCSK9 variant having an increased resistance to furin as compared to that of the wild type PCSK9 is an indication that it is a PCSK9 variant having an increased activity.

In accordance with another aspect of the present invention, there is provided a method of identifying proprotein convertase subtilisin/kexin type 9 preproprotein (PCSK9) variant that has a reduced activity in a cell as compared to a wild type PCSK9 comprising (a) testing a candidate PCSK9 variant for its sensitivity to furin, whereby a candidate PCSK9 variant having an increased sensitivity to furin as compared to that of the wild type PCSK9 is an indication that it is a PCSK9 variant having a reduced activity in a cell.

In accordance with another aspect of the present invention, there is provided a method of identifying proprotein convertase-sensitivity proprotein convertase subtilisin/kexin type 9 preproprotein (PC-sensitivity PCSK9) variants comprising a) contacting a candidate PC-sensitivity PCSK9 variant with a PC, b) comparing the level of PCSK9 degradation or activity obtained with the candidate PC-sensitivity PCSK9 variant with that obtained with a wild type PCSK9, whereby a difference between the level of PCSK9 degradation or activity of the candidate PC-sensitivity PCSK9 variant and that of the wild type PCSK9 is an indication that the candidate is a PC-sensitivity PCSK9 variant.

In a specific embodiment, the method is a method of identifying a PC-resistant PCSK9 variant, whereby a lower level of PCSK9 degradation and/or a higher level of PCSK9 activity obtained with the candidate PC-sensitivity PCSK9 variant compared to that obtained with the wild type PCSK9 is an indication that the candidate is a PC-resistant PCSK9 variant. In another specific embodiment, the method is a method of identifying a PC-hypersensitive PCSK9 variant, whereby a higher level of PCSK9 degradation and/or a lower level of PCSK9 activity of the candidate PC-sensitivity PCSK9 variant compared to that of the wild type PCSK9 is an indication that the candidate is a PC-hypersensitive PCSK9 variant.

In accordance with another aspect of the present invention, there is provided a method of identifying a novel target in the proprotein convertase subtilisin/kexin type 9 preproprotein (PCSK9) regulatory pathway comprising (a) contacting a candidate proprotein convertase (PC) with a PCSK9; and (b) comparing the level of PCSK9 degradation or activity obtained in the presence of the PC and in the absence thereof, whereby a difference between the level of PCSK9 degradation or activity obtained in the presence of the PC and in the absence thereof is an indication that the PC is a novel target in the PCSK9 pathway.

In accordance with another aspect of the present invention, there is provided a purified polypeptide, the amino acid sequence of which consists of SEQ ID NO: 32. In accordance with another aspect of the present invention, there is provided a purified polypeptide, the amino acid sequence of which consists of SEQ ID NO: 31.

In accordance with another aspect of the present invention, there is provided a purified antibody that binds specifically to a polypeptide of the present invention.

In accordance with another aspect of the present invention, there is provided a kit comprising a purified ligand that specifically binds to a polypeptide of the present invention, and instructions to use the ligand for detecting in, or purifying the polypeptide from, a biological sample. In a specific embodiment, the kit further comprises a purified ligand that specifically binds to another polypeptide of the present invention. In another specific embodiment, the kit further comprises a purified ligand that binds to a first polypeptide of the present invention and to a polypeptide as set forth in SEQ ID NO: 34. In another specific embodiment, the purified ligand that specifically binds to a first polypeptide of the present invention is a purified antibody. In another specific embodiment, the purified ligand that specifically binds to a second polypeptide of the present invention is a purified antibody.

In accordance with another aspect of the present invention, there is provided a method of determining whether a biological sample contains a polypeptide of the present invention, comprising contacting the sample with a purified ligand that specifically binds to the polypeptide, and determining whether the ligand specifically binds to the sample, the binding being an indication that the sample contains the polypeptide. In a specific embodiment of the method, the ligand is a purified antibody.

In accordance with another aspect of the present invention, there is provided a method of purifying another polypeptide of the present invention from a biological sample containing the polypeptide, said method comprising: (a) contacting the biological sample with a purified ligand that specifically binds to the polypeptide, the ligand being bound to a solid support, to produce a ligand-polypeptide complex, (b) separating the complex from the remainder of the sample, and (c) releasing the polypeptide from the ligand thereby obtaining the purified polypeptide.

In accordance with another aspect of the present invention, there is provided a method of classifying a subject having a proprotein convertase subtilisin/kexin type 9 preproprotein (PCSK9)-associated disease or condition comprising measuring the concentration of a polypeptide, the amino acid sequence of which is as set forth in SEQ ID NO: 34 in a blood sample of the subject, wherein the results of the measuring step enables the classification of the subject into a subgroup. In a specific embodiment, the method further comprises measuring the concentration of a polypeptide, the amino acid sequence of which is as set forth in SEQ ID NO: 32 in the blood sample of the subject.

In accordance with another aspect of the present invention, there is provided a method of diagnosing a proprotein convertase subtilisin/kexin type 9 preproprotein (PCSK9)-associated disease or condition in a subject comprising (a) measuring the concentration of a polypeptide, the amino acid sequence of which is as set forth in SEQ ID NO: 34 and of another polypeptide of the present invention in a blood sample of a subject, wherein a ratio of the polypeptide, the amino acid sequence of which is as set forth in SEQ ID NO: 34: the polypeptide, the amino acid sequence of which is as set forth in SEQ ID NO: 32 that is higher than that in a control blood sample is an indication that the subject is predisposed to a PCSK9-associated disease or condition.

In accordance with another aspect of the present invention, there is provided a method of selecting a treatment for a subject comprising (a) measuring the concentration of a polypeptide, the amino acid sequence of which is as set forth in SEQ ID NO: 34 in a blood sample of the subject, wherein a concentration of the polypeptide higher in the blood sample of the subject than that in a control blood sample is an indication that a proprotein convertase subtilisin/kexin type 9 preproprotein (PCSK9) inhibitor may be a useful treatment for the subject. In a specific embodiment, the method further comprises (b) measuring the concentration of the polypeptide, the amino acid sequence of which is as set forth in SEQ ID NO: 32 in the blood sample of the subject, wherein a ratio of the polypeptide, the amino acid sequence of which is as set forth in SEQ ID NO: 34: the polypeptide, the amino acid of which is as set forth in SEQ ID NO: 32 that is higher in the blood sample of the subject than that in a control blood sample is an indication that a PCSK9 inhibitor may be a useful treatment for the subject. In another specific embodiment, the method is in vitro. In another specific embodiment, the subject is selected from the group consisting of a statin-treated subject, a subject resistant to lipid lowering treatment and a subject having a proprotein convertase subtilisin/kexin type 9 preproprotein (PCSK9)-associated disease or condition. In another specific embodiment, the PCSK9-associated disease or condition is selected from the group consisting of a cardiovascular disease, schizophrenia, autism, fetal growth restriction, obesity, and a recessive form of non-progressive cerebellar ataxia. In another specific embodiment, the cardiovascular disease is selected from the group consisting of hypercholesterolemia, atherosclerosis, stroke and ischemia. In another specific embodiment, the PCSK9-associated disease or condition is hypercholesterolemia. In another specific embodiment of the methods, the subject is a human.

In accordance with another aspect of the present invention, there is provided a method of modulating expression of a very low density lipoprotein receptor (VLDLR) or of a apolipoprotein e receptor 2 (ApoER2) at the surface of cells expressing VLDLR and/or ApoER2, comprising modulating proprotein convertase subtilisin/kexin type 9 preproprotein (PCSK9) activity, wherein the modulating of PCSK9 activity modulates the expression of VLDLR and/or ApoER2 at the surface of the cells. In another specific embodiment, the method is for decreasing the expression of VLDLR at the surface of muscle, heart, kidney and/or brain cells, and wherein the modulating PCSK9 activity is an increasing of PCSK9 secretion. In another specific embodiment, the method is for decreasing the expression of ApoER2 at the surface of brain, blood platelet and/or testis cells, and wherein the modulating of PCSK9 activity is an increasing of PCSK9 secretion. In another specific embodiment, the method is for increasing the expression of VLDLR at the surface of muscle, heart, kidney and/or brain cells, and wherein the modulating of PCSK9 activity is a decreasing of PCSK9 secretion. In another specific embodiment, the method is for increasing the expression of ApoER2 at the surface of brain, blood platelet and/or testis cells, and wherein the modulating PCSK9 activity is a decreasing of PCSK9 secretion. In another specific embodiment of the method, the decreasing of PCSK9 secretion is achieved with a PCSK9 inhibitor.

In accordance with another aspect of the present invention, there is provided a method of increasing LDLR expression at the surface of cells of tissues other than liver comprising inhibiting proprotein convertase subtilisin/kexin type 9 preproprotein (PCSK9) secretion from hepatocytes, wherein the inhibiting of PCSK9 secretion from hepatocytes increases the expression of LDLR at the surface of the cells.

In accordance with another aspect of the present invention, there is provided a use of a proprotein convertase subtilisin/kexin type 9 preproprotein (PCSK9) modulator for modulating expression of a very low density lipoprotein receptor (VLDLR) or of a apolipoprotein e receptor 2 (ApoER2) at the surface of cells expressing VLDLR and/or ApoER2.

In accordance with another aspect of the present invention, there is provided a use of a proprotein convertase subtilisin/kexin type 9 preproprotein (PCSK9) modulator in the making of a medicament for modulating expression of a very low density lipoprotein receptor (VLDLR) or of a apolipoprotein e receptor 2 (ApoER2) at the surface of cells expressing VLDLR and/or ApoER2. In a specific embodiment, the use is for decreasing the expression of VLDLR at the surface of muscle, heart, kidney and/or brain cells, and wherein the PCSK9 modulator is able to increase PCSK9 secretion. In a specific embodiment, the use is for decreasing the expression of ApoER2 at the surface of brain, blood platelet and/or testis cells, and wherein the PCSK9 modulator is able to increase PCSK9 secretion. In a specific embodiment, the use is for increasing the expression of VLDLR at the surface of muscle, heart, kidney and/or brain cells, and wherein the PCSK9 modulator is able to decrease PCSK9 secretion. In a specific embodiment, the use is for increasing the expression of ApoER2 at the surface of brain, blood platelet and/or testis cells, and wherein the PCSK9 modulator is able to decrease PCSK9 secretion. In a specific embodiment, the PCSK9 modulator is a PCSK9 inhibitor.

In accordance with another aspect of the present invention, there is provided a use of an inhibitor of proprotein convertase subtilisin/kexin type 9 preproprotein (PCSK9) secretion from hepatocytes for increasing LDLR expression at the surface of cells of tissues other than liver.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 6 shows the amino acid sequences alignment of various species of PCSK9 in the region of arginine at position 218 ($Arg_{218}$), from the P8 to the P4' processing site: h: human; m: mouse; r: rat; xl: *Xenopus laevis* (SEQ ID NO: 10); zf: zebrafish (SEQ ID NO: 11); ck: chicken (SEQ ID NO: 12); tn:

Figure 7:
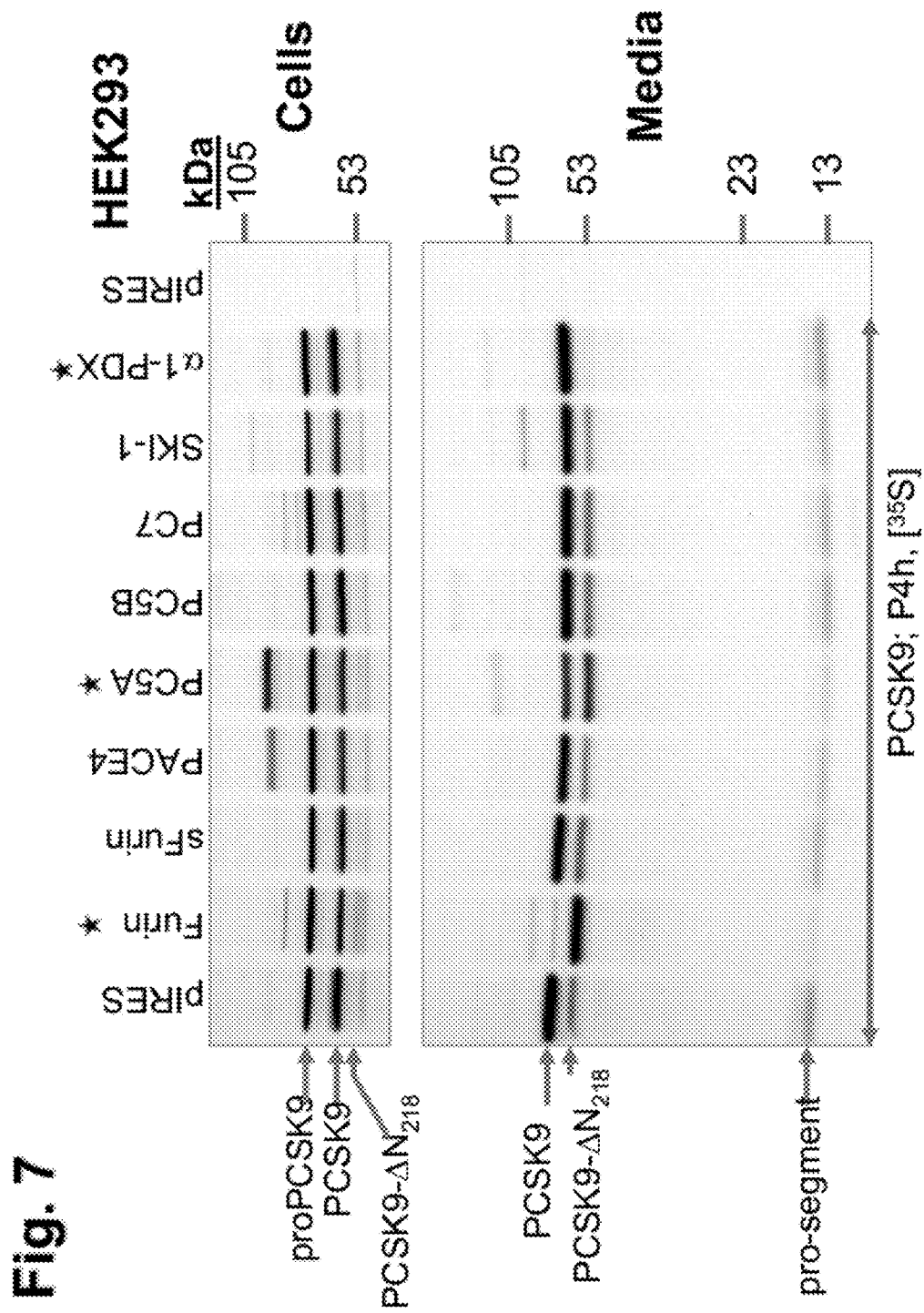
Figure 8:
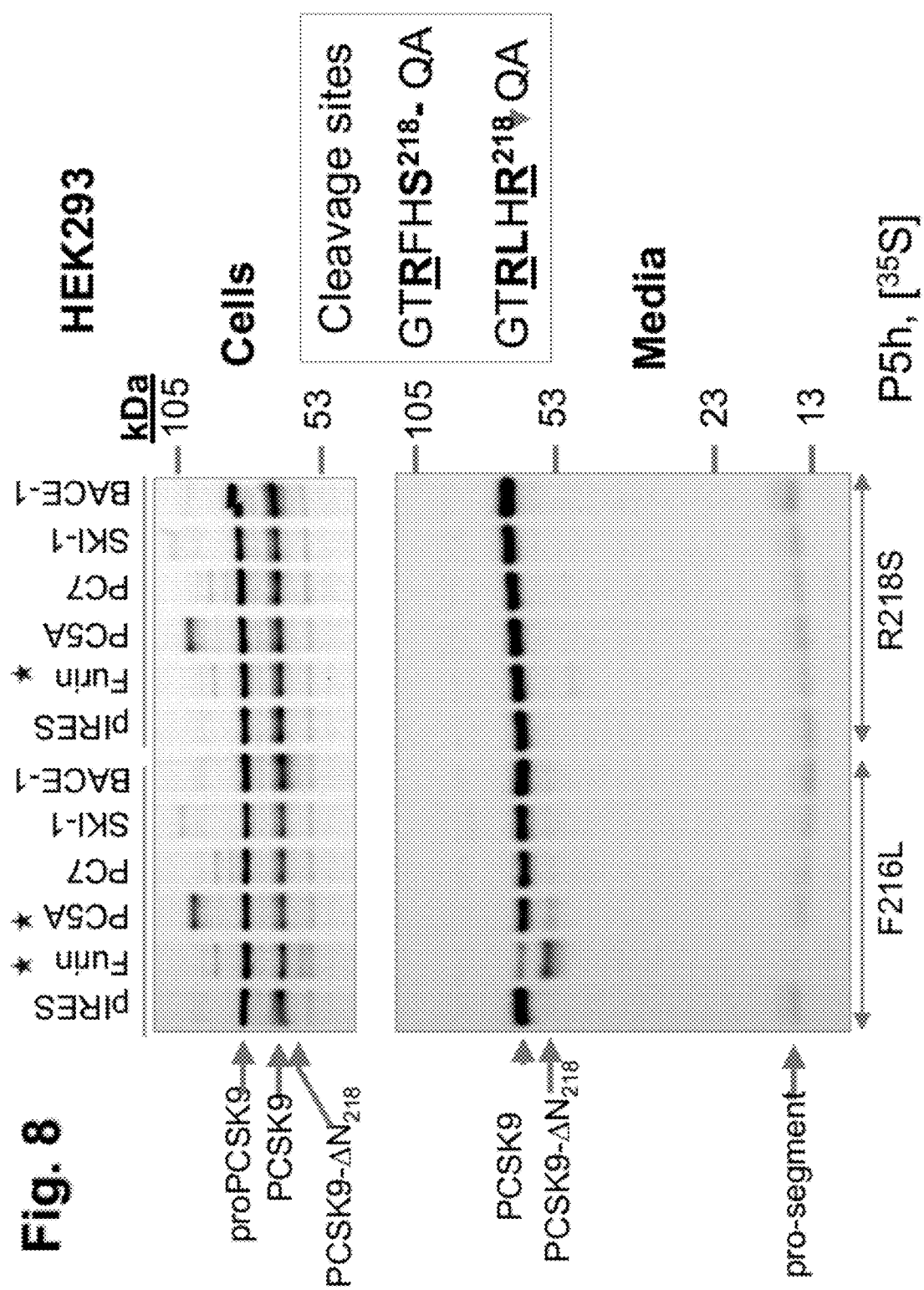
Figure 9:
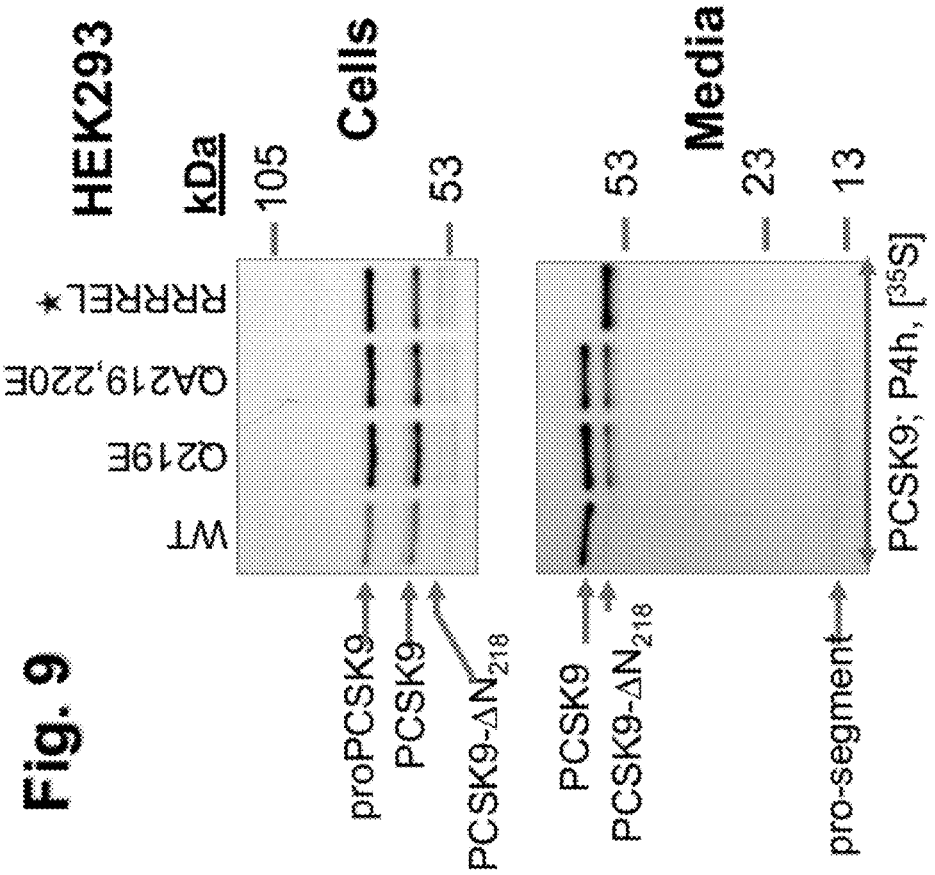
Figure 10:
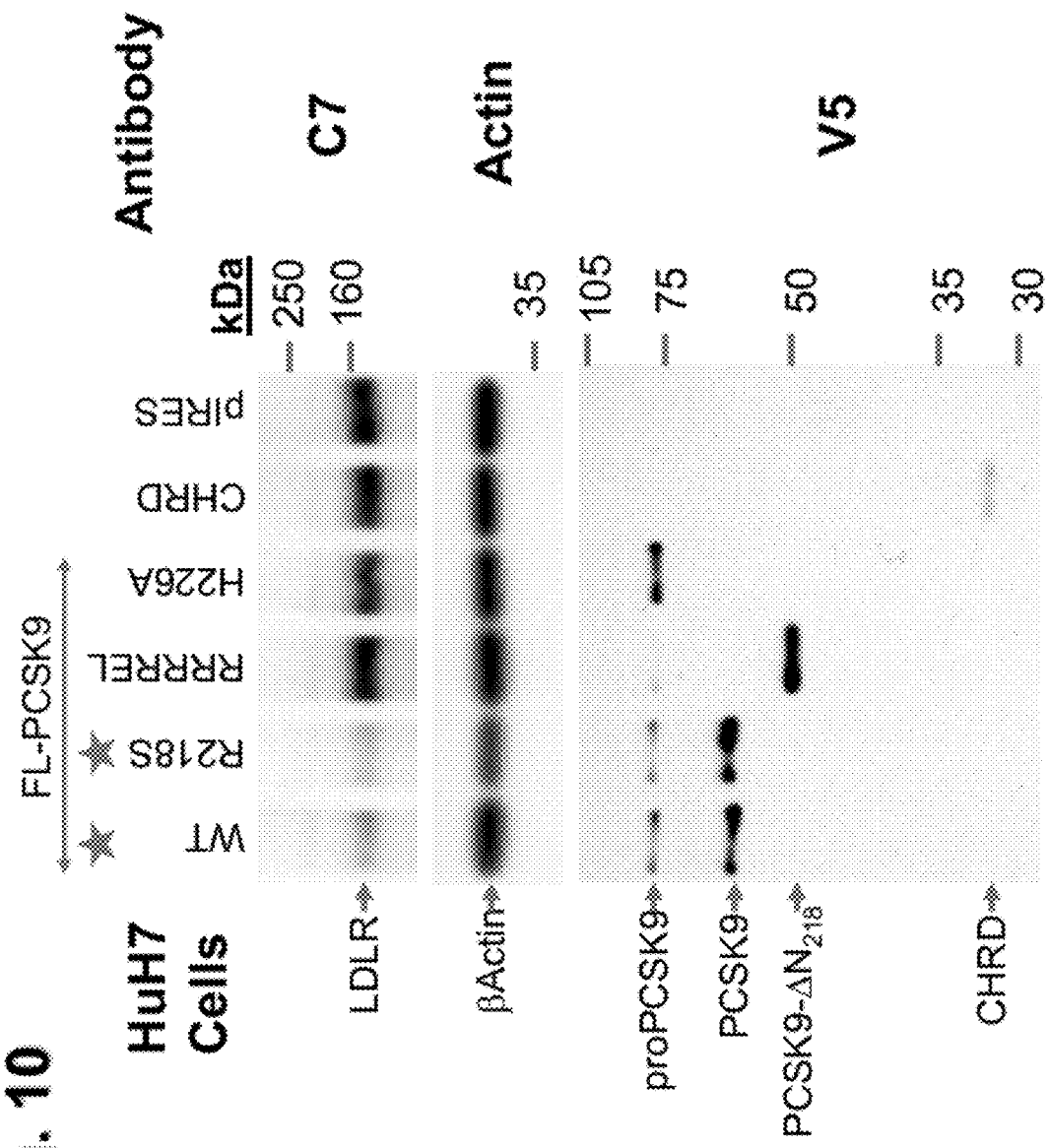
Figure 11:
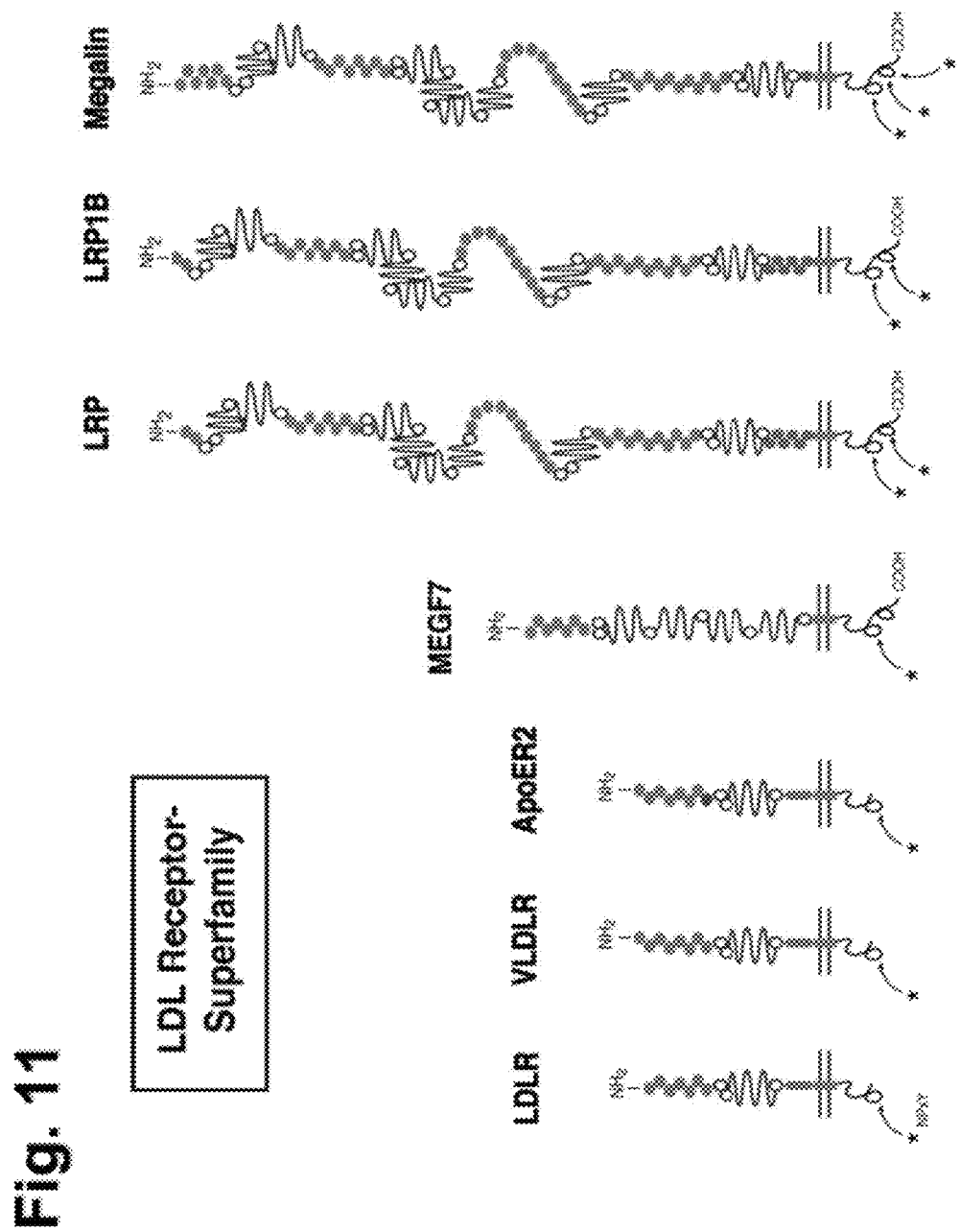
Figure 12:
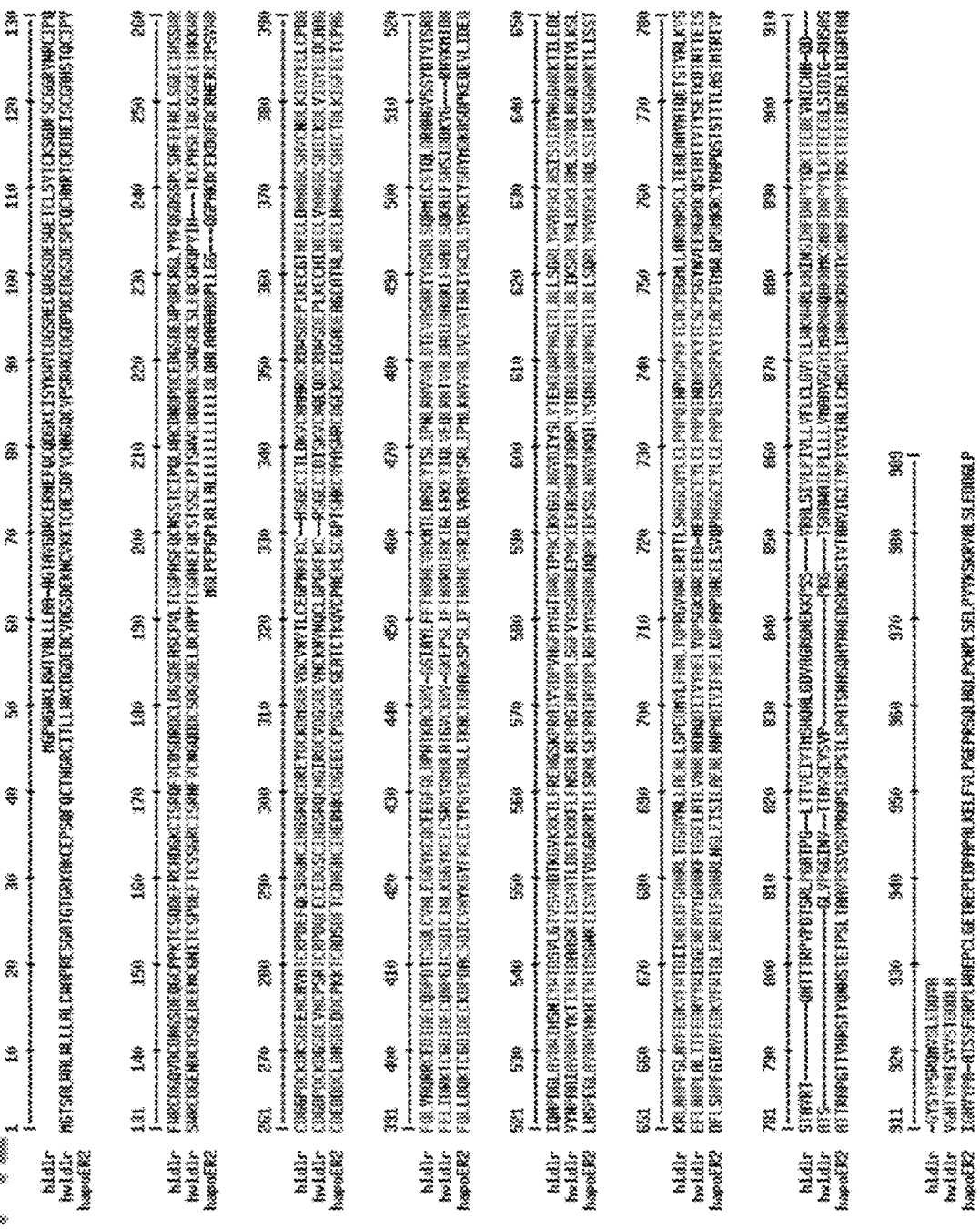
Figure 13:
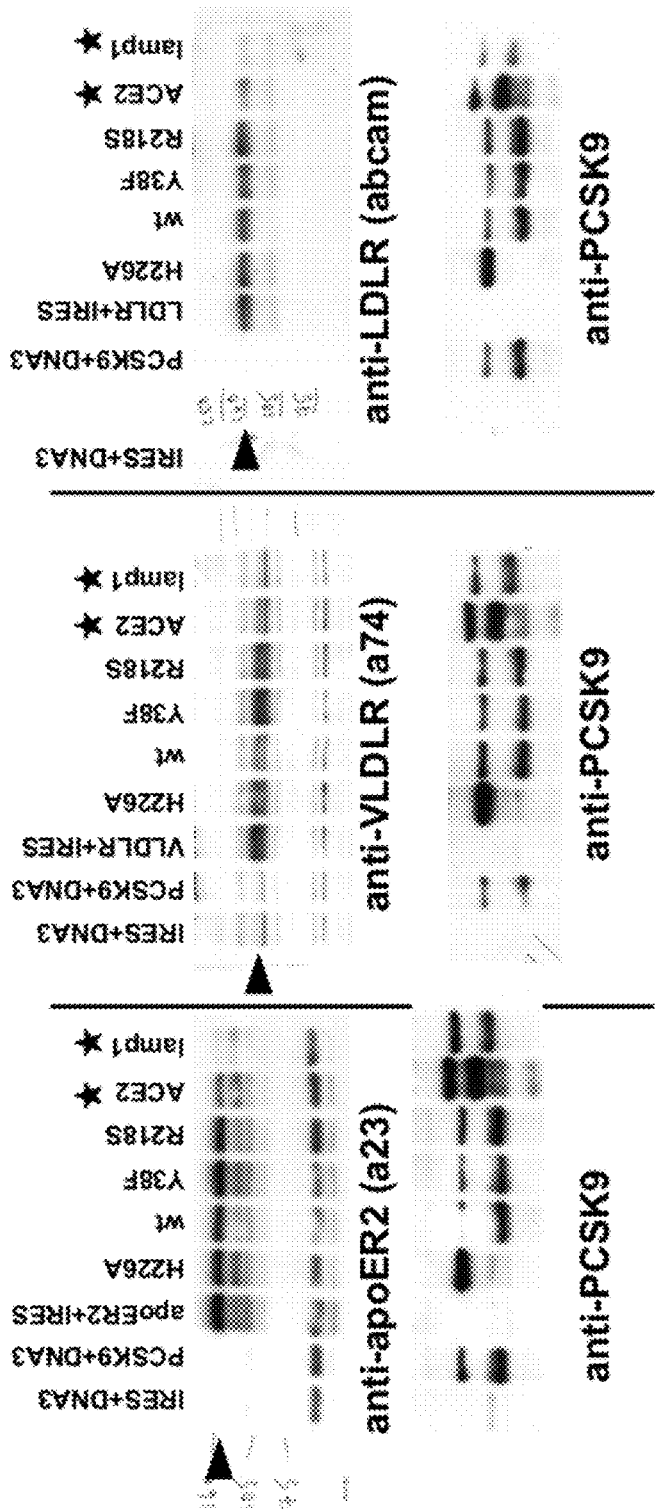
Figure 14:
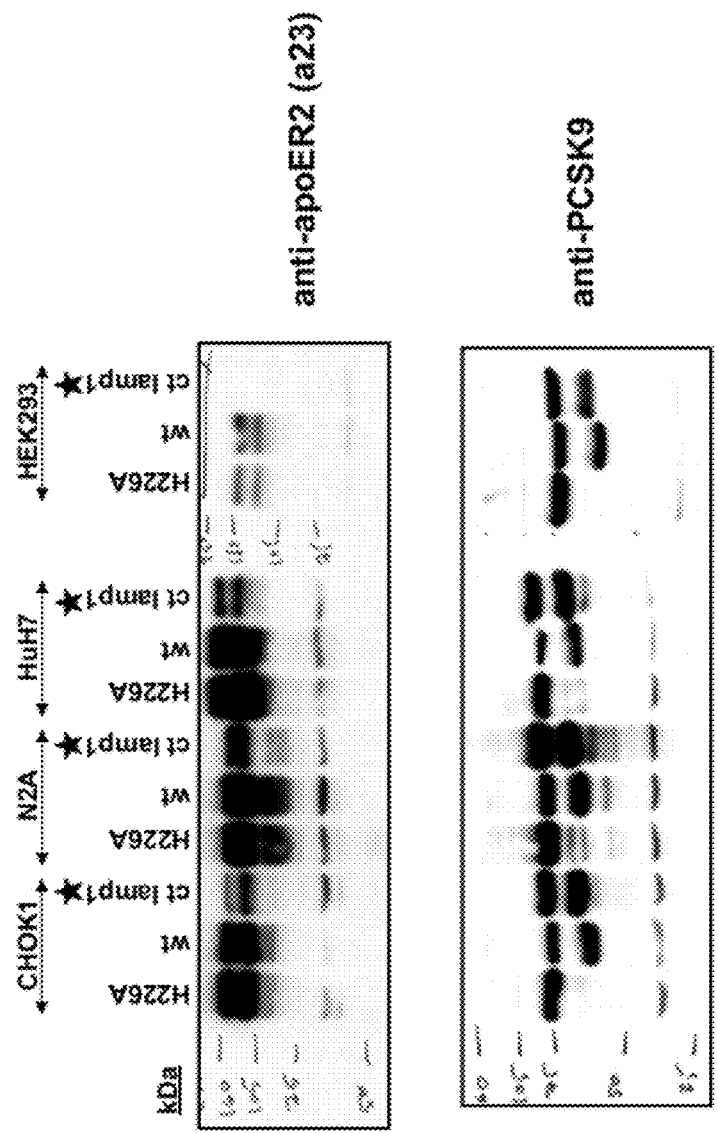
Figure 15:
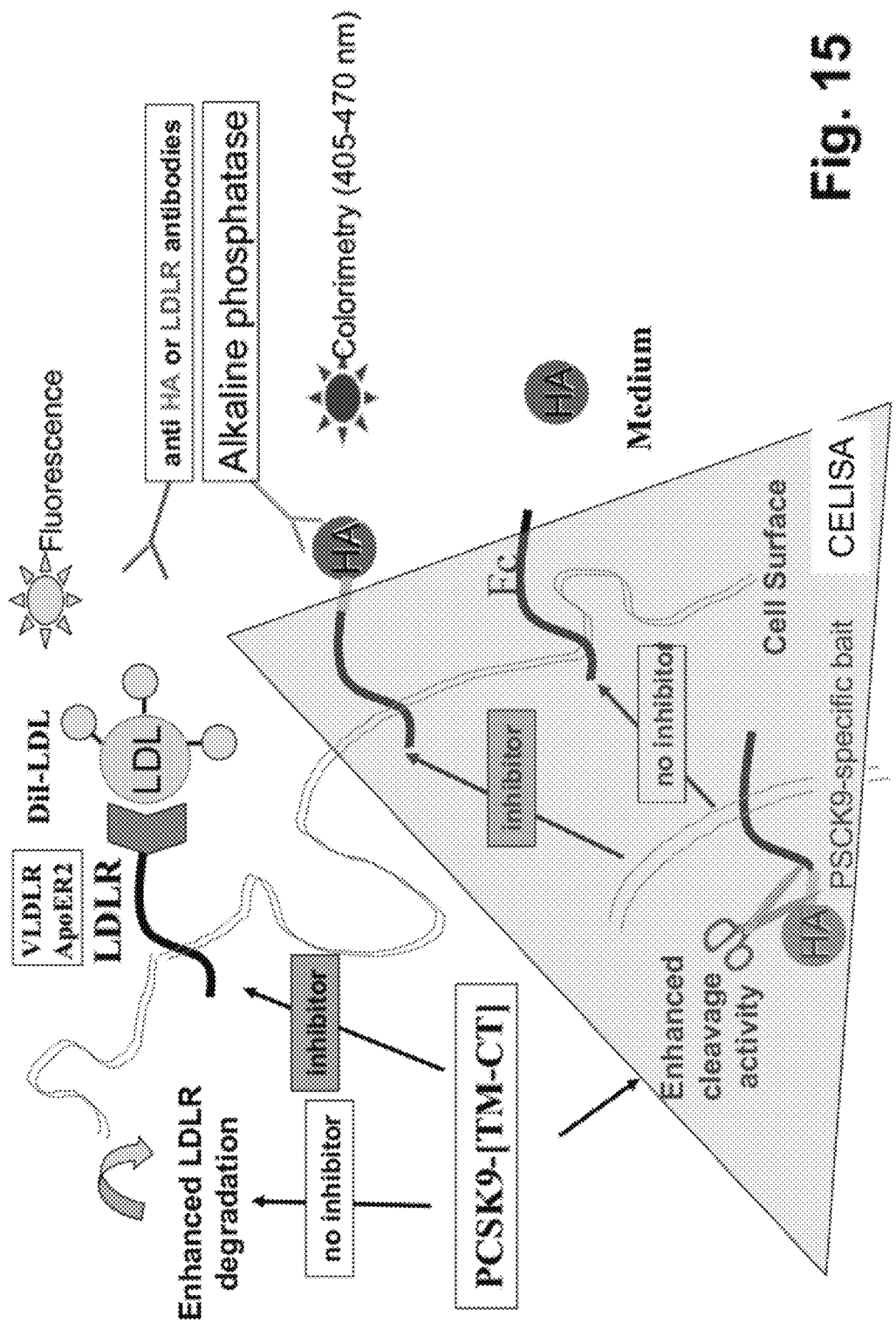
Figure 20:
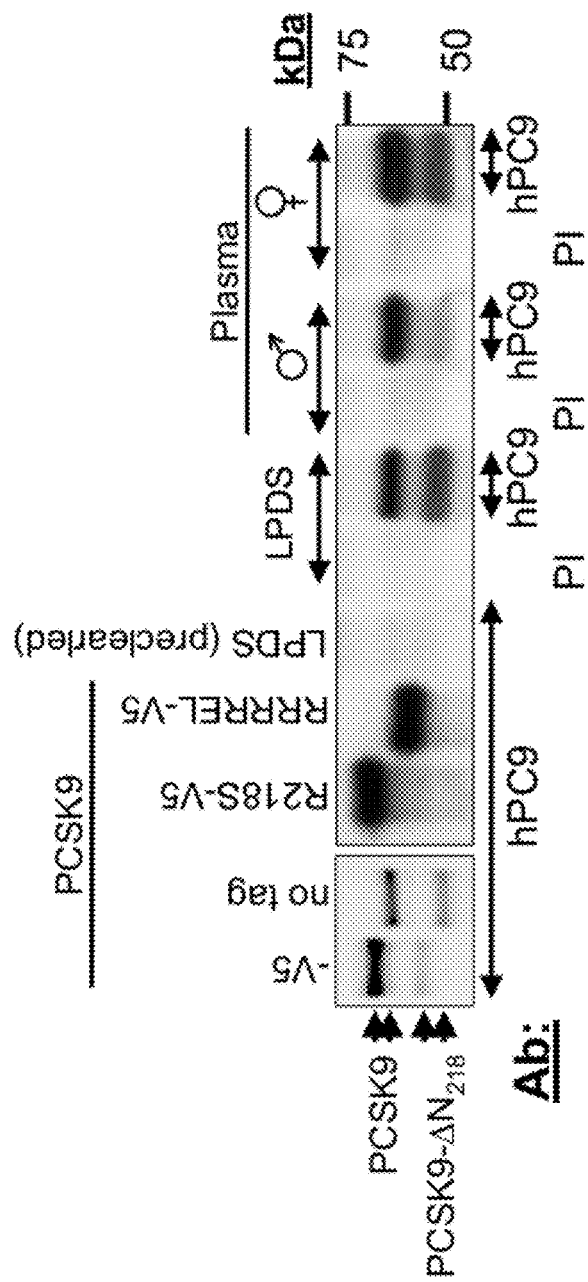

*Tetraodon nigroviridis* (SEQ ID NO: 13); fr: *Fugu rubripes* (SEQ ID NO: 14). The corresponding sequences of the F216L (SEQ ID NO: 15) and R218S (SEQ ID NO: 16) mutants are shown for comparison at the bottom;

FIG. 7 shows the cleavability of overexpressed human PCSK9 in HEK293 cells by the indicated proprotein convertases and the inhibition of this process by the PC-inhibitor α1-PDX. Twenty four hours following the co-transfection of PCSK9 with a PC or with an empty vector control (the pIRES-2 vector from Invitrogen), the cells were labeled with [$^{35}$S] [Met+Cys] for 4 h (P4h). The cell lysates (Cells) and media were immunoprecipitated with a V5-mAb and the immunoprecipitates resolved by SDS-PAGE, as described (Seidah et al., 2003). sFurin represents the soluble form of furin lacking the transmembrane-cytosolic tail (Decroly et al., 1996). The stars point to lanes where either processing occurred (with Furin and PC5A) or was inhibited (α1-PDX). From now on, N2 is defined herein as the N-terminal 218 amino acid truncated PCSK9 product (PCSK9-$\Delta$N$_{218}$). The pIRES lanes represent the empty vector pIRES-2 either alone or co-transfected with PCSK9 (as indicated at the bottom of the panel) as controls;

FIG. 8 shows the cleavability of overexpressed human PCSK9 mutants F216L and R218S in HEK293 cells by the indicated proprotein convertases, or by 3-secretase BACE1 (Benjannet et al., 2001). Twenty four hours following the co-transfection of the PCSK9 natural mutants and each PC or with an empty vector control (pIRES). The cells were labeled with [$^{35}$S] [Met+Cys] for 5 h (P5h) and the cell lysates (Cells) and media analyzed as in FIG. 7. The stars point to lanes where either processing occurred (Furin and PC5A) or was inhibited by the presence of the mutation (R$^{218}$S with furin). Cleavage sites GTRFHS$^{218}$↓QA (SEQ ID NO: 17); GTRLHR$^{218}$↓QA (SEQ ID NO: 18);

FIG. 9 schematically shows the biosynthetic analysis of the processing of overexpressed human PCSK9 and its indicated mutants following a 5 h pulse-labelling of HEK293 cells with [$^{35}$S] [Met+Cys] as described in FIG. 7. The star emphasizes the effectiveness of the RRRR$_{218}$EL (SEQ ID NO: 6) mutant to allow the complete processing of PCSK9 into the PCSK9-$\Delta$N$_{218}$ form by endogenous Furin. PCSK9 amino acid sequence in the vicinity of position 218 RFHR$_{218}$QA (SEQ ID NO: 4) (WT); RFHR$_{218}$EA (SEQ ID NO: 6) (Q219E); RFHR$_{218}$EL (SEQ ID NO: 7) (QA219,220EL); RRRR$_{218}$EL (SEQ ID NO: 5);

FIG. 10 shows the Western blot analysis of the level of endogenous LDLR in HuH7 cells transiently transfected with the indicated PCSK9 constructs, all containing a C-terminal V5-tag. The stars point to the only two constructs that significantly decreased the level of endogenous LDLR (detected by a commercially available C7-mAb). Cells expressed either full length PCSK9 (FL-PCSK9), namely wild type sequence (WT), mutated R218S, RRRREL (SEQ ID NO: 5) or active site H226A; a truncated PCSK9 construct with the Cys/His rich domain (signal peptide fused to amino acid 455-692 of PCSK9 and ending with a V5 tag) (CHRD) or the empty vector control (pIRES-2). The levels of β-actin was used as control, as well as the level of PCSK9 intracellular proteins produced (detected by a V5-mAb);

FIG. 11 presents a schematic diagram of the LDLR superfamily;

FIG. 12 presents the amino acid sequences alignment of the human LDLR (SEQ ID NO: 118), VLDLR (SEQ ID NO: 119) and ApoER2 (SEQ ID NO: 120), indicating a high degree of sequence identity between the three proteins;

FIG. 13 shows the Western blot analysis of the level of overexpressed ApoER2, VLDLR, and LDLR in CHOK1 cells transiently co-transfected with the indicated PCSK9 constructs (at the top of the lanes) or empty vectors (pIRES2-EGFP=IRES; pcDNA3=DNA3; Invitrogen). The triangle indicates the position in the gel of respectively ApoER2 (first panel), VLDLR (second panel) and LDLR (third panel). The stars point to the constructs that significantly decreased the level of the receptors (detected by antibodies mentioned below the SDS-PAGE gel, where a23 and a74 are generous gifts from Dr. Joachim Nimpf, Austria and the commercial LDLR antibody was from abcam). The PCSK9 Y38F is a mutant where the Tyr-sulfation of the prosegment is eliminated. The intracellular levels of PCSK9 (detected by a specific in-house polyclonal antibody made in rabbits against human PCSK9) are shown in the corresponding cell lysates in the lower panels;

FIG. 14 shows the Western blot analysis of the level of overexpressed ApoER2 in various cells, such as CHOK1, Neuro2A, HuH7 and HEKL293 cells, transiently co-transfected with the indicated PCSK9 constructs (top lanes). The stars point to the construct [PCSK9-TM-CT (Lamp1)] that significantly decreased the level of ApoER2 in all cells tested. The intracellular levels of PCSK9 (detected by a specific in house antibody against human PCSK9) are shown in the bottom panels;

FIG. 15 schematically shows a multiple positive read out screening assay for the identification of compounds causing PCSK9 inhibition. In this assay, the cell contains a) one chimera of the present invention leading to the expression of a PCSK9 associated with an increase cellular activities (PCSK9-[TM-CT]) and, b) a chimeric construction containing the target site for PCSK9 enzymatic activity (CELISA). In the presented example, the increased detection at the cell surface of endogenous LDLR and of chimeric protein harbouring the HA tag are both dependent on the inhibition of the PCSK9 activity;

FIG. 16 shows the cDNA nucleotide sequence (SEQ ID NO: 19) and the amino acid sequence (SEQ ID NO: 20) of a chimera protein comprising a full-length human PCSK9 (1-692) (SEQ ID NO: 21) indirectly fused to the transmembrane and the cytosolic domains (TM-CT) of LDLR. TM in bold and CT underlined (SEQ ID NO: 22). The fragment between the PCSK9 1-692 and the TM-CT is a V5-tag and is optional;

FIG. 17 shows the cDNA nucleotide sequence (SEQ ID NO: 23) and the amino acid sequence (SEQ ID NO: 24) of a chimera protein comprising a full-length human PCSK9 (1-692) (SEQ ID NO: 21) fused to the transmembrane and the cytosolic domains (TM-CT) of Lamp1 (SEQ ID NO: 25). TM in bold and CT underlined. The fragment between the PCSK9 1-692 and the TM-CT is a V5-tag and is optional;

FIG. 18 shows the cDNA nucleotide sequence (SEQ ID NO: 26) and the amino acid sequence (SEQ ID NO: 27) of a chimera protein comprising full-length human PCSK9 (1-692) (SEQ ID NO: 21) fused to the transmembrane and the cytosolic domains (TM-CT) of ACE2. TM in bold and CT underlined (SEQ ID NO: 28). The fragment between the PCSK9 1-692 and the TM-CT is a V5-tag and is optional;

FIG. 19 shows: 1. the amino acid sequence of human full-length PCSK9 (1-692) (SEQ ID NO: 21); 2. the amino acid sequence of Pro-protein PCSK9 (i.e. without signal peptide) (31-692) (SEQ ID NO: 33); 3. the amino acid sequence of the active full-length PCSK9 ("active form") (153-692) (SEQ ID NO: 34); 4. the N-terminal fragment of the furin/PC5-cleaved PCSK9 active form (SEQ ID NO: 31) (153-218); and 5. the C-terminal fragment of the furin/PC5-cleaved PCSK9 active form (219-692) (PCSK9-$\Delta$N$_{218}$) (SEQ ID NO: 32). In these sequences, the signal peptide is underlined (SEQ ID NO: 29), the prosegment is bolded (SEQ ID NO: 30), the N-terminal fragment resulting from the cleavage of the furin/PC5 is italicized (SEQ ID NO: 31) and the C-terminal fragment (N2) resulting from the cleavage of the furin/PC5 is in regular font (SEQ ID NO: 32);

FIG. 20 shows the presence of the Furin/PC5-cleaved PCSK9 form in human plasma. Human plasma was obtained from two healthy volunteers, one male and one female. Human lipoprotein-deficient serum (LPDS) was obtained from a commercial pool of plasma. One-hundred microliters of plasma were immunoprecipitated with Ab1-hPC9 or pre-immune rabbit serum (PI). Immunoprecipitates were separated on 8% glycine gels, and PCSK9 forms were detected with rabbit TrueBlot according to the manufacturer's instructions. Media from HEK293 cells transfected with R218S or RRRR$^{218}$EL (SEQ ID NO: 6) were immunoprecipitated and loaded as markers of PCSK9 forms. Note the migration difference between V5-tagged and untagged PCSK9 (left panel);

FIG. 21 shows the degradation of the VLDLR in skeletal muscles of transgenic mice overexpressing PCSK9 in the liver. Immunohistochemistry of VLDLR (red) in skeletal mouse muscles of control Pcsk9+/+, Pcsk9−/− (Pcsk9 knock-out) and transgenic mice (Tg-hPcsk9-V5). The nuclei were stained using TO-PRO-3 (blue; invitrogen). scale: 50 µM; and FIG. 22 presents an alignment of human full-length PCSK9 (1-692) (SEQ ID NO: 21) (NP_777596); mouse full-length PCSK9 (SEQ ID NO: 35) (NP_705793); rat full-length PCSK9 (SEQ ID NO: 36) (NP_954862); and monkey predicted full-length PCSK9 (SEQ ID NO: 37) (XP_513430) wherein "*" denotes that the residues in that column are identical in all sequences of the alignment, ":" denotes that conserved substitutions have been observed, and "." denotes that semi-conserved substitutions have been observed. A consensus sequence derived from this alignment (SEQ ID NO: 38) is also presented. In this consensus, x can be any amino acid and in addition, at positions where the amino acid residue is absent in at least one species of the alignment (denoted by a dash in the alignment), x can also be absent. In specific embodiments of the consensus, mutations associated with diseases or conditions such as dyslipidemia are excluded from the consensus sequence. Hence, in specific embodiments, at position 50 of SEQ ID NO: 38, X is not leucine. In other specific embodiments, one or more X are defined as being any of the amino acids found at that position in the sequences of the alignment. Consensus sequences are also derived from each of the signal peptide (SEQ ID NO: 121), the pro-protein PCSK9 without signal peptide (SEQ ID NO: 122), the prosegment (SEQ ID NO: 123), the active full-length PCSK9 (without signal peptide and prosegment) (SEQ ID NO: 124), the N-terminal fragment of a furin/PC5 cleaved PCSK9 (SEQ ID NO: 125), and the C-terminal fragment of a furin/PC5 cleaved PCSK9 (SEQ ID NO: 126).

DESCRIPTION OF ILLUSTRATIVE EMBODIMENTS

In a first aspect of the present invention, the examples described herein present cells expressing chimeras presenting a PCSK9 sequence developed in light of an increase PCSK9-associated cellular activity (FIGS. 3-10). These examples also describe the use of these cells for the identification of convertases involved in the PCSK9 regulation (FIG. 5-10). Other examples describe the use of these cells to identify novel surface molecules sensitive to PCSK9 and that could be used as detector molecules in cell-based assays (FIGS. 11-14). The method chosen is based on positive and sensitive selection for PCSK9 inhibitors that enhance the cell surface expression of detector molecules (FIG. 15).

In a second aspect of the present invention, the examples described herein present assays for the identification of PCSK9 inhibitors that induces the reappearance of multiple read out at the surface of cell (LDLR, VLDLR and/or ApoER2).

The present invention is illustrated in further details by the following non-limiting examples presenting sensitive tailor-made cell-based assays designed to isolate convertases inhibitors.

EXAMPLE 1

Identification of PCSK9 with Enhanced Cellular Activities

Construction of the Chimera

The constructions of the three presented PCSK9 chimera (FIG. 3) were obtained by standard PCR and cloning techniques (Wiley, J. & Sons) and were made in the model vector phCMV3 (Invitrogen). The cDNA and amino acid sequences appear in FIGS. 16-18. The chimera presented contain the TM-CT domains of the human low density lipoprotein receptor (LDLR), human lysosomal-associated membrane protein 1 (Lamp1) or human angiotensin converting enzyme-2 (ACE2).

Degradation of LDLR Cell Surface in the Presence of the Chimera

Figure 1:
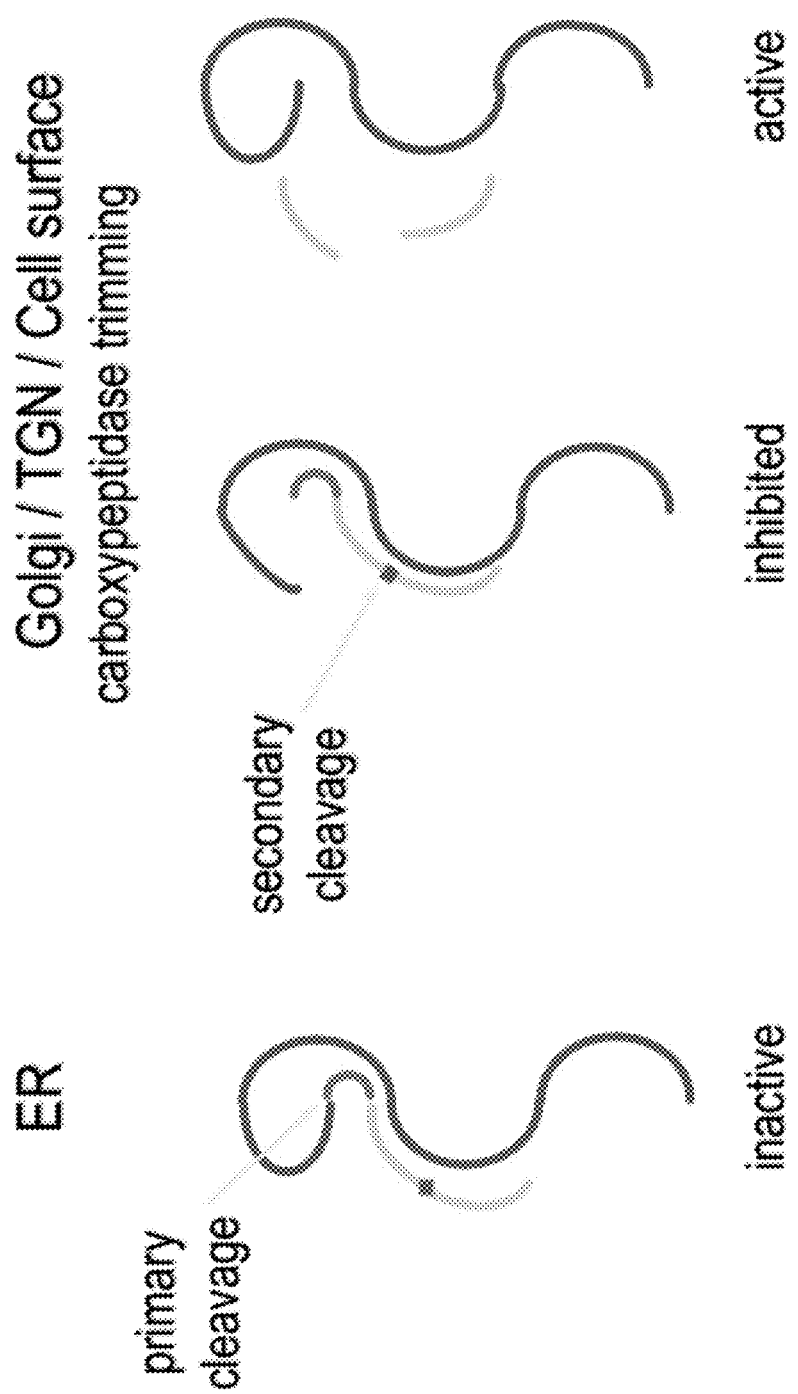
FIG. 1 presents a schematic diagram of the steps involved in the zymogen activation of PCs that start in the ER where the primary autocatalytic cleavage occurs. This allows the inactive complex of prosegment-PC to exit from the ER and traffic towards the Golgi and the trans Golgi Network (TGN). The dissociation of the prosegment from the active enzyme takes place usually in an acidic compartment, which is believed to be the endosomes in the case of PCSK9, whereby it is likely that PCSK9 will cleave its prosegment a second time to liberate itself and be active in trans on other proteins.
Figure 2:
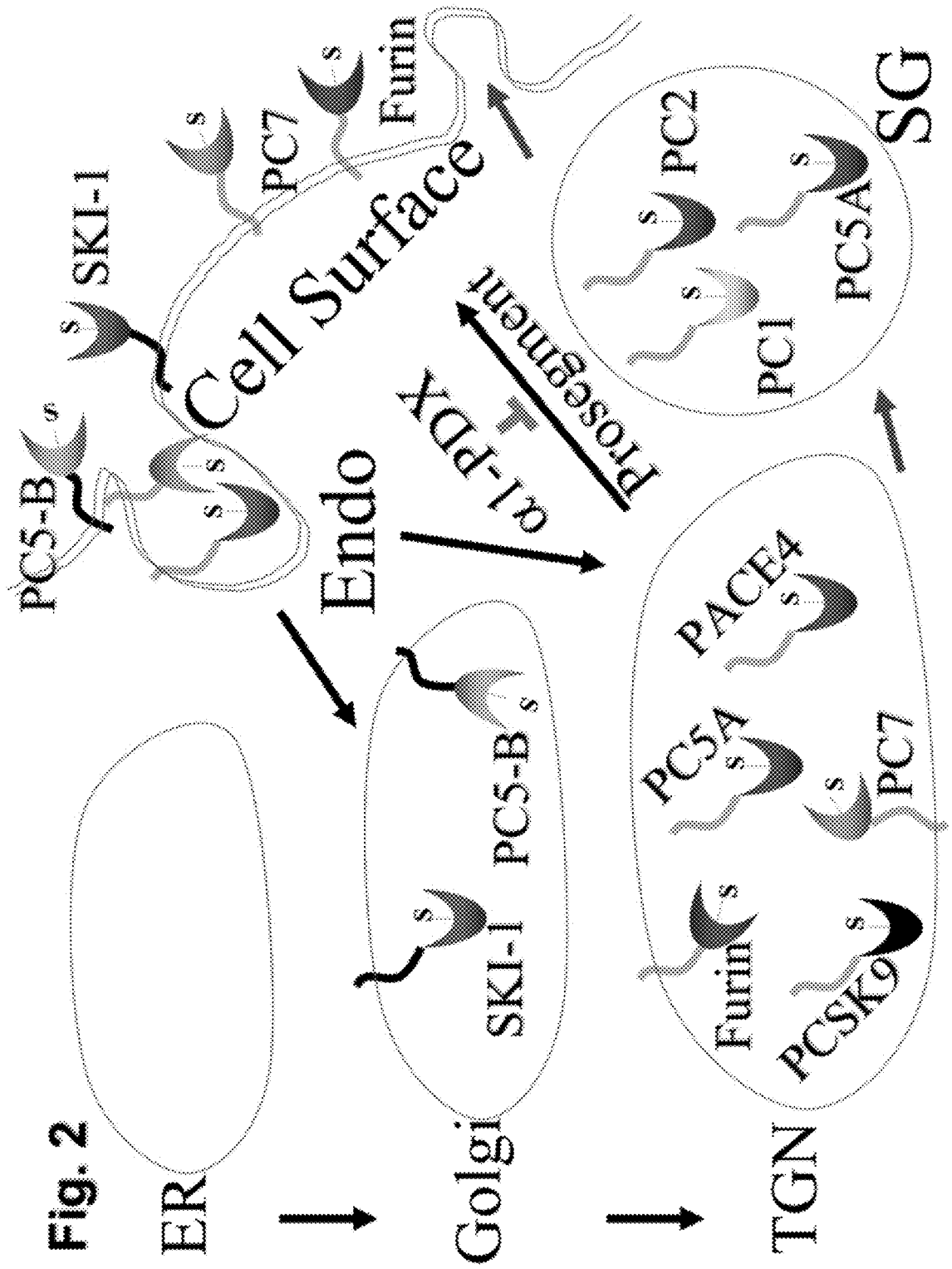
FIG. 2 schematically presents the cell localization where PCs cleave their substrates in the secretory and endocytic pathways. ER: endoplasmic reticulum; TGN: trans Golgi network; SG: secretory granule; s: Serine residue from the active site from the PC-like; Endo: endosome; prosegment, PC-derived inhibitory prosegment.
Figure 3:
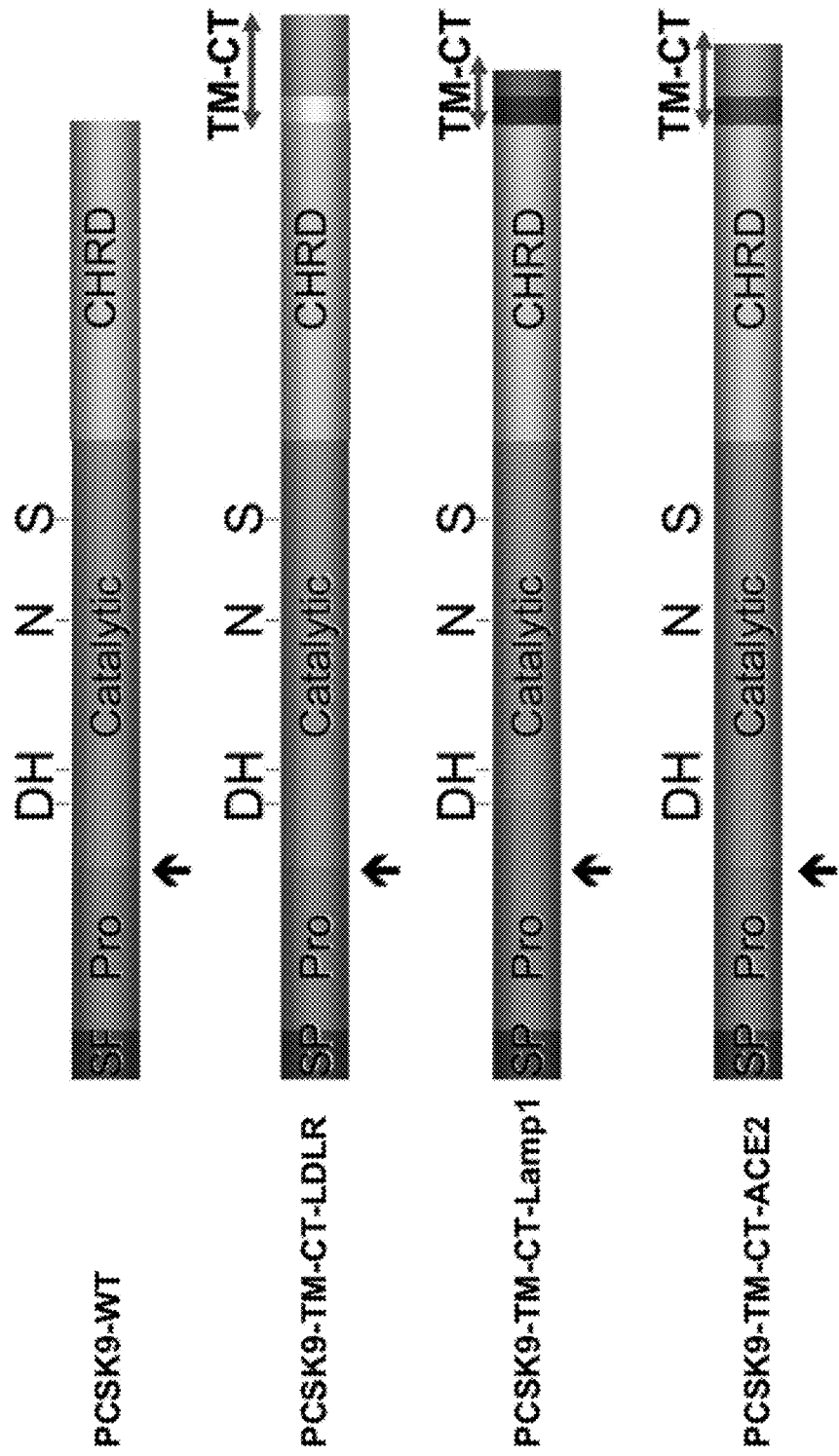
FIG. 3 schematically presents three examples of PCSK9-transmembrane-cytosolic tail (TM-CT) chimeras used in the present invention along with a wild-type PCSK9. Herein, SP, Pro, Catalytic, and CHRD represent 4 domains of PCSK9: the signal peptide, prosegment, catalytic domain and Cys/His rich domain, respectively. In these chimeras the C-terminus of PCSK9 is fused to the TM-CT of LDLR, Lamp1 and ACE2 respectively.
Figure 4:
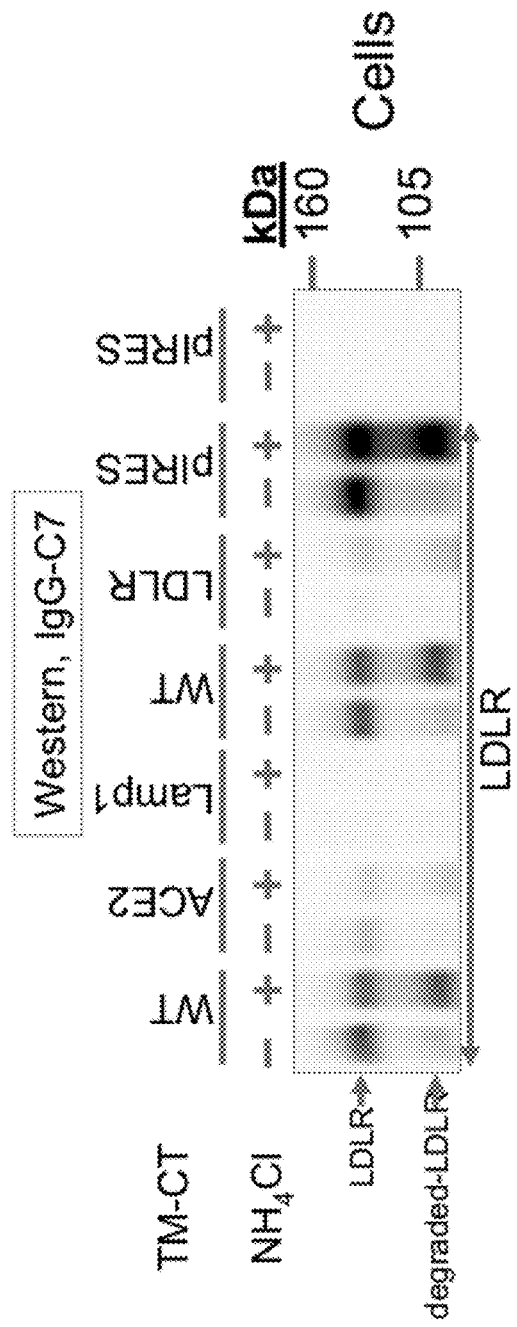
FIG. 4 shows the Western blot analysis of the level of LDLR (detected by a commercially available C7-mAb) in HEK293 cells transiently co-transfected with LDLR and each of the indicated wild type (WT) PCSK9 or PCSK9-TM-CT chimeras (see FIG. 5), in the presence (+) or absence (−) of $NH_4Cl$ for 24 h. Note that $NH_4Cl$ allows the rescue from degradation of an intermediate immunoreactive ~105 kDa form of LDLR that is likely found in endosomes. The pIRES lanes represent the empty vector pIRES-2 either alone or co-transfected with LDLR (as indicated at the bottom of the panel) as controls.

HEK293 cells were transiently transfected with different PCSK9-chimera constructions (Benjannet et al., 2004). FIG. 4 shows the Western blot analysis of the level of LDLR (as detected by a commercially available C7-mAb) in HEK293 cells transiently co-transfected with full length LDLR and, as indicated at the top of each lanes, with either wild type (WT) PCSK9, a PCSK9-TM-CT chimera or an empty vector (pIRES). Cells were either treated (+) or not (−) with 5 mM NH$_4$Cl for 24 h. Note that NH$_4$Cl allows the rescue from degradation of an intermediate immunoreactive ~105 kDa form of LDLR that is likely found in endosomes. The pIRES lanes represent the empty vector pIRES-2 either alone or co-transfected with LDLR (as indicated at the bottom of the panel) as controls. HEK293 cells co-transfected with LDLR in the presence of any of the three TM-CT chimera tested shows an enhanced degradation of LDLR as compared to the wild type PCSK9 control.

The LDLR's TM-CT was selected for this particular example as it is one of the proteins targeted for enhanced degradation by PCSK9. Other members of the LDLR superfamily (FIG. 11) could have been used, including those that the applicants have shown herein to be degraded by PCSK9, i.e., VLDLR and ApoER2 (FIGS. 13 and 14). This approach is not either limited to TM-CTs of proteins that are targets for PCSK9-enhanced degradation, as it is also shown herein that the use the TM-CTs of the SARS coronavirus receptor the angiotensin converting enzyme-2 (ACE2) (Bergeron et al., 2005; Vincent et al., 2005) or even TM-CT from lysosomal proteins such as LAMP1 (Conesa et al., 2003) also induce an enhanced degradation of the LDLR at the cell surface (FIG. 4).

PCSK9 Mutations and their Effects on PCSK9 Processivity

The processing of different PCSK9 mutants associated with familial hypercholesterolemia (FIG. 5A and Table 1 below) were analyzed.

TABLE 1

PCSK9 variants associated with hypocholesterolemia, hypercholesterolemia and other PCSK9 variants

| Mutation names | Reference | Origin | WT sequence changed for ▶ |
|---|---|---|---|
| Hypocholesterolemia | | | |
| R46L | Abifadel M<br>Nature Genet 2003 | French, US,<br>Norway, Canada | LVLALRSEEDG▶ (SEQ ID NO: 39)<br>LVLALLSEEDG (SEQ ID NO: 40) |
| A68 frameshift L82X | Fasano T<br>ATVB 2007 | Italy, Sicily | TFHRCAKDPWR▶ (SEQ ID NO: 41)<br>TFHPCPRIRRGGCLAPTWWC$_{COOH}$<br>(SEQ ID NO: 42) |
| ΔR97 | Zhao Z<br>2006 | USA<br>Black population | ERTARRKLQAQA▶ (SEQ ID NO: 43)<br>ERTAR-KLQAQA (SEQ ID NO: 44) |
| G106R | Berge KE<br>ATVB 2006 | Norway | QAARRGYLTKI▶ (SEQ ID NO: 45)<br>QAARRRYLTKI (SEQ ID NO: 46) |
| Y142X | Cohen J<br>Nature genetics 2005 | USA<br>Black population | LPHVDYIEEDS▶ (SEQ ID NO: 47)<br>LPHVD$_{COOH}$ (SEQ ID NO: 48) |
| L253F | Kotowski IK<br>Am J Hum Gen 2006 | USA | RSLRVLNCQGK▶ (SEQ ID NO: 49)<br>RSLRVFNCQGK (SEQ ID NO: 50) |
| C679X | Cohen J<br>Nature Genet 2005 | USA | AVAICCRSRHL▶ (SEQ ID NO: 51)<br>AVAIC$_{COOH}$ (SEQ ID NO: 52) |
| Hypercholesterolemia | | | |
| S127R | Abidafel M<br>Nature 2003 | France | FLVKMSGDLLE▶ (SEQ ID NO: 53)<br>FLVKMRGDLLE (SEQ ID NO: 54) |
| F216L | Abidafel M<br>Nature 2003 | France | EDGTRFHPQAS▶ (SEQ ID NO: 55)<br>EDGTRLHRQAS (SEQ ID NO: 56) |
| R218S | Allard D<br>Hum Mutation 2005 | France | EDGTRFHRQASK▶ (SEQ ID NO: 57)<br>EDGTRFHSQASK (SEQ ID NO: 58) |
| D374Y | Leren TP<br>Clin Genet 2004 | Anglo-Saxon | IGASSDCSTCF▶ (SEQ ID NO: 59)<br>IGASSYCSTCF (SEQ ID NO: 60) |
| R469W | Allard D<br>Hum Mutation 2005 | Cameroun | HSGPTRMATAI▶ (SEQ ID NO: 61)<br>HSGPTWMATAI (SEQ ID NO: 62) |
| R496W | Pisciotta L<br>Atheroscl 2006 | Italy | RSGKRRGERME▶ (SEQ ID NO: 63)<br>RSGKRWGERME (SEQ ID NO: 64) |
| Other variants | | | |
| V4I | Shioji K<br>J Hum Genet 2004 | Japan | MGTVSSRRS▶ (SEQ ID NO: 65)<br>MGTISSRRS (SEQ ID NO: 66) |
| 15_16insL | Abidafel M<br>Nature 2003 | France | LPL-LLLLLLLLGPA▶ (SEQ ID NO: 67)<br>LPLLLLLLLLLLGPA (SEQ ID NO: 68) |
| 15_16insL L | Chen SN<br>J Am Coll Card 2005 | USA | LPL--LLLLLLLLGP▶ (SEQ ID NO: 69)<br>LPLLLLLLLLLLLGP (SEQ ID NO: 70) |
| R46L + A53V | | Canada | LVLALLSEEDG + (SEQ ID NO: 40)<br>EEDGLVEAPEH (SEQ ID NO: 71) |
| A53V | Abidafel M<br>Nature 2003 | France, USA,<br>Canada | EEDGLAEAPEH (SEQ ID NO: 72)<br>EEDGLVEAPEH (SEQ ID NO: 73) |
| E57K | Kotowski IK<br>Am J Hum Gen 2006 | USA | LAEAPEHGTTA▶ (SEQ ID NO: 74)<br>LAEAPKHGTTA (SEQ ID NO: 75) |
| T77I | Fasano T<br>ATVB 2007 | Italy, Sicily | WRLPGTYVVVL▶ (SEQ ID NO: 76)<br>WRLPGIYVVVLKEET (SEQ ID NO: 77) |
| V114A | Fasano T<br>ATVB 2007 | Italy, Sicily | TKILHVFHGLL▶ (SEQ ID NO: 78)<br>TKILHAFHGLL (SEQ ID NO: 79) |

TABLE 1 -continued

PCSK9 variants associated with hypocholesterolemia, hypercholesterolemia and other PCSK9 variants

| Mutation names | Reference | Origin | WT sequence changed for ▶ |
|---|---|---|---|
| N157K | Leren TP<br>Clin Genet 2004 | Norway | QSIPWNLERIT▶ (SEQ ID NO: 80)<br>QSIPWKLERIT (SEQ ID NO: 81) |
| R237W | Benjannet S<br>JBC 2004 | Canada (QC)<br>Norway | GVVSGRDAGVA▶ (SEQ ID NO: 82)<br>GVVSGWDAGVA (SEQ ID NO: 83) |
| R357H | Allard D<br>Hum Mutation 2005 | France | GTNFGRCVDLF▶ (SEQ ID NO: 84)<br>GTNFGHCVDLF (SEQ ID NO: 85) |
| H391N | Kotowski IK<br>Am J Hum Gen 2006 | USA<br>Black population | SQAAAHVAGIA▶ (SEQ ID NO: 86)<br>SQAAANVAGIA (SEQ ID NO: 87) |
| H417Q | Kotowski IK<br>Am J Hum Gen 2006 | USA | RQRLIHFSAKD▶ (SEQ ID NO: 88)<br>RQRLIQFSAKD (SEQ ID NO: 89) |
| I424V | Shioji K<br>J Hum Genet 2004 | Japan | SAKDVINEAWF▶ (SEQ ID NO: 90)<br>SAKDVVNEAWF (SEQ ID NO: 91) |
| N425S | Pisciotta L<br>Atheroscl 2006 | Italy | AQDVINEAWFP▶ (SEQ ID NO: 92)<br>AQDVISEAWFP (SEQ ID NO: 93) |
| A443T | Allard D<br>Hum Mutation 2005 | France, USA | PNLVAALPPST▶ (SEQ ID N0: 94)<br>PNLVATLPPST (SEQ ID NO: 95) |
| I474V | Abidafel M<br>Nature 2003 | Japan | RMATAIARCAP▶ (SEQ ID NO: 96)<br>RMATAVARCAP (SEQ ID NO: 97) |
| E482G | Kotowski IK<br>Am J Hum Gen 2006 | USA<br>Black population | CAPDEELLSCS▶ (SEQ ID NO: 98)<br>CAPDEGLLSCS (SEQ ID NO: 99) |
| F515L | Kotowski IK<br>Am J Hum Gen 2006 | USA<br>Black population | RAHNAFGGEGV▶ (SEQ ID NO: 100)<br>RAHNALGGEGV (SEQ ID NO: 101) |
| A522T | Fasano T<br>ATVB 2007 | Italy, Sicily | GEGVYAIARCC▶ (SEQ ID NO: 102)<br>GEGVYTIARCC (SEQ ID NO: 103) |
| H553R | Kotowski IK<br>Am J Hum Gen 2006 | USA<br>Black population | TRVHCHQQGHV▶ (SEQ ID NO: 104)<br>TRVHCRQQGHV (SEQ ID NO: 105) |
| Q554E | Kotowski IK<br>Am J Hum Gen 2006 | USA | RVHCHQQGHVL▶ (SEQ ID NO: 106)<br>RVHCHEQGHVL (SEQ ID NO: 107) |
| P616L | Fasano T<br>ATVB 2007 | Italy, Sicily | KEHGIPAPQEQ▶ (SEQ ID NO: 108)<br>KEHGILAPQEQ (SEQ ID NO: 109) |
| Q619P | Kotowski IK<br>Am J Hum Gen 2006 | USA | GIPAPQEQVTV▶ (SEQ ID NO: 110)<br>GIPAPPEQVTV (SEQ ID NO: 111) |
| E670G | Abidafel M<br>Nature 2003 | USA | GSTSEEAVTAV▶ (SEQ ID NO: 112)<br>GSTSEGAVTAV (SEQ ID NO: 113) |

Wild type and mutated PCSK9 sequences linked to hypercholesterolemia were fused to a tag V5 antigen at the C-terminus as schematically shown in FIG. 5A (Seidah et al., 2003). Western blot analyses using V5 mAb were performed with transiently transfected HEK293 cells and the expression and processing of either wild type (WT) or the indicated human PCSK9 mutants (top of the lanes) were compared. Notice the absence of the N2 degradation product in the media of HEK293 cells expressing the R218S mutant and its lower levels in the F216L mutant (arrows). In the cell lysates, the active site mutant H226A (an inactive enzyme form) remains as a zymogen (propCSK9) remaining in the ER and not secreted into the media.

Figure 5:
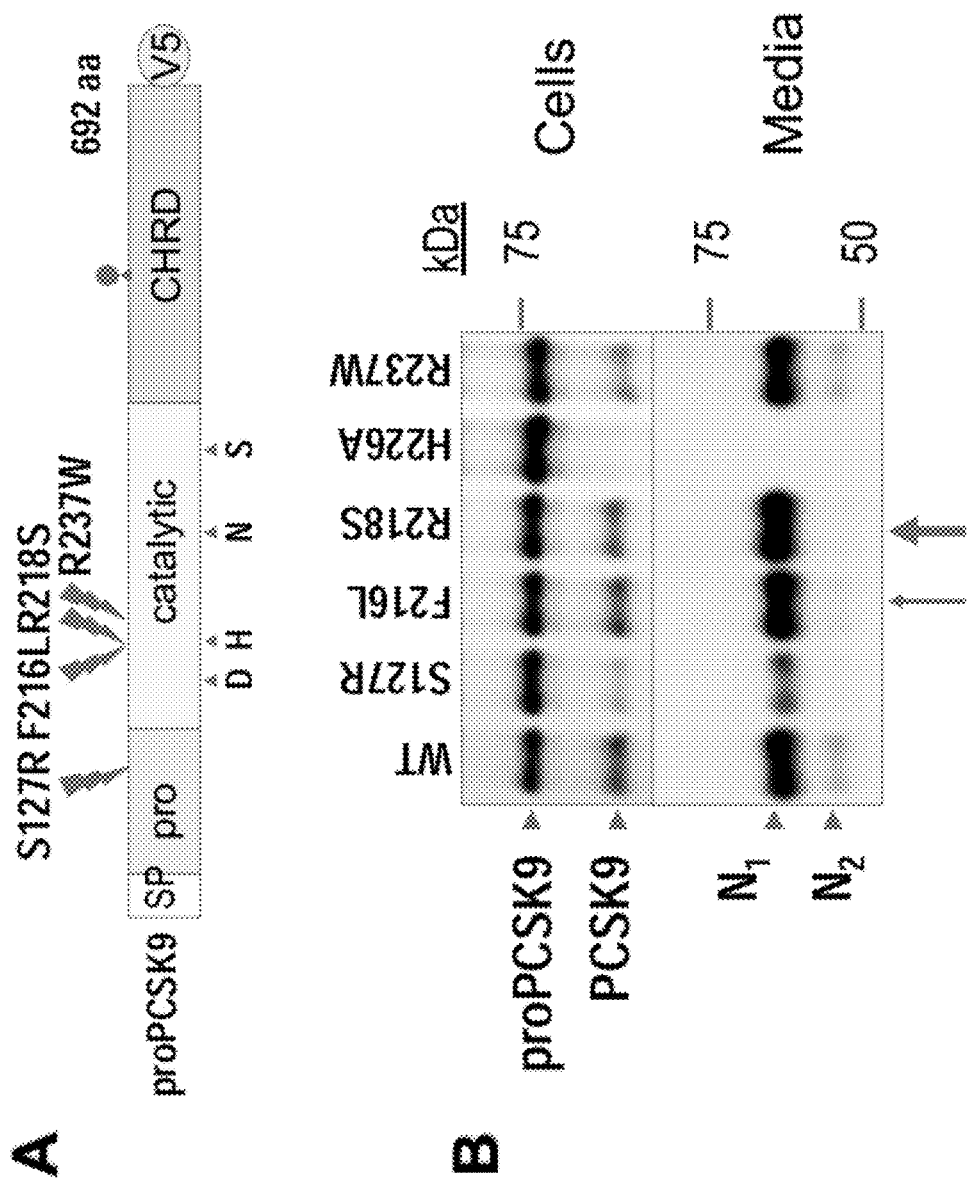
FIG. 5 shows the processing of PCSK9 and some of its mutants. In (A) the positions of the mutations along the PCSK9 sequence tagged with a V5 antigen at the C-terminus are schematically shown (Seidah et al., 2003) In (B) a Western blot analysis using V5 mAb. The expression of either wild type (WT) or the indicated human PCSK9 mutants (top of the lanes) was analysed in transiently transfected HEK293 cells. Notice the absence of the N2 degradation product in the media of HEK293 cells expressing the R218S mutant and its lower levels in the F216L mutant (arrows). In the cell lysates, the active site mutant H226A (an inactive enzyme form) remains as a zymogen (propCSK9) in the ER and is not secreted into the media.

It was observed that following signal peptidase cleavage, the endoplasmic reticulum (ER) resident zymogen propCSK9 (~75 kDa) autocatalytically cleaves its N-terminal prosegment resulting in a tight binding complex of PCSK9 and the prosegment (amino acid, aa, 31-152; ~15 kDa). The latter complex can then exit the ER and is secreted constitutively as a major full length mature ~60 kDa protein (N1) (FIG. 5, wild type, WT). However, in many cell lines was also observed the presence of an N-terminally truncated form of N1, of about ~52 kDa called N2 (FIG. 5). The loss of ~8 kDa from the N1 product occurs also in a number of natural mutants including the S127R and R237W ones, but not in the active site mutant H226A that remains in the ER as propCSK9 (FIG. 5). Interestingly, this N2 form was either not observed or significantly decreased in two natural mutants, i.e., the French mutants R218S and F216L, respectively (FIG. 5).

Sequence Alignment of the Vertebrate PCSK9

Sequence alignment of vertebrate PCSK9 showed a complete conservation of $Arg_{218}$, which in most cases is found within an R—X—X—R (SEQ ID NO: 3) or KXXXXR (SEQ ID NO: 114) sequence (FIG. 6), typical of a basic amino acid specific PC-recognition motif recognized by Furin and/or PC5-like enzymes (Seidah and Chretien, 1999). The mutation R218S would completely disrupt this motif as it eliminates the Arg in position P1, and the F216L would affect the P3 position of this motif (FIG. 6, bottom). These observations fit with the applicants' repeated inability to obtain a N-terminal sequence of N2 using Edman degradation, as the N-terminal Gln of human PCSK9 would be expected to cyclize on the sequencer and block the reaction (data not shown).

Identification of Protein Convertases that Process PCSK9

Was next tested the hypothesis that cleavage at $Arg_{218}$ is performed by one or more basic amino acid PCs. Accordingly, wild type PCSK9 was co-expressed with all the convertases as well as with β-secretase BACE1 in HEK293 cells. Cells transiently transfected with vectors expressing hPCSK9-V5 and/or the different convertases (as indicated at the top of lanes) were pulse-labeled with $^{35}$S-(Met+Cys) for 4 h and cell extracts (Cells) and media (Media) were immunoprecipitated with a V5 antibody and the precipitates were resolved by SDS/PAGE. Data revealed that only the membrane-bound Furin (but not sFurin, the soluble one, lacking the transmembrane-cytosolic tail) and to a lesser extent PC5A are capable of processing the N1 form of PCSK9 into the N2 form, with the concomitant loss of the co-immunoprecipitated PCSK9 prosegment (FIG. 7). The N-terminally truncated N2 product is thus referred to as PCSK9-$\Delta N_{218}$ (SEQ ID NO: 32) (PCSK9 lacking the first 218 amino acids; FIG. 5). In addition, co-expression of the serpin α1-PDX, which inhibits most of the basic aa-specific PCs (Anderson et al., 1993; Benjannet et al., 1997), completely inhibits such processing into PCSK9-$\Delta N_{218}$ (FIG. 7). In agreement, Furin can no longer process the R218S mutant, and cleaves to a lesser extent the F216L one (compare FIGS. 7 and 8). The R218S mutation abrogates the Furin/PC5A cleavage at the sequence $RFHR_{218}$.

Based on the crystal structure of Furin (Henrich et al., 2003) and the analysis of its many substrates (Seidah and Chretien, 1999), the best substrates of Furin would have the motif RX(R/K)R↓(E/D)L (SEQ ID NO: 115). This led the applicants to produce mutants of PCSK9 that should greatly enhance the ability of Furin to process this molecule. Thus, endogenous Furin in HEK293 cells can completely process PCSK9 at $Arg_{218}$ upon replacement of the wild type $RFHR_{218}$↓QA (SEQ ID NO: 4) sequence by an optimal Furin-recognition sequence $RRRR^{218}$↓EL (SEQ ID NO: 5), while the motifs $RFHR_{218}$↓EA (SEQ ID NO: 6) and $RFHR_{218}$↓EL (SEQ ID NO: 7) exhibited intermediate Furin-cleavability (FIG. 9). Notice the almost absence of prosegment co-immunoprecipitating with the PCSK9-ΔN218 form produced (FIG. 9), which would be predicted since such cleavage would remove the PCSK9 segment 153-218 (SEQ ID NO: 31), which contains the active site $Asp^{186}$. This would also suggest that the PCSK9-$\Delta N_{218}$ form is unable to tightly bind the prosegment, which in all PCs only binds the catalytically active convertase (Zhong et al., 1999; Nour et al., 2005; Essalmani et al., 2006).

Degradation of LDLR Cell Surface in the Presence of the PCSK9 Mutants

Earlier studies revealed that overexpression of PCSK9 results in an enhanced degradation of the LDLR in a number of cells lines and in vivo. Accordingly, the activity on the degradation of LDLR of wild type PCSK9, its R218S mutant, the $RRRR_{218}EL$ (SEQ ID NO: 5) variant, the active site mutant H226A and the Cys/His-rich domain of PCSK9 (aa 454-692 CHRD) was analyzed by Western blots in HuH7 cells (Benjannet et al., 2004) (FIG. 10). Results revealed that only wild type PCSK9 and its R218S mutant are active in enhancing the degradation of the LDLR, as compared to the pIRES control empty vector, while the $RRRR^{218}EL$ (SEQ ID NO: 5) variant and the CHRD form are inactive, as is the active site mutant H226A (FIG. 10). Thus, PCSK9-$\Delta N_{218}$ is an inactive form of PCSK9 that is secreted from cells, as compared to the active site mutant $His_{226}$, which results in an uncleaved zymogen propCSK9 that remains in the ER. Thus, the $RRRR^{218}EL$ (SEQ ID NO: 5) variant of PCSK9 provides an ideal control for the activity of PCSK9 in the secretory pathway, as opposed to active site mutants that can no longer exit from the ER and hence do not co-traffic with the LDLR to the cell surface/endosomes.

Novel Members of the PCSK9 Pathway

The cleavage of PCSK9 by Furin and/or PC5A provides a rationale behind the hypercholesterolemia phenotype associated with the French (F216L and R218S) mutations and hypocholesterolemia phenotype in Black African Americans associated with L253F mutation (results not shown) (Abifadel et al., 2003; Allard et al., 2005). Thus, PCSK9 processing by other PCs is a novel mechanism regulating the level of the active form of the enzyme, and may represent a general mechanism behind other mutations resulting in either hypercholesterolemia (loss of cleavage) or hypocholesterolemia (gain of cleavage) (Table 1 above). This does not exclude the possibility that other mechanisms may be responsible for the phenotypes behind other mutations, such as cellular sorting, post-translational modifications and zymogen activation, etc. This information provides powerful tools for the design of potent cell-based assays that incorporate PCSK9 variants with enhanced cellular activities. This information also allows the identification of novel targets (e.g. PC5A, Furin) in the PCSK9 regulatory pathway.

Circulating Forms of PCSK9 in Human Plasma

To substantiate the physiological relevance of the ex vivo observation of the cleavage of human PCSK9 by furin/PC5 into secretable PCSK9-$\Delta N_{218}$, the forms of PCSK9 that are found in the normal plasma of two individuals, one female and one male, as well as in a lipoprotein-deficient serum prepared from a commercial pool of normal human plasma (Bioreclamation Inc.), were characterized. An in-house human antibody (Ab1-hPC9) obtained from rabbits injected with affinity-purified pro-PCSK9 (aa 31-454) (SEQ ID NO: 126) expressed in *Escherichia coli* BL21 was selected for immunoprecipitation, followed by Western blotting analysis.

One-hundred microliters of plasma were immunoprecipitated with Ab1-hPC9 (1:200) or preimmune rabbit serum (PI). Immunoprecipitates were separated by SDS-PAGE on 8% glycine gels. Following transfer to a polyvinylidene difluoride membrane, PCSK9 forms were detected with the same antibody (1:3000) followed by rabbit TrueBlot™ (eBioscience) as a secondary antibody according to the manufacturer's instructions. Affinity removal of IgGs and albumin from plasma was performed using a ProteoSeek™ removal kit (Pierce). Media from HEK293 cells transfected with R218S or $RRRR_{218}EL$ (SEQ ID NO: 5) were immunoprecipitated and loaded as markers of PCSK9 forms.

The data presented in FIG. 20 shows that, in all cases, PCSK9 and its PCSK9-$\Delta N_{218}$ product are both circulating in male and female plasma. The ratio between these two circulating forms varies between individuals. Furthermore, a similar result was obtained with the commercial pooled human sera. Furin/PC5 processing of PCSK9 is thus physiological.

The level of active form of PCSK9 as well as the ratio between the active and furin/PC5-cleaved forms present in plasma collected from patients with PCSK9-associated diseases are measured by known techniques such as an enzyme-linked immunosorbant assay (ELISA), immunoprecipitation followed by Western blotting and quantitative mass spectrometry. The in-house polyclonal human antibody (Ab1-hPC9) recognizes both active full-length and cleaved forms, whereas the in house monoclonal antibody only recognizes the furin/PC5-cleaved C-terminal PCSK9 form. An antibody that specifically binds to the active full-length can be produced by using the 153-218 (SEQ ID NO: 31) fragment as antigen (or any species equivalent e.g. monkey 153-218, etc.). The combined use of both antibodies, in ELISA for example, allows the determination of the full-length to furin/PC5-cleaved PCSK9 forms ratio. The furin/PC5-cleaved PCSK9 form was measured to represent from 10 to 20% of total PCSK9 forms in a normal sample. These measurements are used as a diagnostic tool for the tailor-made therapeutic approach applicable to each patient. For example, a high ratio of full-length to furin/PC5-cleaved PCSK9 forms is indicative of a predisposition to hypercholesterolemia. A high ratio of full-length to furin/PC5-cleaved PCSK9 forms is also indicative of a need for a treatment targeting the PCSK9 activity. Such treatment for reducing the level of circulating LDL-cholesterol could combine, for example, statins and PCSK9-inhibitors. Variation of the ratio is also indicative of the presence of a PCSK9 variant (e.g., R218S or D374Y), or the presence of a PCSK9 upstream regulator variant (e.g. furin/PC5), or of others factors such as a specific diet, or treatment with statin.

These measurements could also be used to compare the PCSK9 profiles of different cohorts, for example, cohorts of patients treated with statins, cohorts of hypercholesterolemic and hypocholesterolemic patients as well as those that are resistant to various lipid lowering treatments or other PCSK9-associated diseases.

The present invention provides a method of measuring the ratio between full-length active PCSK9 form and its inactive PCSK9-$\Delta N_{218}$ product in the plasma and the use of such measurement as a diagnostic tool in PCSK9-associated diseases. Commercially available antibodies include rabbit anti-human PCSK9-(490-502) pAb (Cayman Chemical, catalog no. 10007185) which recognizes pro-PCSK9 and PCSK9-N218 but not full-length active form of PCSK9 (amino acids 153-692) and goat anti-human PCSK9 (679-692) (Imgenex, catalog no IMX-3786) antibodies. Taking into account the slightly higher molecular mass of V5-tagged PCSK9 compared with untagged PCSK9, it was possible to show that the plasma forms co-migrated with markers obtained from the medium of HEK293 cells overexpressing the uncleavable R218S or fully processed RRRR$_{218}$EL (SEQ ID NO: 5) variant (FIG. 20)).

EXAMPLE 2

Enhanced Cellular PCSK9 Activities and the Identification of Novel Cell Surface Detector Molecules Cells which express a PCSK9 with increased cellular activities, as measured by a very low to undetectable level of LDLR at the cell surface, could be used to identify novel cell surface molecules that, similarly to LDLR, are also sensitive to the presence of the PCSK9.

While LRP was found not to be affected by PCSK9 (Benjannet et al., 2004), the present invention shows that VLDLR and ApoER2 (FIGS. 11 and 12), are degraded by PCSK9 (FIGS. 13 and 14). [PCSK9-TM-CT (Lamp1)] (SEQ ID NO: 24) was selected as the chimera that results in the highest efficacy of degradation of either LDLR, VLDLR or ApoER2.

A stable transfectant pool of [PCSK9-TM-CT (Lamp1)] was obtained in HuH7 cells that were resistant to G418. These cells were then FACS-selected for clones with the lowest levels of endogenous cell-surface LDLR. These cells form the basis for the proteomics and genomics analysis for the discovery of PCSK9-related functions.

EXAMPLE 3

Cell-Based Assay for the Inhibition of PCSK9

Stable clones expressing [PCSK9-TM-CT (Lamp1)] (SEQ ID NO: 24) formed the basis for a cell-based assay for the HTS analysis for the discovery of PCSK9-inhibitory/silencing compounds.

The sequence of PCSK9 in the chimera could contain the human full-length (SEQ ID NO: 21) or any sequence satisfying the consensus derived from the human, mice, rat and monkey PCSK9 or alternatively variants of PCSK9 identified as conferring to PCSK9 resistance to cleavage by other enzymes, e.g., the R218S mutation (FIG. 8), thereby resulting in an increased PCSK9 activity due to its lower degradation.

LDLR read out may be used in HuH7 cells or any cell type of interest. The protein level of the LDLR at the cell surface is extremely low as verified by FACS analysis. Upon HTS screening, the increased level of LDLR at the cell surface was measured using either a fluorescent or HRP-tagged antibody to LDLR, or using a fluorescent ligand such as Dil-LDL (FIG. 15). However, HuH7 cells stably expressing low levels of ApoER2 or VLDLR are also obtained as alternative assays for PCSK9 activity and the selection for appropriate inhibitors. These assays could also incorporate multiple read-outs, namely LDLR, VLDLR or ApoER2 (each measured with specific antibodies linked to different fluorochromes, e.g., green, magenta and red fluorescent moieties).

EXAMPLE 4

High Throughput Screening for PCSK9 Inhibitors

Candidate inhibitors are screened on the cell assays of the present invention. Compounds showing statistically significant activity in both replicates are selected as hit compounds. Hit compounds are be verified by LC mass spectrometry and 10-point titrations are performed in triplicate on each compound to determine IC50 values (concentration of 50% inhibition). In addition to the screening process itself, expression and purification of a modulated candidate convertases for in vitro assays, assay adaptation, and Quantitative Structure-Activity Relationship (QSAR) studies on hits are performed. Particularly, inhibitors with Kis in the nanomolar range are sought. In vitro and ex vivo validation of the lead compounds will confirm their inhibitory potency and effects.

EXAMPLE 5

Multiplexed Positive Cell-Based Assays for PCSK9 Inhibitors Combined with a CELISA While inhibitors of the function of PCSK9 would reflect a blockage at some point of the PCSK9 pathway, they do not necessarily represent catalytic inhibitors. For this purpose, the present invention encompasses incorporating in the cell-based assay in addition to the PCSK9 chimera (e.g., R218S-PCSK9-[TM-CT]), another bait-specific chimera that expresses a cell-surface protein containing a PCSK9 recognition processing sequence (e.g., SSVFAQSIPWN (SEQ ID NO: 117)) (such as that described in co-pending WO 2007/030937 filed Sep. 14, 2006). The bait-specific cells surface protein contains the following configurations: [signal peptide]-[HA tag]-[Bait region of PCSK9, e.g., SSVFAQSIPWN (SEQ ID NO: 117)]-[Fc portion of human immunoglobulin]-[TM-CT (ACE2)]. This allows a better evaluation of the effect of the selected compounds on the enzymatic activity of PCSK9 itself within a cellular context.

The chimera expressing a bait specific for PCSK9 (SSVFAQSIPWN (SEQ ID NO: 117) or a longer form) is stably transfected into cells expressing PCSK9-[TM-CT-Lamp1] (SEQ ID NO: 24). FACS-selected stable pools of HuH7 cells that do not present LDLR at the surface are selected. The absence or very low amount of LDLR could also be tested with fluorogenic LDLR ligand (DiI-LDL) or using of a monoclonal antibody to LDLR. Inhibitors of PCSK9 catalytic activity affect the appearance of the HA tag from the bait-specific chimera at the cell surface. The detection in parallel of both HA and LDLR at the cell surface could be performed using a variety of assays including CELISA assays (such as described in co-pending WO 2007/030937 filed Sep. 14, 2006) and the use of a fluorogenic LDLR ligand or mAB to LDLR coupled to a chemiluminescent probe (FIG. 15). Screening is performed to identify compounds associated to high levels of the HA tag and the LDLR at the cell surface.

EXAMPLE 6

Optimization of Leads

Once inhibitor "leads" are identified, they will be further characterized for affinity, mode of inhibition and specificity using in vitro assays and purified PC enzymes.

EXAMPLE 7

Validation of Novel PCSK9-Associated Pathways Using an Animal Model

A transgenic mice specifically overexpressing PCSK9 in hepatocytes was generated. The transgene was under the control of the ApoE promoter and enhancer regulation. The mice were seemingly healthy, however their circulating LDL-Cholesterol was quite elevated. Transgenic expression of PCSK9 in mouse liver resulted in a line that expressed 40 fold higher PCSK9 than the endogenous enzyme in hepatocytes (result not shown). The transgenic protein was tagged with a V5 at its c-terminus to differentiate it from the endogenous one. Analysis of mouse plasma samples revealed that PCSK9-V5 is secreted in blood and is partially processed by Furin/PC5-like enzymes to generate PCSK9-$\Delta N_{218}$ as observed in cells and in human plasma. Immunofluorescence and Confocal Microscopy analyses of the skeletal mouse muscles were performed using a rabbit polyclonal Ab:VLDLR (a74; 1:200). Immunofluorescence analyses were performed with a Zeiss™ LSM-510 confocal microscope. Confocal immunofluorescence microscopy was performed with a Nikon Eclipse™ TE2000-U laser-scanning microscope with 408, 488, and 543-nm laser lines. Images were processed with Adobe Photoshop™ CS2, version 9.0 (Adobe Systems). Interestingly, analysis of VLDLR levels in the muscle of transgenic mice versus non-transgenic control littermates (PCSK9$^{+/+}$; PCSK9$^{-/-}$) revealed that the level of VLDR is dramatically decreased in these mice (right panel, FIG. 21). In contrast, the level of VLDLR in PCSK9-knockout mice is dramatically increased compared to the control mice (middle panel, FIG. 21). This is the first evidence that circulating PCSK9 can enhance the degradation of VLDLR in vivo. The decrease level of VLDLR in the transgenic mice overexpressing PCSK9 in the liver was also confirm by immunodetection of PCSK9 in extracts of skeletal muscle (see FIG. 21).

The present invention allow the identification of novel PCSK9-associated pathways and identify PCSK9 as a potential target in these pathways-associated diseases (e.g. in the VLDLR-associated diseases).

Although the present invention has been described hereinabove by way of specific embodiments thereof, it can be modified, without departing from the spirit and nature of the subject invention as defined in the appended claims.

REFERENCES

1. Abifadel, M., M. Varret, J. P. Rabes, D. Allard, K. Ouguerram, M. Devillers, C. Cruaud, S. Benjannet, L. Wickham, D. Erlich, A. Derre, L. Villeger, M. Farnier, I. Beucler, E. Bruckert, J. Chambaz, B. Chanu, J. M. Lecerf, G. Luc, P. Moulin, J. Weissenbach, A. Prat, M. Krempf, C. Junien, N. G. Seidah, and C. Boileau. 2003. Mutations in PCSK9 cause autosomal dominant hypercholesterolemia. *Nat. Genet.* 34:154-156.
2. Allard, D., S. Amsellem, M. Abifadel, M. Trillard, M. Devillers, G. Luc, M. Krempf, Y. Reznik, J. P. Girardet, A. Fredenrich, C. Junien, M. Varret, C. Boileau, P. Benlian, and J. P. Rabes. 2005. Novel mutations of the PCSK9 gene cause variable phenotype of autosomal dominant hypercholesterolemia. *Hum. Mutat.* 26:497.
3. Anderson, E. D., L. Thomas, J. S. Hayflick, and G. Thomas. 1993. Inhibition of HIV-1 gp160-dependent membrane fusion by a furin-directed alpha 1-antitrypsin variant. *J. Biol. Chem.* 268:24887-24891.
4. Attie, A. D. 2004. The mystery of PCSK9. *Arterioscler. Thromb. Vasc. Biol.* 24:1337-1339.
5. Attie, A. D. and N. G. Seidah. 2005. Dual regulation of the LDL receptor—some clarity and new questions. *Cell Metab* 1:290-292.
6. Bagshaw, R. D., D. J. Mahuran, and J. W. Callahan. 2005. A proteomic analysis of lysosomal integral membrane proteins reveals the diverse composition of the organelle. *Mol. Cell Proteomics* 4:133-143.
7. Belkhiri, A., V. Lytvyn, C. Guilbault, L. Bourget, B. Massie, D. K. Nagler, and R. Menard. 2002. A noninvasive cell-based assay for monitoring proteolytic activity within a specific subcellular compartment. *Anal. Biochem.* 306:237-246.
8. Benjannet, S., A. Elagoz, L. Wickham, M. Mamarbachi, J. S. Munzer, A. Basak, C. Lazure, J. A. Cromlish, S. Sisodia, F. Checker, M. Chretien, and N. G. Seidah. 2001. Post-translational processing of beta-secretase (beta-amyloid-converting enzyme) and its ectodomain shedding. The pro- and transmembrane/cytosolic domains affect its cellular activity and amyloid-beta production. *J. Biol. Chem.* 276:10879-10887.
9. Benjannet, S., D. Rhainds, R. Essalmani, J. Mayne, L. Wickham, W. Jin, M. C. Asselin, J. Hamelin, M. Varret, D. Allard, M. Trillard, M. Abifadel, A. Tebon, A. D. Attie, D. J. Rader, C. Boileau, L. Brissette, M. Chretien, A. Prat, and N. G. Seidah. 2004. NARC-1/PCSK9 and its natural mutants: zymogen cleavage and effects on the low density lipoprotein (LDL) receptor and LDL cholesterol. *J. Biol. Chem.* 279:48865-48875.

10. Benjannet, S., D. Savaria, A. Laslop, J. S. Munzer, M. Chretien, M. Marcinkiewicz, and N. G. Seidah. 1997. Alpha1-antitrypsin Portland inhibits processing of precursors mediated by proprotein convertases primarily within the constitutive secretory pathway. *J. Biol. Chem.* 272: 26210-26218.

11. Berge, K. E., L. Ose, and T. P. Leren. 2006. Missense Mutations in the PCSK9 Gene Are Associated With Hypocholesterolemia and Possibly Increased Response to Statin Therapy. *Arterioscler. Thromb. Vasc. Biol.*

12. Bergeron, E., M. J. Vincent, L. Wickham, J. Hamelin, A. Basak, S. T. Nichol, M. Chretien, and N. G. Seidah. 2005. Implication of proprotein convertases in the processing and spread of severe acute respiratory syndrome coronavirus. *Biochem. Biophys. Res. Commun.* 326:554-563.

13. Boycott, K. M.; Flavelle, S.; Bureau, A.; Glass, H. C.; Fujiwara, T. M.; Wirrell, E.; Davey, K.; Chudley, A. E.; Scott, J. N.; McLeod, D. R.; Parboosingh, J. S. 2005: Homozygous deletion of the very low density lipoprotein receptor gene causes autosomal recessive cerebellar hypoplasia with cerebral gyral simplification. *Am. J. Hum. Genet.* 77: 477-483.

14. Cheng, D., P. J. Espenshade, C. A. Slaughter, J. C. Jaen, M. S. Brown, and J. L. Goldstein. 1999. Secreted site-1 protease cleaves peptides corresponding to luminal loop of sterol regulatory element-binding proteins. *J. Biol. Chem.* 274:22805-22812.

15. Choo K H, Tan T W, Ranganathan S. 2005. SPdb—a signal peptide database. BMC Bioinformatics 6:249

16. Cohen, J., A. Pertsemlidis, I. K. Kotowski, R. Graham, C. K. Garcia, and H. H. Hobbs. 2005. Low LDL cholesterol in individuals of African descent resulting from frequent nonsense mutations in PCSK9. *Nat. Genet.* 37:161-165.

17. Conesa, M., A. Prat, J. S. Mort, J. Marvaldi, J. C. Lissitzky, and N. G. Seidah. 2003. Down-regulation of alphav/beta3 integrin via misrouting to lysosomes by overexpression of a beta3Lamp1 fusion protein. *Biochem. J.* 370:703-711.

18. Decroly, E., S. Wouters, C. Di Bello, C. Lazure, J. M. Ruysschaert, and N. G. Seidah. 1996. Identification of the paired basic convertases implicated in HIV gp160 processing based on in vitro assays and expression in CD4(+) cell lines. *J Biol. Chem.* 271:30442-30450.

19. Dubuc, G., A. Chamberland, H. Wassef, J. Davignon, N. G. Seidah, L. Bernier, and A. Prat. 2004. Statins upregulate PCSK9, the gene encoding the proprotein convertase neural apoptosis-regulated convertase-1 implicated in familial hypercholesterolemia. *Arterioscler. Thromb. Vasc. Biol.* 24:1454-1459.

20. Essalmani, R., J. Hamelin, J. Marcinkiewicz, A. Chamberland, M. Mbikay, M. Chretien, N. G. Seidah, and A. Prat. 2006. Deletion of the gene encoding proprotein convertase 5/6 causes early embryonic lethality in the mouse. *Mol. Cell Biol.* 26:354-361.

21. Fasano T, Cefalu A B, Di Leo E, Noto D, Pollaccia D, Bocchi L, Valenti V, Bonardi R, Guardamagna O, Averna M, Tarugi P. 2007. A novel loss of function mutation of PCSK9 gene in white subjects with low-plasma low-density lipoprotein cholesterol. *Arterioscler Thromb Vasc Biol.* 27:677-81.

22. Fatemi, S. H. 2005. Reelin glycoprotein in autism and schizophrenia. *Int. Rev. Neurobiol.* 71:179-187.

23. Goding, Monoclonal Antibodies: Principles and Practice, pp. 59-103 (Academic Press, 1986)

24. Goudriaan J R, Tacken P J, Dahlmans V E, Gijbels M J, van Dijk K W, Havekes L M, Jong M C. 2001. Protection from obesity in mice lacking the VLDL receptor. Arterioscler Thromb Vasc Biol. 9:1488-93.

25. Henrich, S., A. Cameron, G. P. Bourenkov, R. Kiefersauer, R. Huber, I. Lindberg, W. Bode, and M. E. Than. 2003. The crystal structure of the proprotein processing proteinase furin explains its stringent specificity. *Nat. Struct. Biol.* 10:520-526.

26. Hofmann K. and Stoffel W. 1993. TMBASE—A database of membrane spanning protein segments Biol. Chem. Hoppe-Seyler 374, 166.

27. Horton, J. D., N. A. Shah, J. A. Warrington, N. N. Anderson, S. W. Park, M. S. Brown, and J. L. Goldstein. 2003. Combined analysis of oligonucleotide microarray data from transgenic and knockout mice identifies direct SREBP target genes. *Proc. Natl. Acad. Sci. U.S.A* 100:12027-12032.

28. Jadot, M., W. M. Canfield, W. Gregory, and S. Kornfeld. 1992. Characterization of the signal for rapid internalization of the bovine mannose 6-phosphate/insulin-like growth factor-II receptor. *J Biol. Chem.* 267:11069-11077.

29. Jin, W., I. V. Fuki, N. G. Seidah, S. Benjannet, J. M. Glick, and D. J. Rader. 2005. Proprotein covertases are responsible for proteolysis and inactivation of endothelial lipase. *J Biol. Chem.* 280:36551-36559.

30. Kohler et al., Nature, 256: 495 (1975).

31. Kotowski, I. K., A. Pertsemlidis, A. Luke, R. S. Cooper, G. L. Vega, J. C. Cohen, and H. H. Hobbs. 2006. A Spectrum of PCSK9 Alleles Contributes to Plasma Levels of Low-Density Lipoprotein Cholesterol. *Am. J. Hum. Genet.* 78:410-422.

32. Laird, F. M., H. Cai, A. V. Savonenko, M. H. Farah, K. He, T. Melnikova, H. Wen, H. C. Chiang, G. Xu, V. E. Koliatsos, D. R. Borchelt, D. L. Price, H. K. Lee, and P. C. Wong. 2005. BACE1, a major determinant of selective vulnerability of the brain to amyloid-beta amyloidogenesis, is essential for cognitive, emotional, and synaptic functions. *J Neurosci.* 25:11693-11709.

33. Lalanne, F., G. Lambert, M. J. Amar, M. Chemveaux, Y. Zair, A. L. Jarnoux, K. Ouguerram, J. Friburg, N. G. Seidah, H. B. Brewer, Jr., M. Krempf, and P. Costet. 2005. Wild-type PCSK9 inhibits LDL clearance but does not affect apoB-containing lipoprotein production in mouse and cultured cells. *J. Lipid Res.* 46:1312-1319.

34. Leren, T. P. 2004. Mutations in the PCSK9 gene in Norwegian subjects with autosomal dominant hypercholesterolemia. *Clin. Genet.* 65:419-422.

35. Lindenbaum, et al., Nucleic Acids Research 32 (21):0177 (2004)

36. Maxwell, K. N. and J. L. Breslow. 2004. Adenoviral-mediated expression of Pcsk9 in mice results in a low-density lipoprotein receptor knockout phenotype. *Proc. Natl. Acad. Sci. U.S.A* 101:7100-7105.

37. Maxwell, K. N., E. A. Fisher, and J. L. Breslow. 2005. Overexpression of PCSK9 accelerates the degradation of the LDLR in a post-endoplasmic reticulum compartment. *Proc. Natl. Acad. Sci. U.S.A* 102:2069-2074.

38. Maxwell, K. N., R. E. Soccio, E. M. Duncan, E. Sehayek, and J. L. Breslow. 2003. Novel putative SREBP and LXR target genes identified by microarray analysis in liver of cholesterol-fed mice. *J. Lipid Res.* 44:2109-2119.

39. Naoumova, R. P., I. Tosi, D. Patel, C. Neuwirth, S. D. Horswell, A. D. Marais, C. van Heyningen, and A. K. Soutar. 2005. Severe hypercholesterolemia in four British families with the D374Y mutation in the PCSK9 gene: long-term follow-up and treatment response. *Arterioscler. Thromb. Vasc. Biol.* 25:2654-2660.

40. Naureckiene, S., L. Ma, K. Sreekumar, U. Purandare, C. F. Lo, Y. Huang, L. W. Chiang, J. M. Grenier, B. A. Ozenberger, J. S. Jacobsen, J. D. Kennedy, P. S. DiStefano, A. Wood, and B. Bingham. 2003. Functional characterization of Narc 1, a novel proteinase related to proteinase K. *Arch. Biochem. Biophys.* 420:55-67.

41. Nour, N., A. Basak, M. Chretien, and N. G. Seidah. 2003. Structure-Function Analysis of the Prosegment of the Proprotein Convertase PC5A. *J. Biol. Chem.* 278:2886-2895.

42. Nour, N., G. Mayer, J. S. Mort, A. Salvas, M. Mbikay, C. J. Morrison, C. M. Overall, and N. G. Seidah. 2005. The Cysteine-rich Domain of the Secreted Proprotein Convertases PC5A and PACE4 Functions as a Cell Surface Anchor and Interacts with Tissue Inhibitors of Metalloproteinases. *Mol. Biol. Cell* 16:5215-5226.

43. Park, S. W., Y. A. Moon, and J. D. Horton. 2004. Post-transcriptional regulation of low density lipoprotein receptor protein by proprotein convertase subtilisin/kexin type 9a in mouse liver. *J. Biol. Chem.* 279:50630-50638.

44. Pisciotta, L., C. P. Oliva, A. B. Cefalu, D. Noto, A. Bellocchio, R. Fresa, A. Cantafora, D. Patel, M. Averna, P. Tarugi, S. Calandra, and S. Bertolini. 2005. Additive effect of mutations in LDLR and PCSK9 genes on the phenotype of familial hypercholesterolemia. *Atherosclerosis.*

45. Pisciotta L, Priore Oliva C, Cefalu A B, Noto D, Bellocchio A, Fresa R, Cantafora A, Patel D, Averna M, Tarugi P, Calandra S, Bertolini S. 2006. Additive effect of mutations in LDLR and PCSK9 genes on the phenotype of familial hypercholesterolemia. *Atherosclerosis.* 186:433-40.

46. Pullikotil, P., M. Vincent, S. T. Nichol, and N. G. Seidah. 2004. Development of protein-based inhibitors of the proprotein of convertase SKI-1/S1P: processing of SREBP-2, ATF6, and a viral glycoprotein. *J. Biol. Chem.* 279:17338-17347.

47. Rashid, S., D. E. Curtis, R. Garuti, N. N. Anderson, Y. Bashmakov, Y. K. Ho, R. E. Hammer, Y. A. Moon, and J. D. Horton. 2005. Decreased plasma cholesterol and hypersensitivity to statins in mice lacking Pcsk9. *Proc. Natl. Acad. Sci. U.S.A* 102:5374-5379.

48. Seidah, N. G., S. Benjannet, L. Wickham, J. Marcinkiewicz, S. B. Jasmin, S. Stifani, A. Basak, A. Prat, and M. Chretien. 2003. The secretory proprotein convertase neural apoptosis-regulated convertase 1 (NARC-1): liver regeneration and neuronal differentiation. *Proc. Natl. Acad. Sci. U.S.A* 100:928-933.

49. Seidah, N. G. and M. Chretien. 1999. Proprotein and prohormone convertases: a family of subtilases generating diverse bioactive polypeptides. *Brain Res.* 848:45-62.

50. Seidah, N. G., A. M. Khatib, and A. Prat. The proprotein convertases and their implication in sterol and/or lipid metabolism. Biological Chemistry (in press). 2006.

51. Seidah, N. G., S. J. Mowla, J. Hamelin, A. M. Mamarbachi, S. Benjannet, B. B. Toure, A. Basak, J. S. Munzer, J. Marcinkiewicz, M. Zhong, J. C. Barale, C. Lazure, R. A. Murphy, M. Chretien, and M. Marcinkiewicz. 1999. Mammalian subtilisin/kexin isozyme SKI-1: A widely expressed proprotein convertase with a unique cleavage specificity and cellular localization. *Proc. Natl. Acad. Sci. U.S.A* 96:1321-1326.

52. Seidah, N. G. and A. Prat. 2002. Precursor convertases in the secretory pathway, cytosol and extracellular milieu. *Essays Biochem.* 38:79-94.

53. Thomas, G. 2002. Furin at the cutting edge: from protein traffic to embryogenesis and disease. *Nat. Rev. Mol. Cell Biol.* 3:753-766.

54. Timms, K. M., S. Wagner, M. E. Samuels, K. Forbey, H. Goldfine, S. Jammulapati, M. H. Skolnick, P. N. Hopkins, S. C. Hunt, and D. M. Shattuck. 2004. A mutation in PCSK9 causing autosomal-dominant hypercholesterolemia in a Utah pedigree. *Hum. Genet.* 114:349-353.

55. Vincent, M. J., E. Bergeron, S. Benjannet, B. R. Erickson, P. E. Rollin, T. G. Ksiazek, N. G. Seidah, and S. T. Nichol. 2005. Chloroquine is a potent inhibitor of SARS coronavirus infection and spread. *Virol. J* 2:69.

56. Wang, L.; Wang, X.; Laird, N.; Zuckerman, B.; Stubblefield, P.; Xu, X. 2006: Polymorphism in maternal LRP8 gene is associated with fetal growth. *Am. J. Hum. Genet.* 78: 770-777.

57. Zhao Z, Tuakli-Wosornu Y, Lagace T A, Kinch L, Grishin N V, Horton J D, Cohen J C, Hobbs H H. 2006. Molecular characterization of loss-of-function mutations in PCSK9 and identification of a compound heterozygote. *Am J Hum Genet.* 79:514-23.

58. Zhong, M., J. S. Munzer, A. Basak, S. Benjannet, S. J. Mowla, E. Decroly, M. Chretien, and N. G. Seidah. 1999. The prosegments of furin and PC7 as potent inhibitors of proprotein convertases. In vitro and ex vivo assessment of their efficacy and selectivity. *J. Biol. Chem.* 274:33913-33920.

The invention claimed is:

1. A purified polypeptide, the amino acid sequence of which consists of SEQ ID NO: 32.

\* \* \* \* \*

SEQUENCE LISTING

<160> NUMBER OF SEQ ID NOS: 126

<210> SEQ ID NO 1
<211> LENGTH: 4
<212> TYPE: PRT
<213> ORGANISM: Homo sapiens

<400> SEQUENCE: 1

Lys Asp Glu Leu
1

<210> SEQ ID NO 2
<211> LENGTH: 4
<212> TYPE: PRT
<213> ORGANISM: Artificial sequence
<220> FEATURE:
<223> OTHER INFORMATION: Synthetic Construct

```
<400> SEQUENCE: 2

Tyr Ala Ser Ile
1

<210> SEQ ID NO 3
<211> LENGTH: 4
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 3

Arg Xaa Xaa Arg
1

<210> SEQ ID NO 4
<211> LENGTH: 6
<212> TYPE: PRT
<213> ORGANISM: Artificial sequence
<220> FEATURE:
<223> OTHER INFORMATION: Synthetic Construct

<400> SEQUENCE: 4

Arg Phe His Arg Gln Ala
1               5

<210> SEQ ID NO 5
<211> LENGTH: 6
<212> TYPE: PRT
<213> ORGANISM: Artificial sequence
<220> FEATURE:
<223> OTHER INFORMATION: Synthetic Construct

<400> SEQUENCE: 5

Arg Arg Arg Arg Glu Leu
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic Construct

<400> SEQUENCE: 6

Arg Phe His Arg Glu Ala
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic Construct

<400> SEQUENCE: 7

Arg Phe His Arg Glu Leu
1               5

<210> SEQ ID NO 8
<211> LENGTH: 10
<212> TYPE: PRT
<213> ORGANISM: Artificial sequence
<220> FEATURE:
```

<223> OTHER INFORMATION: Synthetic Construct

<400> SEQUENCE: 8

Cys Pro Ser Asp Ser Glu Glu Asp Glu Gly
1               5                   10

<210> SEQ ID NO 9
<211> LENGTH: 4
<212> TYPE: PRT
<213> ORGANISM: Artificial sequence
<220> FEATURE:
<223> OTHER INFORMATION: Synthetic Construct

<400> SEQUENCE: 9

Tyr Lys Gly Leu
1

<210> SEQ ID NO 10
<211> LENGTH: 12
<212> TYPE: PRT
<213> ORGANISM: Homo sapiens

<400> SEQUENCE: 10

Glu Asp Gly Thr Arg Phe His Arg Gln Ala Ser Lys
1               5                   10

<210> SEQ ID NO 11
<211> LENGTH: 12
<212> TYPE: PRT
<213> ORGANISM: Danio rerio

<400> SEQUENCE: 11

Glu Asp Gly Thr Arg Val His Arg Gln Ala Ser Gln
1               5                   10

<210> SEQ ID NO 12
<211> LENGTH: 12
<212> TYPE: PRT
<213> ORGANISM: Gallus gallus

<400> SEQUENCE: 12

Glu Asp Ser Ser Arg Phe His Arg Gln Ala Ser Lys
1               5                   10

<210> SEQ ID NO 13
<211> LENGTH: 12
<212> TYPE: PRT
<213> ORGANISM: Tetraodon fluviatilis

<400> SEQUENCE: 13

Val Gly Glu Ala Gly Gly His Arg Glu Ala Ser Arg
1               5                   10

<210> SEQ ID NO 14
<211> LENGTH: 12
<212> TYPE: PRT
<213> ORGANISM: Fugu rubripes

<400> SEQUENCE: 14

Val Glu Lys Gly Gly Gly His Arg Glu Ala Ser Arg
1               5                   10

<210> SEQ ID NO 15
<211> LENGTH: 12
<212> TYPE: PRT
<213> ORGANISM: Homo sapiens

<400> SEQUENCE: 15

Glu Asp Gly Thr Arg Leu His Arg Gln Ala Ser Lys
1               5                   10

<210> SEQ ID NO 16
<211> LENGTH: 12
<212> TYPE: PRT
<213> ORGANISM: Homo sapiens

<400> SEQUENCE: 16

Glu Asp Gly Thr Arg Phe His Ser Gln Ala Ser Lys
1               5                   10

<210> SEQ ID NO 17
<211> LENGTH: 8
<212> TYPE: PRT
<213> ORGANISM: Homo sapiens

<400> SEQUENCE: 17

Gly Thr Arg Phe His Ser Gln Ala
1               5

<210> SEQ ID NO 18
<211> LENGTH: 8
<212> TYPE: PRT
<213> ORGANISM: Homo sapiens

<400> SEQUENCE: 18

Gly Thr Arg Leu His Arg Gln Ala
1               5

<210> SEQ ID NO 19
<211> LENGTH: 2325
<212> TYPE: DNA
<213> ORGANISM: Artificial sequence
<220> FEATURE:
<223> OTHER INFORMATION: Synthetic Construct

<400> SEQUENCE: 19

| | | | | | |
|---|---|---|---|---|---|
| atgggcaccg | tcagctccag | gcggtcctgg | tggccgctgc | cactgctgct | gctgctgctg | 60 |
| ctgctcctgg | gtcccgcggg | cgcccgtgcg | caggaggacg | aggacggcga | ctacgaggag | 120 |
| ctggtgctag | ccttgcgttc | cgaggaggac | ggcctggccg | aagcacccga | gcacggaacc | 180 |
| acagccacct | tccaccgctg | cgccaaggat | ccgtggaggt | tgcctggcac | ctacgtggtg | 240 |
| gtgctgaagg | aggagaccca | cctctcgcag | tcagagcgca | ctgcccgccg | cctgcaggcc | 300 |
| caggctgccc | gccggggata | cctcaccaag | atcctgcatg | tcttccatgg | ccttcttcct | 360 |
| ggcttcctgg | tgaagatgag | tggcgacctg | ctggagctgg | ccttgaagtt | gccccatgtc | 420 |
| gactacatcg | aggaggactc | ctctgtcttt | gcccagagca | tccgtgtgaa | cctggagcgg | 480 |
| attacccctc | cacggtaccg | ggcggatgaa | taccagcccc | ccgacggagg | cagcctggtg | 540 |
| gaggtgtatc | tcctagacac | cagcatacag | agtgaccacc | gggaaatcga | gggcagggtc | 600 |
| atggtcaccg | acttcgagaa | tgtgcccgag | gaggacggga | cccgcttcca | cagacaggcc | 660 |
| agcaagtgtg | acagtcatgg | cacccacctg | gcaggggtgg | tcagcggccg | ggatgccggc | 720 |
| gtggccaagg | gtgccagcat | gcgcagcctg | cgcgtgctca | actgccaagg | aagggcacg | 780 |
| gttagcggca | ccctcatagg | cctggagttt | attcggaaaa | gccagctggt | ccagcctgtg | 840 |
| gggccactgg | tggtgctgct | gccccctggcg | ggtgggtaca | gccgcgtcct | caacgccgcc | 900 |
| tgccagcgcc | tggcgagggc | tggggtcgtg | ctggtcaccg | ctgccggcaa | cttccgagac | 960 |

```
gatgcctgcc tctactcccc agcctcagct cccgaggtca tcacagttgg ggccaccaat    1020
gcccaggacc agccggtgac cctggggact ttggggacca actttggccg ctgtgtggac    1080
ctctttgccc caggggagga catcattggt gcctccagcg actgcagcac ctgctttgtg    1140
tcacagagtg ggacatcaca ggctgctgcc cacgtggctg gcattgcagc catgatgctg    1200
tctgccgagc cggagctcac cctggccgag ttgaggcaga gactgatcca cttctctgcc    1260
aaagatgtca tcaatgaggc ctggttccct gaggaccagc gggtactgac ccccaacctg    1320
gtggccgccc tgcccccag cacccatggg gcaggttggc agctgttttg caggactgtg    1380
tggtcagcac actcggggcc tacacggatg gccacagcca tcgcccgctg cgccccagat    1440
gaggagctgc tgagctgctc cagtttctcc aggagtggga gcggcgggg cgagcgcatg     1500 gaggcccaag ggggcaagct ggtctgccgg gcccacaacg ctttggggg tgagggtgtc     1560 tacgccattg ccaggtgctg cctgctaccc caggccaact gcagcgtcca cacagctcca    1620
ccagctgagg ccagcatggg gacccgtgtc cactgccacc aacagggcca cgtcctcaca    1680
ggctgcagct cccactggga ggtggaggac cttggcaccc acaagccgcc tgtgctgagg    1740
ccacgaggtc agcccaacca gtgcgtgggc cacaggagg ccagcatcca cgcttcctgc     1800
tgccatgccc caggtctgga atgcaaagtc aaggagcatg gaatcccggc ccctcaggag    1860
caggtgaccg tggcctgcga ggagggctgg accctgactg gctgcagtgc cctccctggg    1920
acctcccacg tcctgggggc ctacgccgta caacacgt gtgtagtcag gagccgggac       1980
gtcagcacta caggcagcac cagcgaagag gccgtgacag ccgttgccat ctgctgccgg    2040
agccggcacc tggcgcaggc ctcccaggag ctccagaccg gtaagcctat ccctaaccct    2100
ctcctcggtc tcgattctac gggaggaata tggctgattg tttttggagt tgtgatggga    2160
gtgatagtgg ttggcattgt catcctgatc ttcactggga tcagagatcg aagaagaaa    2220 aataaagcaa gaagtggaga aaatccttat gcctccatcg atattagcaa aggagaaaat    2280
aatccaggat tccaaaacac tgatgatgtt cagacctcct tttag                    2325
```

<210> SEQ ID NO 20
<211> LENGTH: 774
<212> TYPE: PRT
<213> ORGANISM: Artificial sequence
<220> FEATURE:
<223> OTHER INFORMATION: Synthetic Construct

<400> SEQUENCE: 20

```
Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125
```

-continued

```
Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
                195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270

Lys Ser Gln Leu Val Gln Pro Val Gly Pro Leu Val Val Leu Leu Pro
            275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
                340                 345                 350

Thr Asn Phe Gly Arg Cys Val Asp Leu Phe Ala Pro Gly Glu Asp Ile
            355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
                420                 425                 430

Gln Arg Val Leu Thr Pro Asn Leu Val Ala Ala Leu Pro Pro Ser Thr
            435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
    515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
```

```
                545                 550                 555                 560
        Gly Cys Ser Ser His Trp Glu Val Glu Asp Leu Gly Thr His Lys Pro
                        565                 570                 575

Pro Val Leu Arg Pro Arg Gly Gln Pro Asn Gln Cys Val Gly His Arg
                    580                 585                 590

Glu Ala Ser Ile His Ala Ser Cys Cys His Ala Pro Gly Leu Glu Cys
                    595                 600                 605

Lys Val Lys Glu His Gly Ile Pro Ala Pro Gln Glu Gln Val Thr Val
                    610                 615                 620

Ala Cys Glu Glu Gly Trp Thr Leu Thr Gly Cys Ser Ala Leu Pro Gly
        625                 630                 635                 640

Thr Ser His Val Leu Gly Ala Tyr Ala Val Asp Asn Thr Cys Val Val
                        645                 650                 655

Arg Ser Arg Asp Val Ser Thr Thr Gly Ser Thr Ser Glu Glu Ala Val
                    660                 665                 670

Thr Ala Val Ala Ile Cys Cys Arg Ser Arg His Leu Ala Gln Ala Ser
                    675                 680                 685

Gln Glu Leu Gln Thr Gly Lys Pro Ile Pro Asn Pro Leu Leu Gly Leu
                    690                 695                 700

Asp Ser Thr Gly Gly Ile Trp Leu Ile Val Phe Gly Val Val Met Gly
        705                 710                 715                 720

Val Ile Val Val Gly Ile Val Ile Leu Ile Phe Thr Gly Ile Arg Asp
                        725                 730                 735

Arg Lys Lys Lys Asn Lys Ala Arg Ser Gly Glu Asn Pro Tyr Ala Ser
                    740                 745                 750

Ile Asp Ile Ser Lys Gly Glu Asn Asn Pro Gly Phe Gln Asn Thr Asp
                    755                 760                 765

Asp Val Gln Thr Ser Phe
                    770

<210> SEQ ID NO 21
<211> LENGTH: 692
<212> TYPE: PRT
<213> ORGANISM: Artificial sequence
<220> FEATURE:
<223> OTHER INFORMATION: Synthetic Construct

<400> SEQUENCE: 21

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140
```

```
Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gly His Val Leu Thr
545                 550                 555                 560

Gly Cys Ser Ser His Trp Glu Val Glu Asp Leu Gly Thr His Lys Pro
```

```
                      565                 570                 575
Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
        675                 680                 685

Gln Glu Leu Gln
    690

<210> SEQ ID NO 22
<211> LENGTH: 65
<212> TYPE: PRT
<213> ORGANISM: Artificial sequence
<220> FEATURE:
<223> OTHER INFORMATION: Synthetic Construct

<400> SEQUENCE: 22

Ile Trp Leu Ile Val Phe Gly Val Val Met Gly Val Ile Val Val Gly
1               5                   10                  15

Ile Val Ile Leu Ile Phe Thr Gly Ile Arg Asp Arg Lys Lys Lys Asn
            20                  25                  30

Lys Ala Arg Ser Gly Glu Asn Pro Tyr Ala Ser Ile Asp Ile Ser Lys
        35                  40                  45

Gly Glu Asn Asn Pro Gly Phe Gln Asn Thr Asp Asp Val Gln Thr Ser
    50                  55                  60

Phe
65

<210> SEQ ID NO 23
<211> LENGTH: 2235
<212> TYPE: DNA
<213> ORGANISM: Artificial sequence
<220> FEATURE:
<223> OTHER INFORMATION: Synthetic Construct

<400> SEQUENCE: 23
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
ctggtgctag ccttgcgttc cgaggaggac ggcctggccg aagcacccga gcacggaacc   180
acagccacct tccaccgctg cgccaaggat ccgtggaggt tgcctggcac ctacgtggtg   240
gtgctgaagg aggagcccca cctctcgcag tcagagcgca ctgcccgccg cctgcaggcc   300
caggctgccc gccggggata cctcaccaag atcctgcatg tcttccatgg ccttcttcct   360
ggcttcctgg tgaagatgag tggcgacctg ctggagctgg ccttgaagtt gccccatgtc   420
gactacatcg aggaggactc ctctgtcttt gcccagagca tcccgtggaa cctggagcgg   480 attcccctc acaggtaccg ggcggatgaa taccagcccc ccgacggagg cagcctggtg   540
gaggtgtatc tcctagacac cagcatacag agtgaccacc gggaaatcga gggcagggtc   600
```

```
atggtcaccg acttcgagaa tgtgcccgag gaggacggga cccgcttcca cagacaggcc    660
agcaagtgtg acagtcatgg cacccacctg gcaggggtgg tcagcggccg ggatgccggc    720
gtggccaagg gtgccggcat gcgcagcctg cgcgtgctca actgccaagg gaagggcacg    780
gttagcggca ccctcatagg cctggagttt attcggaaaa gccagctggt ccagcctgtg    840
gggccactgg tggtgctgct gcccctggcg ggtgggtaca gccgcgtcct caacgccgcc    900
tgccagcgcc tggcgagggc tggggtcgtg ctggtcaccg ctgccggcaa cttccgagac    960
gatgcctgcc tctactcccc agcctcagct cccgaggtca tcacagttgg ggccaccaat   1020
gcccaggacc agccggtgac cctggggact ttggggacca actttggccg ctgtgtggac   1080
ctctttgccc caggggagga catcattggt gcctccagcg actgcagcac ctgctttgtg   1140
tcacagagtg gacatcaca ggctgctgcc cacgtgctg gcattgcagc catgatgctg    1200
tctgccgagc cggagctcac cctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccatggg gcaggttggc agctgttttg caggactgtg    1380
tggtcagcac actcggggcc tacacggatg ccacagcca tcgcccgctg cgccccagat    1440
gaggagctgc tgagctgctc cagtttctcc aggagtggga gcggcgggg cgagcgcatg    1500
gaggcccaag ggggcaagct ggtctgccgg gcccacaacg cttttggggg tgagggtgtc   1560
tacgccattg ccaggtgctg cctgctaccc caggccaact gcagcgtcca cacagctcca   1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacaggagg ccagcatcca cgcttcctgc    1800
tgccatgccc caggtctgga atgcaaagtc aaggagcatg gaatcccggc ccctcaggag   1860
caggtgaccg tggcctgcga ggagggctgg accctgactg gctgcagtgc cctccctggg   1920
acctcccacg tcctgggggc ctacgccgta gacaacacgt gtgtagtcag gagccgggac   1980
gtcagcacta caggcagcac cagcgaagag gccgtgacag ccgttgccat ctgctgccgg   2040
agccggcacc tggcgcaggc ctcccaggag ctccagaccg gtaagcctat ccctaaccct   2100
ctcctcggtc tcgattctac gggaggactg atccccatcg ctgtgggtgg tgccctggcg   2160
gggctggtcc tcatcgtcct catcgcctac ctcgtcggca ggaagaggag tcacgcaggc   2220
taccagacta tctag                                                    2235
```

<210> SEQ ID NO 24
<211> LENGTH: 744
<212> TYPE: PRT
<213> ORGANISM: Artificial sequence
<220> FEATURE:
<223> OTHER INFORMATION: Synthetic Construct

<400> SEQUENCE: 24

Met Gly Thr Val Ser Ser Arg Arg Ser Trp Trp Pro Leu Pro Leu Leu
1               5                   10                  15

Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val

-continued

```
                65                  70                  75                  80
            Val Leu Lys Glu Glu Thr His Leu Ser Gln Ser Glu Arg Thr Ala Arg
                                85                  90                  95

Arg Leu Gln Ala Gln Ala Ala Arg Arg Gly Tyr Leu Thr Lys Ile Leu
                               100                 105                 110

His Val Phe His Gly Leu Leu Pro Gly Phe Leu Val Lys Met Ser Gly
                               115                 120                 125

Asp Leu Leu Glu Leu Ala Leu Lys Leu Pro His Val Asp Tyr Ile Glu
                               130                 135                 140

Glu Asp Ser Ser Val Phe Ala Gln Ser Ile Pro Trp Asn Leu Glu Arg
            145                 150                 155                 160

Ile Thr Pro Pro Arg Tyr Arg Ala Asp Glu Tyr Gln Pro Pro Asp Gly
                               165                 170                 175

Gly Ser Leu Val Glu Val Tyr Leu Leu Asp Thr Ser Ile Gln Ser Asp
                               180                 185                 190

His Arg Glu Ile Glu Gly Arg Val Met Val Thr Asp Phe Glu Asn Val
                               195                 200                 205

Pro Glu Glu Asp Gly Thr Arg Phe His Arg Gln Ala Ser Lys Cys Asp
                               210                 215                 220

Ser His Gly Thr His Leu Ala Gly Val Val Ser Gly Arg Asp Ala Gly
            225                 230                 235                 240

Val Ala Lys Gly Ala Gly Met Arg Ser Leu Arg Val Leu Asn Cys Gln
                               245                 250                 255

Gly Lys Gly Thr Val Ser Gly Thr Leu Ile Gly Leu Glu Phe Ile Arg
                               260                 265                 270

Lys Ser Gln Leu Val Gln Pro Val Gly Pro Leu Val Val Leu Leu Pro
                               275                 280                 285

Leu Ala Gly Gly Tyr Ser Arg Val Leu Asn Ala Ala Cys Gln Arg Leu
                               290                 295                 300

Ala Arg Ala Gly Val Val Leu Val Thr Ala Ala Gly Asn Phe Arg Asp
            305                 310                 315                 320

Asp Ala Cys Leu Tyr Ser Pro Ala Ser Ala Pro Glu Val Ile Thr Val
                               325                 330                 335

Gly Ala Thr Asn Ala Gln Asp Gln Pro Val Thr Leu Gly Thr Leu Gly
                               340                 345                 350

Thr Asn Phe Gly Arg Cys Val Asp Leu Phe Ala Pro Gly Glu Asp Ile
                               355                 360                 365

Ile Gly Ala Ser Ser Asp Cys Ser Thr Cys Phe Val Ser Gln Ser Gly
                               370                 375                 380

Thr Ser Gln Ala Ala Ala His Val Ala Gly Ile Ala Ala Met Met Leu
            385                 390                 395                 400

Ser Ala Glu Pro Glu Leu Thr Leu Ala Glu Leu Arg Gln Arg Leu Ile
                               405                 410                 415

His Phe Ser Ala Lys Asp Val Ile Asn Glu Ala Trp Phe Pro Glu Asp
                               420                 425                 430

Gln Arg Val Leu Thr Pro Asn Leu Val Ala Ala Leu Pro Pro Ser Thr
                               435                 440                 445

His Gly Ala Gly Trp Gln Leu Phe Cys Arg Thr Val Trp Ser Ala His
                               450                 455                 460

Ser Gly Pro Thr Arg Met Ala Thr Ala Ile Ala Arg Cys Ala Pro Asp
            465                 470                 475                 480

Glu Glu Leu Leu Ser Cys Ser Ser Phe Ser Arg Ser Gly Lys Arg Arg
                               485                 490                 495
```

Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
            515                 520                 525

Leu Pro Gln Ala Asn Cys Ser Val His Thr Ala Pro Pro Ala Glu Ala
530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln Thr Gly Lys Pro Ile Pro Asn Pro Leu Leu Gly Leu
690                 695                 700

Asp Ser Thr Gly Gly Leu Ile Pro Ile Ala Val Gly Gly Ala Leu Ala
705                 710                 715                 720

Gly Leu Val Leu Ile Val Leu Ile Ala Tyr Leu Val Gly Arg Lys Arg
                725                 730                 735

Ser His Ala Gly Tyr Gln Thr Ile
            740

<210> SEQ ID NO 25
<211> LENGTH: 35
<212> TYPE: PRT
<213> ORGANISM: Homo sapiens

<400> SEQUENCE: 25

Leu Ile Pro Ile Ala Val Gly Gly Ala Leu Gly Leu Val Leu Ile
1               5                   10                  15

Val Leu Ile Ala Tyr Leu Val Gly Arg Lys Arg Ser His Ala Gly Tyr
            20                  25                  30

Gln Thr Ile
        35

<210> SEQ ID NO 26
<211> LENGTH: 2346
<212> TYPE: DNA
<213> ORGANISM: Artificial sequence
<220> FEATURE:
<223> OTHER INFORMATION: Synthetic Construct

<400> SEQUENCE: 26
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
ctggtgctag ccttgcgttc cgaggaggac ggcctggccg aagcacccga gcacggaacc   180

| | | |
|---|---|---|
| acagccacct tccaccgctg cgccaaggat ccgtggaggt tgcctggcac ctacgtggtg | 240 | |
| gtgctgaagg aggagaccca cctctcgcag tcagagcgca ctgcccgccg cctgcaggcc | 300 | |
| caggctgccc gccggggata cctcaccaag atcctgcatg tcttccatgg ccttcttcct | 360 | |
| ggcttcctgg tgaagatgag tggcgacctg ctggagctgg ccttgaagtt gccccatgtc | 420 | |
| gactacatcg aggaggactc ctctgtcttt gcccagagca tcccgtggaa cctggagcgg | 480 | |
| attacccctc cacggtaccg ggcggatgaa taccagcccc ccgacggagg cagcctggtg | 540 | |
| gaggtgtatc tcctagacac cagcatacag agtgaccacc gggaaatcga gggcagggtc | 600 | |
| atggtcaccg acttcgagaa tgtgcccgag gaggacggga cccgcttcca cagacaggcc | 660 | |
| agcaagtgtg acagtcatgg cacccacctg gcagggtgg tcagcggccg ggatgccggc | 720 | |
| gtggccaagg gtgccggcat gcgcagcctg cgcgtgctca actgccaagg gaagggcacg | 780 | |
| gttagcggca ccctcatagg cctggagttt attcggaaaa gccagctggt ccagcctgtg | 840 | |
| gggccactgg tggtgctgct gccccctgcg ggtgggtaca gccgcgtcct caacgccgcc | 900 | |
| tgccagcgcc tggcgagggc tggggtcgtg ctggtcaccg ctgccggcaa cttccgagac | 960 | |
| gatgcctgcc tctactcccc agcctcagct cccgaggtca tcacagttgg ggccaccaat | 1020 | |
| gcccaggacc agccggtgac cctggggact ttggggacca actttggccg ctgtgtggac | 1080 | |
| ctctttgccc caggggagga catcattggt gcctccagcg actgcagcac ctgctttgtg | 1140 | |
| tcacagagtg ggacatcaca ggctgctgcc cacgtggctg gcattgcagc catgatgctg | 1200 | |
| tctgccgagc cggagctcac cctggccgag ttgaggcaga gactgatcca cttctctgcc | 1260 | |
| aaagatgtca tcaatgaggc ctggttccct gaggaccagc gggtactgac ccccaacctg | 1320 | |
| gtggccgccc tgccccccag cacccatggg gcaggttggc agctgttttg caggactgtg | 1380 | |
| tggtcagcac actcggggcc tacacggatg ccacagcca tcgcccgctg cgccccagat | 1440 | |
| gaggagctgc tgagctgctc cagtttctcc aggagtggga gcggcggggc gagcgcatg | 1500 | |
| gaggcccaag ggggcaagct ggtctgccgg gcccacaacg cttttggggg tgagggtgtc | 1560 | |
| tacgccattg ccaggtgctg cctgctaccc caggccaact gcagcgtcca cacagctcca | 1620 | |
| ccagctgagg ccagcatggg gacccgtgtc cactgccacc aacagggcca cgtcctcaca | 1680 | |
| ggctgcagct cccactggga ggtggaggac cttggcaccc acaagccgcc tgtgctgagg | 1740 | |
| ccacgaggtc agcccaacca gtgcgtgggc cacagggagg ccagcatcca cgcttcctgc | 1800 | |
| tgccatgccc caggtctgga atgcaaagtc aaggagcatg gaatcccggc ccctcaggag | 1860 | |
| caggtgaccg tggcctgcga ggagggctgg accctgactg gctgcagtgc cctccctggg | 1920 | |
| acctcccacg tcctgggggc ctacgccgta gacaacacgt gtgtagtcag gagccgggac | 1980 | |
| gtcagcacta caggcagcac cagcgaagag gccgtgacag ccgttgccat ctgctgccgg | 2040 | |
| agccggcacc tggcgcaggc ctcccaggag ctccagaccg gtaagcctat ccctaaccct | 2100 | |
| ctcctcggtc tcgattctac gggaggagct ctgtccattg tcctccccat cgtgctcctc | 2160 | |
| gtcttccttt gcctgggggt cttccttcta tggaagaact ggcggcttaa gaacatcaac | 2220 | |
| agcatcaact tgacaacccc cgtctatcag aagaccacag aggatgaggt ccacatttgc | 2280 | |
| cacaaccagg acggctacag ctacccctcg agacagatgg tcagtctgga ggatgacgtg | 2340 | |
| gcgtga | 2346 | |

<210> SEQ ID NO 27
<211> LENGTH: 780
<212> TYPE: PRT
<213> ORGANISM: Artificial sequence
<220> FEATURE:
<223> OTHER INFORMATION: Synthetic Construct

<400> SEQUENCE: 27

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Leu Val Leu Ala Leu Arg Ser Glu
            35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
    195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Gly Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
    275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
    355                 360                 365

Ile Gly Ala Ser Ser Asp Cys Ser Thr Cys Phe Val Ser Gln Ser Gly
370                 375                 380

Thr Ser Gln Ala Ala Ala His Val Ala Gly Ile Ala Ala Met Met Leu
385                 390                 395                 400
```

```
Ser Ala Glu Pro Glu Leu Thr Leu Ala Glu Leu Arg Gln Arg Leu Ile
            405                 410                 415
His Phe Ser Ala Lys Asp Val Ile Asn Glu Ala Trp Phe Pro Glu Asp
        420                 425                 430
Gln Arg Val Leu Thr Pro Asn Leu Val Ala Ala Leu Pro Pro Ser Thr
            435                 440                 445
His Gly Ala Gly Trp Gln Leu Phe Cys Arg Thr Val Trp Ser Ala His
    450                 455                 460
Ser Gly Pro Thr Arg Met Ala Thr Ala Ile Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
                500                 505                 510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
        530                 535                 540
Ser Met Gly Thr Arg Val His Cys His Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
                580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
        610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Glu Ala Val
                660                 665                 670
Thr Ala Val Ala Ile Cys Cys Arg Ser Arg His Leu Ala Gln Ala Ser
            675                 680                 685
Gln Glu Leu Gln Thr Gly Lys Pro Ile Pro Asn Pro Leu Leu Gly Leu
        690                 695                 700
Asp Ser Thr Gly Gly Ala Leu Ser Ile Val Leu Pro Ile Val Leu Leu
705                 710                 715                 720
Val Phe Leu Cys Leu Gly Val Phe Leu Leu Trp Lys Asn Trp Arg Leu
                725                 730                 735
Lys Asn Ile Asn Ser Ile Asn Phe Asp Asn Pro Val Tyr Gln Lys Thr
                740                 745                 750
Thr Glu Asp Glu Val His Ile Cys His Asn Gln Asp Gly Tyr Ser Tyr
            755                 760                 765
Pro Arg Gln Met Val Ser Leu Glu Asp Asp Val Ala
        770                 775                 780

<210> SEQ ID NO 28
<211> LENGTH: 71
<212> TYPE: PRT
<213> ORGANISM: Homo sapiens

<400> SEQUENCE: 28
```

```
Ala Leu Ser Ile Val Leu Pro Ile Val Leu Val Phe Leu Cys Leu
1               5                   10                  15

Gly Val Phe Leu Leu Trp Lys Asn Trp Arg Leu Lys Asn Ile Asn Ser
            20                  25                  30

Ile Asn Phe Asp Asn Pro Val Tyr Gln Lys Thr Thr Glu Asp Glu Val
            35                  40                  45

His Ile Cys His Asn Gln Asp Gly Tyr Ser Tyr Pro Arg Gln Met Val
        50                  55                  60

Ser Leu Glu Asp Asp Val Ala
65                  70
```

<210> SEQ ID NO 29
<211> LENGTH: 30
<212> TYPE: PRT
<213> ORGANISM: Homo sapiens

<400> SEQUENCE: 29

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala
            20                  25                  30
```

<210> SEQ ID NO 30
<211> LENGTH: 122
<212> TYPE: PRT
<213> ORGANISM: Homo sapiens

<400> SEQUENCE: 30

```
Gln Glu Asp Glu Asp Gly Asp Tyr Glu Glu Leu Val Leu Ala Leu Arg
1               5                   10                  15

Ser Glu Glu Asp Gly Leu Ala Glu Ala Pro His Gly Thr Thr Ala
            20                  25                  30

Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
        50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln
            115                 120
```

<210> SEQ ID NO 31
<211> LENGTH: 66
<212> TYPE: PRT
<213> ORGANISM: Homo sapiens

<400> SEQUENCE: 31

```
Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
            20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60
```

His Arg
65

<210> SEQ ID NO 32
<211> LENGTH: 474
<212> TYPE: PRT
<213> ORGANISM: Homo sapiens

<400> SEQUENCE: 32

Gln Ala Ser Lys Cys Asp Ser His Gly Thr His Leu Ala Gly Val Val
1               5                   10                  15

Ser Gly Arg Asp Ala Gly Val Ala Lys Gly Ala Ser Met Arg Ser Leu
            20                  25                  30

Arg Val Leu Asn Cys Gln Gly Lys Gly Thr Val Ser Gly Thr Leu Ile
        35                  40                  45

Gly Leu Glu Phe Ile Arg Lys Ser Gln Leu Val Gln Pro Val Gly Pro
    50                  55                  60

Leu Val Val Leu Leu Pro Leu Ala Gly Gly Tyr Ser Arg Val Leu Asn
65                  70                  75                  80

Ala Ala Cys Gln Arg Leu Ala Arg Ala Gly Val Val Leu Val Thr Ala
                85                  90                  95

Ala Gly Asn Phe Arg Asp Asp Ala Cys Leu Tyr Ser Pro Ala Ser Ala
            100                 105                 110

Pro Glu Val Ile Thr Val Gly Ala Thr Asn Ala Gln Asp Gln Pro Val
        115                 120                 125

Thr Leu Gly Thr Leu Gly Thr Asn Phe Gly Arg Cys Val Asp Leu Phe
    130                 135                 140

Ala Pro Gly Glu Asp Ile Ile Gly Ala Ser Ser Asp Cys Ser Thr Cys
145                 150                 155                 160

Phe Val Ser Gln Ser Gly Thr Ser Gln Ala Ala Ala His Val Ala Gly
                165                 170                 175

Ile Ala Ala Met Met Leu Ser Ala Glu Pro Glu Leu Thr Leu Ala Glu
            180                 185                 190

Leu Arg Gln Arg Leu Ile His Phe Ser Ala Lys Asp Val Ile Asn Glu
        195                 200                 205

Ala Trp Phe Pro Glu Asp Gln Arg Val Leu Thr Pro Asn Leu Val Ala
    210                 215                 220

Ala Leu Pro Pro Ser Thr His Gly Ala Gly Trp Gln Leu Phe Cys Arg
225                 230                 235                 240

Thr Val Trp Ser Ala His Ser Gly Pro Thr Arg Met Ala Thr Ala Val
                245                 250                 255

Ala Arg Cys Ala Pro Asp Glu Glu Leu Leu Ser Cys Ser Ser Phe Ser
            260                 265                 270

Arg Ser Gly Lys Arg Arg Gly Glu Arg Met Glu Ala Gln Gly Gly Lys
        275                 280                 285

Leu Val Cys Arg Ala His Asn Ala Phe Gly Gly Glu Gly Val Tyr Ala
    290                 295                 300

Ile Ala Arg Cys Cys Leu Leu Pro Gln Ala Asn Cys Ser Val His Thr
305                 310                 315                 320

Ala Pro Pro Ala Glu Ala Ser Met Gly Thr Arg Val His Cys His Gln
                325                 330                 335

Gln Gly His Val Leu Thr Gly Cys Ser Ser His Trp Glu Val Glu Asp
            340                 345                 350

Leu Gly Thr His Lys Pro Pro Val Leu Arg Pro Arg Gly Gln Pro Asn
        355                 360                 365

Gln Cys Val Gly His Arg Glu Ala Ser Ile His Ala Ser Cys Cys His
    370                 375                 380

Ala Pro Gly Leu Glu Cys Lys Val Lys Glu His Gly Ile Pro Ala Pro
385                 390                 395                 400

Gln Glu Gln Val Thr Val Ala Cys Glu Glu Gly Trp Thr Leu Thr Gly
                405                 410                 415

Cys Ser Ala Leu Pro Gly Thr Ser His Val Leu Gly Ala Tyr Ala Val
                420                 425                 430

Asp Asn Thr Cys Val Val Arg Ser Arg Asp Val Ser Thr Thr Gly Ser
                435                 440                 445

Thr Ser Glu Gly Ala Val Thr Ala Val Ala Ile Cys Cys Arg Ser Arg
450                 455                 460

His Leu Ala Gln Ala Ser Gln Glu Leu Gln
465                 470

<210> SEQ ID NO 33
<211> LENGTH: 662
<212> TYPE: PRT
<213> ORGANISM: Homo sapiens

<400> SEQUENCE: 33

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
                20                  25                  30

Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln Ser Ile Pro Trp Asn Leu
            115                 120                 125

Glu Arg Ile Thr Pro Pro Arg Tyr Arg Ala Asp Glu Tyr Gln Pro Pro
130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
    195                 200                 205

Ala Gly Val Ala Lys Gly Ala Ser Met Arg Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
                260                 265                 270

Arg Leu Ala Arg Ala Gly Val Val Leu Val Thr Ala Ala Gly Asn Phe
            275                 280                 285

Arg Asp Asp Ala Cys Leu Tyr Ser Pro Ala Ser Ala Pro Glu Val Ile
            290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
            325                 330                 335

Asp Ile Ile Gly Ala Ser Ser Asp Cys Ser Thr Cys Phe Val Ser Gln
            340                 345                 350

Ser Gly Thr Ser Gln Ala Ala His Val Ala Gly Ile Ala Ala Met
            355                 360                 365

Met Leu Ser Ala Glu Pro Glu Leu Thr Leu Ala Glu Leu Arg Gln Arg
            370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
            405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
            435                 440                 445

Pro Asp Glu Glu Leu Leu Ser Cys Ser Ser Phe Ser Arg Ser Gly Lys
            450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
            485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gln Gly His Val
            515                 520                 525

Leu Thr Gly Cys Ser Ser His Trp Glu Val Glu Asp Leu Gly Thr His
            530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
            565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
            595                 600                 605

Pro Gly Thr Ser His Val Leu Gly Ala Tyr Ala Val Asp Asn Thr Cys
            610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
            645                 650                 655

Ala Ser Gln Glu Leu Gln
            660

<210> SEQ ID NO 34
<211> LENGTH: 540
<212> TYPE: PRT

<213> ORGANISM: Homo sapiens

<400> SEQUENCE: 34

```
Ser Ile Pro Trp Asn Leu Glu Arg Ile Thr Pro Pro Arg Tyr Arg Ala
1               5                   10                  15
Asp Glu Tyr Gln Pro Pro Asp Gly Gly Ser Leu Val Glu Val Tyr Leu
            20                  25                  30
Leu Asp Thr Ser Ile Gln Ser Asp His Arg Glu Ile Glu Gly Arg Val
        35                  40                  45
Met Val Thr Asp Phe Glu Asn Val Pro Glu Glu Asp Gly Thr Arg Phe
    50                  55                  60
His Arg Gln Ala Ser Lys Cys Asp Ser His Gly Thr His Leu Ala Gly
65                  70                  75                  80
Val Val Ser Gly Arg Asp Ala Gly Val Ala Lys Gly Ala Ser Met Arg
                85                  90                  95
Ser Leu Arg Val Leu Asn Cys Gln Gly Lys Gly Thr Val Ser Gly Thr
            100                 105                 110
Leu Ile Gly Leu Glu Phe Ile Arg Lys Ser Gln Leu Val Gln Pro Val
        115                 120                 125
Gly Pro Leu Val Val Leu Leu Pro Leu Ala Gly Gly Tyr Ser Arg Val
    130                 135                 140
Leu Asn Ala Ala Cys Gln Arg Leu Ala Arg Ala Gly Val Val Leu Val
145                 150                 155                 160
Thr Ala Ala Gly Asn Phe Arg Asp Asp Ala Cys Leu Tyr Ser Pro Ala
                165                 170                 175
Ser Ala Pro Glu Val Ile Thr Val Gly Ala Thr Asn Ala Gln Asp Gln
            180                 185                 190
Pro Val Thr Leu Gly Thr Leu Gly Thr Asn Phe Gly Arg Cys Val Asp
        195                 200                 205
Leu Phe Ala Pro Gly Glu Asp Ile Ile Gly Ala Ser Ser Asp Cys Ser
    210                 215                 220
Thr Cys Phe Val Ser Gln Ser Gly Thr Ser Gln Ala Ala Ala His Val
225                 230                 235                 240
Ala Gly Ile Ala Ala Met Met Leu Ser Ala Glu Pro Glu Leu Thr Leu
                245                 250                 255
Ala Glu Leu Arg Gln Arg Leu Ile His Phe Ser Ala Lys Asp Val Ile
            260                 265                 270
Asn Glu Ala Trp Phe Pro Glu Asp Gln Arg Val Leu Thr Pro Asn Leu
        275                 280                 285
Val Ala Ala Leu Pro Pro Ser Thr His Gly Ala Gly Trp Gln Leu Phe
    290                 295                 300
Cys Arg Thr Val Trp Ser Ala His Ser Gly Pro Thr Arg Met Ala Thr
305                 310                 315                 320
Ala Val Ala Arg Cys Ala Pro Asp Glu Glu Leu Leu Ser Cys Ser Ser
                325                 330                 335
Phe Ser Arg Ser Gly Lys Arg Arg Gly Glu Arg Met Glu Ala Gln Gly
            340                 345                 350
Gly Lys Leu Val Cys Arg Ala His Asn Ala Phe Gly Gly Glu Gly Val
        355                 360                 365
Tyr Ala Ile Ala Arg Cys Cys Leu Leu Pro Gln Ala Asn Cys Ser Val
    370                 375                 380
His Thr Ala Pro Pro Ala Glu Ala Ser Met Gly Thr Arg Val His Cys
385                 390                 395                 400
His Gln Gln Gly His Val Leu Thr Gly Cys Ser Ser His Trp Glu Val
```

```
                    405                 410                 415
Glu Asp Leu Gly Thr His Lys Pro Pro Val Leu Arg Pro Arg Gly Gln
            420                 425                 430
Pro Asn Gln Cys Val Gly His Arg Glu Ala Ser Ile His Ala Ser Cys
        435                 440                 445
Cys His Ala Pro Gly Leu Glu Cys Lys Val Lys Glu His Gly Ile Pro
    450                 455                 460
Ala Pro Gln Glu Gln Val Thr Val Ala Cys Glu Glu Gly Trp Thr Leu
465                 470                 475                 480
Thr Gly Cys Ser Ala Leu Pro Gly Thr Ser His Val Leu Gly Ala Tyr
            485                 490                 495
Ala Val Asp Asn Thr Cys Val Val Arg Ser Arg Asp Val Ser Thr Thr
        500                 505                 510
Gly Ser Thr Ser Glu Gly Ala Val Thr Ala Val Ala Ile Cys Cys Arg
    515                 520                 525
Ser Arg His Leu Ala Gln Ala Ser Gln Glu Leu Gln
530                 535                 540

<210> SEQ ID NO 35
<211> LENGTH: 693
<212> TYPE: PRT
<213> ORGANISM: Mus musculus

<400> SEQUENCE: 35

Met Gly Thr His Cys Ser Ala Trp Leu Arg Trp Pro Leu Pro Leu
1               5                   10                  15
Leu Pro Pro Leu Leu Leu Leu Leu Leu Cys Pro Thr Gly Ala
            20                  25                  30
Gly Ala Gln Glu Asp Gly Asp Tyr Glu Glu Leu Met Leu Ala Leu Pro
        35                  40                  45
Ser Gln Glu Asp Gly Leu Ala Asp Glu Ala His Val Ala Thr Ala
    50                  55                  60
Thr Phe Arg Arg Cys Ser Lys Glu Ala Trp Arg Leu Pro Gly Thr Tyr
65                  70                  75                  80
Ile Val Val Leu Met Glu Glu Thr Gln Arg Leu Gln Ile Glu Gln Thr
                85                  90                  95
Ala His Arg Leu Gln Thr Arg Ala Ala Arg Arg Gly Tyr Val Ile Lys
            100                 105                 110
Val Leu His Ile Phe Tyr Asp Leu Phe Pro Gly Phe Leu Val Lys Met
        115                 120                 125
Ser Ser Asp Leu Leu Gly Leu Ala Leu Lys Leu Pro His Val Glu Tyr
    130                 135                 140
Ile Glu Glu Asp Ser Phe Val Phe Ala Gln Ser Ile Pro Trp Asn Leu
145                 150                 155                 160
Glu Arg Ile Ile Pro Ala Trp His Gln Thr Glu Glu Asp Arg Ser Pro
                165                 170                 175
Asp Gly Ser Ser Gln Val Glu Val Tyr Leu Leu Asp Thr Ser Ile Gln
            180                 185                 190
Gly Ala His Arg Glu Ile Glu Gly Arg Val Thr Ile Thr Asp Phe Asn
        195                 200                 205
Ser Val Pro Glu Glu Asp Gly Thr Arg Phe His Arg Gln Ala Ser Lys
    210                 215                 220
Cys Asp Ser His Gly Thr His Leu Ala Gly Val Val Ser Gly Arg Asp
225                 230                 235                 240
Ala Gly Val Ala Lys Gly Thr Ser Leu His Ser Leu Arg Val Leu Asn
```

```
                    245                 250                 255
Cys Gln Gly Lys Gly Thr Val Ser Gly Thr Leu Ile Gly Leu Glu Phe
            260                 265                 270

Ile Arg Lys Ser Gln Leu Ile Gln Pro Ser Gly Pro Leu Val Val Leu
            275                 280                 285

Leu Pro Leu Ala Gly Gly Tyr Ser Arg Ile Leu Asn Ala Ala Cys Arg
            290                 295                 300

His Leu Ala Arg Thr Gly Val Val Leu Val Ala Ala Gly Asn Phe
305                 310                 315                 320

Arg Asp Asp Ala Cys Leu Tyr Ser Pro Ala Ser Ala Pro Glu Val Ile
                325                 330                 335

Thr Val Gly Ala Thr Asn Ala Gln Asp Gln Pro Val Thr Leu Gly Thr
            340                 345                 350

Leu Gly Thr Asn Phe Gly Arg Cys Val Asp Leu Phe Ala Pro Gly Lys
            355                 360                 365

Asp Ile Ile Gly Ala Ser Ser Asp Cys Ser Thr Cys Phe Met Ser Gln
370                 375                 380

Ser Gly Thr Ser Gln Ala Ala His Val Ala Gly Ile Val Ala Arg
385                 390                 395                 400

Met Leu Ser Arg Glu Pro Thr Leu Thr Leu Ala Glu Leu Arg Gln Arg
                405                 410                 415

Leu Ile His Phe Ser Thr Lys Asp Val Ile Asn Met Ala Trp Phe Pro
                420                 425                 430

Glu Asp Gln Gln Val Leu Thr Pro Asn Leu Val Ala Thr Leu Pro Pro
            435                 440                 445

Ser Thr His Glu Thr Gly Gly Gln Leu Leu Cys Arg Thr Val Trp Ser
            450                 455                 460

Ala His Ser Gly Pro Thr Arg Thr Ala Thr Ala Thr Ala Arg Cys Ala
465                 470                 475                 480

Pro Glu Glu Glu Leu Leu Ser Cys Ser Ser Phe Ser Arg Ser Gly Arg
                485                 490                 495

Arg Arg Gly Asp Trp Ile Glu Ala Ile Gly Gly Gln Gln Val Cys Lys
            500                 505                 510

Ala Leu Asn Ala Phe Gly Gly Glu Gly Val Tyr Ala Val Ala Arg Cys
            515                 520                 525

Cys Leu Val Pro Arg Ala Asn Cys Ser Ile His Asn Thr Pro Ala Ala
            530                 535                 540

Arg Ala Gly Leu Glu Thr His Val His Cys His Gln Lys Asp His Val
545                 550                 555                 560

Leu Thr Gly Cys Ser Phe His Trp Glu Val Glu Asp Leu Ser Val Arg
                565                 570                 575

Arg Gln Pro Ala Leu Arg Ser Arg Arg Gln Pro Gly Gln Cys Val Gly
            580                 585                 590

His Gln Ala Ala Ser Val Tyr Ala Ser Cys Cys His Ala Pro Gly Leu
            595                 600                 605

Glu Cys Lys Ile Lys Glu His Gly Ile Ser Gly Pro Ser Glu Gln Val
            610                 615                 620

Thr Val Ala Cys Glu Ala Gly Trp Thr Leu Thr Gly Cys Asn Val Leu
625                 630                 635                 640

Pro Gly Ala Ser Leu Thr Leu Gly Ala Tyr Ser Val Asp Asn Leu Cys
                645                 650                 655

Val Ala Arg Val His Asp Thr Ala Arg Ala Asp Arg Thr Ser Gly Glu
                660                 665                 670
```

Ala Thr Val Ala Ala Ile Cys Cys Arg Ser Arg Pro Ser Ala Lys
            675                 680                 685

Ala Ser Trp Val Gln
    690

<210> SEQ ID NO 36
<211> LENGTH: 691
<212> TYPE: PRT
<213> ORGANISM: Rattus norvegicus

<400> SEQUENCE: 36

Met Gly Ile Arg Cys Ser Thr Trp Leu Arg Trp Pro Leu Ser Pro Gln
1               5                   10                  15

Leu Leu Leu Leu Leu Leu Leu Cys Pro Thr Gly Ser Arg Ala Gln Asp
            20                  25                  30

Glu Asp Gly Asp Tyr Glu Glu Leu Met Leu Ala Leu Pro Ser Gln Glu
        35                  40                  45

Asp Ser Leu Val Asp Glu Ala Ser His Val Ala Thr Ala Thr Phe Arg
    50                  55                  60

Arg Cys Ser Lys Glu Ala Trp Arg Leu Pro Gly Thr Tyr Val Val Val
65                  70                  75                  80

Leu Met Glu Glu Thr Gln Arg Leu Gln Val Glu Gln Thr Ala His Arg
                85                  90                  95

Leu Gln Thr Trp Ala Ala Arg Arg Gly Tyr Val Ile Lys Val Leu His
            100                 105                 110

Val Phe Tyr Asp Leu Phe Pro Gly Phe Leu Val Lys Met Ser Ser Asp
        115                 120                 125

Leu Leu Gly Leu Ala Leu Lys Leu Pro His Val Glu Tyr Ile Glu Glu
    130                 135                 140

Asp Ser Leu Val Phe Ala Gln Ser Ile Pro Trp Asn Leu Glu Arg Ile
145                 150                 155                 160

Ile Pro Ala Trp Gln Gln Thr Glu Glu Asp Ser Ser Pro Asp Gly Ser
                165                 170                 175

Ser Gln Val Glu Val Tyr Leu Leu Asp Thr Ser Ile Gln Ser Gly His
            180                 185                 190

Arg Glu Ile Glu Gly Arg Val Thr Ile Thr Asp Phe Asn Ser Val Pro
        195                 200                 205

Glu Glu Asp Gly Thr Arg Phe His Arg Gln Ala Ser Lys Cys Asp Ser
    210                 215                 220

His Gly Thr His Leu Ala Gly Val Val Ser Gly Arg Asp Ala Gly Val
225                 230                 235                 240

Ala Lys Gly Thr Ser Leu His Ser Leu Arg Val Leu Asn Cys Gln Gly
                245                 250                 255

Lys Gly Thr Val Ser Gly Thr Leu Ile Gly Leu Glu Phe Ile Arg Lys
            260                 265                 270

Ser Gln Leu Ile Gln Pro Ser Gly Pro Leu Val Val Leu Leu Pro Leu
        275                 280                 285

Ala Gly Gly Tyr Ser Arg Ile Leu Asn Thr Ala Cys Gln Arg Leu Ala
    290                 295                 300

Arg Thr Gly Val Val Leu Val Ala Ala Gly Asn Phe Arg Asp Asp
305                 310                 315                 320

Ala Cys Leu Tyr Ser Pro Ala Ser Ala Pro Glu Val Ile Thr Val Gly
                325                 330                 335

Ala Thr Asn Ala Gln Asp Gln Pro Val Thr Leu Gly Thr Leu Gly Thr
            340                 345                 350

```
Asn Phe Gly Arg Cys Val Asp Leu Phe Ala Pro Gly Lys Asp Ile Ile
            355                 360                 365

Gly Ala Ser Ser Asp Cys Ser Thr Cys Tyr Met Ser Gln Ser Gly Thr
    370                 375                 380

Ser Gln Ala Ala Ala His Val Ala Gly Ile Val Ala Met Met Leu Asn
385                 390                 395                 400

Arg Asp Pro Ala Leu Thr Leu Ala Glu Leu Arg Gln Arg Leu Ile Leu
                405                 410                 415

Phe Ser Thr Lys Asp Val Ile Asn Met Ala Trp Phe Pro Glu Asp Gln
            420                 425                 430

Arg Val Leu Thr Pro Asn Arg Val Ala Thr Leu Pro Pro Ser Thr Gln
                435                 440                 445

Glu Thr Gly Gly Gln Leu Leu Cys Arg Thr Val Trp Ser Ala His Ser
    450                 455                 460

Gly Pro Thr Arg Thr Ala Thr Ala Thr Ala Arg Cys Ala Pro Glu Glu
465                 470                 475                 480

Glu Leu Leu Ser Cys Ser Ser Phe Ser Arg Ser Arg Arg Gly
                485                 490                 495

Asp Arg Ile Glu Ala Ile Gly Gly Gln Gln Val Cys Lys Ala Leu Asn
                500                 505                 510

Ala Phe Gly Gly Glu Gly Val Tyr Ala Val Ala Arg Cys Cys Leu Leu
            515                 520                 525

Pro Arg Val Asn Cys Ser Ile His Asn Thr Pro Ala Ala Arg Ala Gly
                530                 535                 540

Pro Gln Thr Pro Val His Cys His Gln Lys Asp His Val Leu Thr Gly
545                 550                 555                 560

Cys Ser Phe His Trp Glu Val Glu Asn Leu Arg Ala Gln Gln Pro
                565                 570                 575

Leu Leu Arg Ser Arg His Gln Pro Gly Gln Cys Val Gly His Gln Glu
                580                 585                 590

Ala Ser Val His Ala Ser Cys Cys His Ala Pro Gly Leu Glu Cys Lys
        595                 600                 605

Ile Lys Glu His Gly Ile Ala Gly Pro Ala Glu Gln Val Thr Val Ala
    610                 615                 620

Cys Glu Ala Gly Trp Thr Leu Thr Gly Cys Asn Val Leu Pro Gly Ala
625                 630                 635                 640

Ser Leu Pro Leu Gly Ala Tyr Ser Val Asp Asn Val Cys Val Ala Arg
                645                 650                 655

Ile Arg Asp Ala Gly Arg Ala Asp Arg Thr Ser Glu Glu Ala Thr Val
                660                 665                 670

Ala Ala Ala Ile Cys Cys Arg Ser Arg Pro Ser Ala Lys Ala Ser Trp
            675                 680                 685

Val His Gln
    690

<210> SEQ ID NO 37
<211> LENGTH: 692
<212> TYPE: PRT
<213> ORGANISM: Pan troglodytes

<400> SEQUENCE: 37

Met Gly Thr Val Ser Ser Arg Arg Ser Trp Pro Leu Pro Leu Leu
1               5                   10                  15

Leu Leu Leu Leu Leu Leu Leu Gly Pro Ala Gly Ala Arg Ala Gln Glu
                20                  25                  30
```

```
Asp Glu Asp Gly Asp Tyr Glu Glu Leu Val Leu Ala Leu Arg Ser Glu
         35                  40                  45

Glu Asp Gly Leu Ala Glu Ala Pro Glu His Gly Thr Thr Ala Thr Phe
 50                  55                  60

His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Arg Arg Gly Tyr Leu Thr Lys Ile Leu
                 100                 105                 110

His Val Phe His Gly Leu Leu Pro Gly Phe Leu Val Lys Met Ser Gly
             115                 120                 125

Asp Leu Leu Glu Leu Ala Leu Lys Leu Pro His Val Asp Tyr Ile Glu
             130                 135                 140

Glu Asp Ser Ser Val Phe Ala Gln Ser Ile Pro Trp Asn Leu Glu Arg
 145                 150                 155                 160

Ile Thr Pro Pro Arg Tyr Arg Ala Asp Glu Tyr Gln Pro Pro Asp Gly
                 165                 170                 175

Gly Ser Leu Val Glu Val Tyr Leu Leu Asp Thr Ser Ile Gln Ser Asp
             180                 185                 190

His Arg Glu Ile Glu Gly Arg Val Met Val Thr Asp Phe Glu Asn Val
             195                 200                 205

Pro Glu Glu Asp Gly Thr Arg Phe His Arg Gln Ala Ser Lys Cys Asp
 210                 215                 220

Ser His Gly Thr His Leu Ala Gly Val Val Ser Gly Arg Asp Ala Gly
 225                 230                 235                 240

Val Ala Lys Gly Ala Ser Met Arg Ser Leu Arg Val Leu Asn Cys Gln
                 245                 250                 255

Gly Lys Gly Thr Val Ser Gly Thr Leu Ile Gly Leu Glu Phe Ile Arg
             260                 265                 270

Lys Ser Gln Leu Val Gln Pro Val Gly Pro Leu Val Val Leu Leu Pro
             275                 280                 285

Leu Ala Gly Gly Tyr Ser Arg Val Leu Asn Ala Ala Cys Gln Arg Leu
 290                 295                 300

Ala Arg Ala Gly Val Val Leu Val Thr Ala Ala Gly Asn Phe Arg Asp
 305                 310                 315                 320

Asp Ala Cys Leu Tyr Ser Pro Ala Ser Ala Pro Glu Val Ile Thr Val
                 325                 330                 335

Gly Ala Thr Asn Ala Gln Asp Gln Pro Val Thr Leu Gly Thr Leu Gly
             340                 345                 350

Thr Asn Phe Gly Arg Cys Val Asp Leu Phe Ala Pro Gly Glu Asp Ile
 355                 360                 365

Ile Gly Ala Ser Ser Asp Cys Ser Thr Cys Phe Val Ser Gln Ser Gly
 370                 375                 380

Thr Ser Gln Ala Ala Ala His Val Ala Gly Ile Ala Ala Met Met Leu
 385                 390                 395                 400

Ser Ala Glu Pro Glu Leu Thr Leu Ala Glu Leu Arg Gln Arg Leu Ile
                 405                 410                 415

His Phe Ser Ala Lys Asp Val Ile Asn Glu Ala Trp Phe Pro Glu Asp
             420                 425                 430

Gln Arg Val Leu Thr Pro Asn Leu Val Ala Ala Leu Pro Pro Ser Thr
             435                 440                 445

His Gly Ala Gly Trp Gln Leu Phe Cys Arg Thr Val Trp Ser Ala His
 450                 455                 460
```

```
Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
            485                 490                 495

Gly Glu Arg Met Glu Ala Gln Gly Gly Lys Leu Val Cys Arg Ala His
        500                 505                 510

Asn Ala Phe Gly Gly Glu Gly Val Tyr Ala Ile Ala Arg Cys Cys Leu
    515                 520                 525

Leu Pro Gln Ala Asn Cys Ser Ile His Thr Pro Pro Ala Glu Ala
530                 535                 540

Gly Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Met Leu Arg Pro Arg Gly Gln Pro Asn Gln Cys Val Gly His Arg
            580                 585                 590

Glu Ala Ser Ile His Ala Ser Cys Cys Arg Ala Pro Gly Leu Glu Cys
        595                 600                 605

Lys Val Lys Glu His Gly Ile Pro Ala Pro Gln Glu Gln Val Thr Val
610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Ala Gly Ser Thr Ser Glu Glu Ala Val
            660                 665                 670

Ala Ala Val Ala Ile Cys Cys Arg Ser Arg His Leu Ala Gln Ala Ser
        675                 680                 685

Gln Glu Leu Gln
    690

<210> SEQ ID NO 38
<211> LENGTH: 696
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: MISC_FEATURE
<222> LOCATION: (15)..(18)
<223> OTHER INFORMATION: Xaa is any naturally occurring amino acid or is
      absent
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
```

```
<222> LOCATION: (32)..(33)
<223> OTHER INFORMATION: Xaa can be any naturally occurring amino acid
<220> FEATURE:
<221> NAME/KEY: MISC_FEATURE
<222> LOCATION: (36)..(36)
<223> OTHER INFORMATION: Xaa is any naturally occurring amino acid or is
      absent
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(61)
<223> OTHER INFORMATION: Xaa can be any naturally occurring amino acid
<220> FEATURE:
<221> NAME/KEY: misc_feature
<222> LOCATION: (63)..(64)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(93)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: misc_feature
<222> LOCATION: (112)..(113)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid
<220> FEATURE:
```

```
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (120)..(121)
<223> OTHER INFORMATION: Xaa can be any naturally occurring amino acid
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (166)..(166)
<223> OTHER INFORMATION: Xaa can be any naturally occurring amino acid
<220> FEATURE:
<221> NAME/KEY: misc_feature
<222> LOCATION: (168)..(173)
<223> OTHER INFORMATION: Xaa can be any naturally occurring amino acid
<220> FEATURE:
<221> NAME/KEY: misc_feature
<222> LOCATION: (175)..(177)
<223> OTHER INFORMATION: Xaa can be any naturally occurring amino acid
<220> FEATURE:
<221> NAME/KEY: misc_feature
<222> LOCATION: (181)..(181)
<223> OTHER INFORMATION: Xaa can be any naturally occurring amino acid
<220> FEATURE:
<221> NAME/KEY: misc_feature
<222> LOCATION: (183)..(183)
<223> OTHER INFORMATION: Xaa can be any naturally occurring amino acid
<220> FEATURE:
<221> NAME/KEY: misc_feature
<222> LOCATION: (195)..(196)
<223> OTHER INFORMATION: Xaa can be any naturally occurring amino acid
<220> FEATURE:
<221> NAME/KEY: misc_feature
<222> LOCATION: (205)..(206)
<223> OTHER INFORMATION: Xaa can be any naturally occurring amino acid
<220> FEATURE:
<221> NAME/KEY: misc_feature
<222> LOCATION: (210)..(211)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (251)..(252)
<223> OTHER INFORMATION: Xaa can be any naturally occurring amino acid
<220> FEATURE:
<221> NAME/KEY: misc_feature
<222> LOCATION: (281)..(281)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (300)..(300)
<223> OTHER INFORMATION: Xaa can be any naturally occurring amino acid
<220> FEATURE:
```

```
<221> NAME/KEY: misc_feature
<222> LOCATION: (303)..(303)
<223> OTHER INFORMATION: Xaa can be any naturally occurring amino acid
<220> FEATURE:
<221> NAME/KEY: misc_feature
<222> LOCATION: (306)..(307)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (370)..(370)
<223> OTHER INFORMATION: Xaa can be any naturally occurring amino acid
<220> FEATURE:
<221> NAME/KEY: misc_feature
<222> LOCATION: (383)..(384)
<223> OTHER INFORMATION: Xaa can be any naturally occurring amino acid
<220> FEATURE:
<221> NAME/KEY: misc_feature
<222> LOCATION: (400)..(400)
<223> OTHER INFORMATION: Xaa can be any naturally occurring amino acid
<220> FEATURE:
<221> NAME/KEY: misc_feature
<222> LOCATION: (405)..(407)
<223> OTHER INFORMATION: Xaa can be any naturally occurring amino acid
<220> FEATURE:
<221> NAME/KEY: misc_feature
<222> LOCATION: (409)..(409)
<223> OTHER INFORMATION: Xaa can be any naturally occurring amino acid
<220> FEATURE:
<221> NAME/KEY: misc_feature
<222> LOCATION: (421)..(421)
<223> OTHER INFORMATION: Xaa can be any naturally occurring amino acid
<220> FEATURE:
<221> NAME/KEY: misc_feature
<222> LOCATION: (424)..(424)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (453)..(455)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (460)..(460)
<223> OTHER INFORMATION: Xaa can be any naturally occurring amino acid
<220> FEATURE:
<221> NAME/KEY: misc_feature
<222> LOCATION: (474)..(474)
<223> OTHER INFORMATION: Xaa can be any naturally occurring amino acid
<220> FEATURE:
<221> NAME/KEY: misc_feature
<222> LOCATION: (478)..(478)
<223> OTHER INFORMATION: Xaa can be any naturally occurring amino acid
<220> FEATURE:
```

```
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (498)..(498)
<223> OTHER INFORMATION: Xaa can be any naturally occurring amino acid
<220> FEATURE:
<221> NAME/KEY: misc_feature
<222> LOCATION: (502)..(504)
<223> OTHER INFORMATION: Xaa can be any naturally occurring amino acid
<220> FEATURE:
<221> NAME/KEY: misc_feature
<222> LOCATION: (507)..(507)
<223> OTHER INFORMATION: Xaa can be any naturally occurring amino acid
<220> FEATURE:
<221> NAME/KEY: misc_feature
<222> LOCATION: (510)..(511)
<223> OTHER INFORMATION: Xaa can be any naturally occurring amino acid
<220> FEATURE:
<221> NAME/KEY: misc_feature
<222> LOCATION: (514)..(514)
<223> OTHER INFORMATION: Xaa can be any naturally occurring amino acid
<220> FEATURE:
<221> NAME/KEY: misc_feature
<222> LOCATION: (516)..(516)
<223> OTHER INFORMATION: Xaa can be any naturally occurring amino acid
<220> FEATURE:
<221> NAME/KEY: misc_feature
<222> LOCATION: (527)..(527)
<223> OTHER INFORMATION: Xaa can be any naturally occurring amino acid
<220> FEATURE:
<221> NAME/KEY: misc_feature
<222> LOCATION: (533)..(533)
<223> OTHER INFORMATION: Xaa can be any naturally occurring amino acid
<220> FEATURE:
<221> NAME/KEY: misc_feature
<222> LOCATION: (535)..(536)
<223> OTHER INFORMATION: Xaa can be any naturally occurring amino acid
<220> FEATURE:
<221> NAME/KEY: misc_feature
<222> LOCATION: (540)..(540)
<223> OTHER INFORMATION: Xaa can be any naturally occurring amino acid
<220> FEATURE:
<221> NAME/KEY: misc_feature
<222> LOCATION: (542)..(543)
<223> OTHER INFORMATION: Xaa can be any naturally occurring amino acid
<220> FEATURE:
<221> NAME/KEY: misc_feature
<222> LOCATION: (545)..(545)
<223> OTHER INFORMATION: Xaa can be any naturally occurring amino acid
<220> FEATURE:
<221> NAME/KEY: misc_feature
<222> LOCATION: (547)..(547)
<223> OTHER INFORMATION: Xaa can be any naturally occurring amino acid
<220> FEATURE:
<221> NAME/KEY: misc_feature
<222> LOCATION: (549)..(551)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (559)..(560)
<223> OTHER INFORMATION: Xaa can be any naturally occurring amino acid
<220> FEATURE:
<221> NAME/KEY: misc_feature
<222> LOCATION: (568)..(568)
<223> OTHER INFORMATION: Xaa can be any naturally occurring amino acid
<220> FEATURE:
<221> NAME/KEY: misc_feature
<222> LOCATION: (574)..(574)
<223> OTHER INFORMATION: Xaa can be any naturally occurring amino acid
<220> FEATURE:
<221> NAME/KEY: misc_feature
<222> LOCATION: (576)..(580)
<223> OTHER INFORMATION: Xaa can be any naturally occurring amino acid
<220> FEATURE:
```

```
<221> NAME/KEY: misc_feature
<222> LOCATION: (582)..(582)
<223> OTHER INFORMATION: Xaa can be any naturally occurring amino acid
<220> FEATURE:
<221> NAME/KEY: misc_feature
<222> LOCATION: (585)..(585)
<223> OTHER INFORMATION: Xaa can be any naturally occurring amino acid
<220> FEATURE:
<221> NAME/KEY: misc_feature
<222> LOCATION: (587)..(587)
<223> OTHER INFORMATION: Xaa can be any naturally occurring amino acid
<220> FEATURE:
<221> NAME/KEY: misc_feature
<222> LOCATION: (590)..(590)
<223> OTHER INFORMATION: Xaa can be any naturally occurring amino acid
<220> FEATURE:
<221> NAME/KEY: misc_feature
<222> LOCATION: (596)..(597)
<223> OTHER INFORMATION: Xaa can be any naturally occurring amino acid
<220> FEATURE:
<221> NAME/KEY: misc_feature
<222> LOCATION: (600)..(601)
<223> OTHER INFORMATION: Xaa can be any naturally occurring amino acid
<220> FEATURE:
<221> NAME/KEY: misc_feature
<222> LOCATION: (606)..(606)
<223> OTHER INFORMATION: Xaa can be any naturally occurring amino acid
<220> FEATURE:
<221> NAME/KEY: misc_feature
<222> LOCATION: (614)..(614)
<223> OTHER INFORMATION: Xaa can be any naturally occurring amino acid
<220> FEATURE:
<221> NAME/KEY: misc_feature
<222> LOCATION: (620)..(621)
<223> OTHER INFORMATION: Xaa can be any naturally occurring amino acid
<220> FEATURE:
<221> NAME/KEY: misc_feature
<222> LOCATION: (623)..(623)
<223> OTHER INFORMATION: Xaa can be any naturally occurring amino acid
<220> FEATURE:
<221> NAME/KEY: misc_feature
<222> LOCATION: (632)..(632)
<223> OTHER INFORMATION: Xaa can be any naturally occurring amino acid
<220> FEATURE:
<221> NAME/KEY: misc_feature
<222> LOCATION: (640)..(641)
<223> OTHER INFORMATION: Xaa can be any naturally occurring amino acid
<220> FEATURE:
<221> NAME/KEY: misc_feature
<222> LOCATION: (645)..(645)
<223> OTHER INFORMATION: Xaa can be any naturally occurring amino acid
<220> FEATURE:
<221> NAME/KEY: misc_feature
<222> LOCATION: (647)..(648)
<223> OTHER INFORMATION: Xaa can be any naturally occurring amino acid
<220> FEATURE:
<221> NAME/KEY: misc_feature
<222> LOCATION: (653)..(653)
<223> OTHER INFORMATION: Xaa can be any naturally occurring amino acid
<220> FEATURE:
<221> NAME/KEY: misc_feature
<222> LOCATION: (657)..(657)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (662)..(663)
<223> OTHER INFORMATION: Xaa can be any naturally occurring amino acid
<220> FEATURE:
<221> NAME/KEY: misc_feature
<222> LOCATION: (665)..(670)
<223> OTHER INFORMATION: Xaa can be any naturally occurring amino acid
<220> FEATURE:
<221> NAME/KEY: misc_feature
<222> LOCATION: (673)..(674)
<223> OTHER INFORMATION: Xaa can be any naturally occurring amino acid
<220> FEATURE:
```

```
<221> NAME/KEY: misc_feature
<222> LOCATION: (676)..(677)
<223> OTHER INFORMATION: Xaa can be any naturally occurring amino acid
<220> FEATURE:
<221> NAME/KEY: misc_feature
<222> LOCATION: (679)..(679)
<223> OTHER INFORMATION: Xaa can be any naturally occurring amino acid
<220> FEATURE:
<221> NAME/KEY: misc_feature
<222> LOCATION: (687)..(688)
<223> OTHER INFORMATION: Xaa can be any naturally occurring amino acid
<220> FEATURE:
<221> NAME/KEY: misc_feature
<222> LOCATION: (690)..(690)
<223> OTHER INFORMATION: Xaa can be any naturally occurring amino acid
<220> FEATURE:
<221> NAME/KEY: misc_feature
<222> LOCATION: (693)..(695)
<223> OTHER INFORMATION: Xaa can be any naturally occurring amino acid
<220> FEATURE:
<221> NAME/KEY: MISC_FEATURE
<222> LOCATION: (696)..(696)
<223> OTHER INFORMATION: Xaa is any naturally occurring amino acid or is
      absent

<400> SEQUENCE: 38

Met Gly Xaa Xaa Xaa Ser Xaa Xaa Xaa Xaa Trp Pro Leu Pro Xaa Xaa
1               5                   10                  15

Xaa Xaa Xaa Xaa Leu Leu Leu Leu Leu Leu Xaa Pro Xaa Gly Xaa
            20                  25                  30

Xaa Ala Gln Xaa Asp Glu Asp Gly Asp Tyr Glu Glu Leu Xaa Leu Ala
        35                  40                  45

Leu Xaa Ser Xaa Glu Asp Xaa Leu Xaa Xaa Xaa Xaa His Xaa Xaa
    50                  55                  60

Thr Ala Thr Phe Xaa Arg Cys Xaa Lys Xaa Xaa Trp Arg Leu Pro Gly
65              70                  75                  80

Thr Tyr Xaa Val Val Leu Xaa Glu Glu Thr Xaa Xaa Xaa Gln Xaa Glu
            85                  90                  95

Xaa Thr Ala Xaa Arg Leu Gln Xaa Xaa Ala Ala Arg Arg Gly Tyr Xaa
        100                 105                 110

Xaa Lys Xaa Leu His Xaa Phe Xaa Xaa Leu Xaa Pro Gly Phe Leu Val
        115                 120                 125

Lys Met Ser Xaa Asp Leu Leu Xaa Leu Ala Leu Lys Leu Pro His Val
130                 135                 140

Xaa Tyr Ile Glu Glu Asp Ser Xaa Val Phe Ala Gln Ser Ile Pro Trp
145                 150                 155                 160

Asn Leu Glu Arg Ile Xaa Pro Xaa Xaa Xaa Xaa Xaa Glu Xaa Xaa
            165                 170                 175

Xaa Pro Asp Gly Xaa Ser Xaa Val Glu Val Tyr Leu Leu Asp Thr Ser
            180                 185                 190

Ile Gln Xaa Xaa His Arg Glu Ile Glu Gly Arg Val Xaa Xaa Thr Asp
        195                 200                 205

Phe Xaa Xaa Val Pro Glu Glu Asp Gly Thr Arg Phe His Arg Gln Ala
210                 215                 220

Ser Lys Cys Asp Ser His Gly Thr His Leu Ala Gly Val Val Ser Gly
225                 230                 235                 240

Arg Asp Ala Gly Val Ala Lys Gly Xaa Ser Xaa Xaa Ser Leu Arg Val
            245                 250                 255

Leu Asn Cys Gln Gly Lys Gly Thr Val Ser Gly Thr Leu Ile Gly Leu
            260                 265                 270

Glu Phe Ile Arg Lys Ser Gln Leu Xaa Gln Pro Xaa Gly Pro Leu Val
275                 280                 285
```

```
Val Leu Leu Pro Leu Ala Gly Gly Tyr Ser Arg Xaa Leu Asn Xaa Ala
    290                 295                 300

Cys Xaa Xaa Leu Ala Arg Xaa Gly Val Val Leu Val Xaa Ala Ala Gly
305                 310                 315                 320

Asn Phe Arg Asp Asp Ala Cys Leu Tyr Ser Pro Ala Ser Ala Pro Glu
                325                 330                 335

Val Ile Thr Val Gly Ala Thr Asn Ala Gln Asp Gln Pro Val Thr Leu
                340                 345                 350

Gly Thr Leu Gly Thr Asn Phe Gly Arg Cys Val Asp Leu Phe Ala Pro
                355                 360                 365

Gly Xaa Asp Ile Ile Gly Ala Ser Ser Asp Cys Ser Thr Cys Xaa Xaa
    370                 375                 380

Ser Gln Ser Gly Thr Ser Gln Ala Ala His Val Ala Gly Ile Xaa
385                 390                 395                 400

Ala Met Met Leu Xaa Xaa Xaa Pro Xaa Leu Thr Leu Ala Glu Leu Arg
                405                 410                 415

Gln Arg Leu Ile Xaa Phe Ser Xaa Lys Asp Val Ile Asn Xaa Ala Trp
                420                 425                 430

Phe Pro Glu Asp Gln Xaa Val Leu Thr Pro Asn Xaa Val Ala Xaa Leu
                435                 440                 445

Pro Pro Ser Thr Xaa Xaa Xaa Gly Xaa Gln Leu Xaa Cys Arg Thr Val
450                 455                 460

Trp Ser Ala His Ser Gly Pro Thr Arg Xaa Ala Thr Ala Xaa Ala Arg
465                 470                 475                 480

Cys Ala Pro Xaa Glu Glu Leu Leu Ser Cys Ser Ser Phe Ser Arg Ser
                485                 490                 495

Gly Xaa Arg Arg Gly Xaa Xaa Glu Ala Xaa Gly Gly Xaa Xaa Val
                500                 505                 510

Cys Xaa Ala Xaa Asn Ala Phe Gly Gly Glu Gly Val Tyr Ala Xaa Ala
                515                 520                 525

Arg Cys Cys Leu Xaa Pro Xaa Xaa Asn Cys Ser Xaa His Xaa Xaa Pro
    530                 535                 540

Xaa Ala Xaa Ala Xaa Xaa Xaa Thr Xaa Val His Cys His Gln Xaa Xaa
545                 550                 555                 560

His Val Leu Thr Gly Cys Ser Xaa His Trp Glu Val Glu Xaa Leu Xaa
                565                 570                 575

Xaa Xaa Xaa Xaa Pro Xaa Leu Arg Xaa Arg Xaa Gln Pro Xaa Gln Cys
                580                 585                 590

Val Gly His Xaa Xaa Ala Ser Xaa Xaa Ala Ser Cys Cys Xaa Ala Pro
                595                 600                 605

Gly Leu Glu Cys Lys Xaa Lys Glu His Gly Ile Xaa Xaa Pro Xaa Glu
    610                 615                 620

Gln Val Thr Val Ala Cys Glu Xaa Gly Trp Thr Leu Thr Gly Cys Xaa
625                 630                 635                 640

Xaa Leu Pro Gly Xaa Ser Xaa Xaa Leu Gly Ala Tyr Xaa Val Asp Asn
                645                 650                 655

Xaa Cys Val Xaa Arg Xaa Xaa Asp Xaa Xaa Xaa Xaa Xaa Thr Ser
    660                 665                 670

Xaa Xaa Ala Xaa Xaa Ala Xaa Ala Ile Cys Cys Arg Ser Arg Xaa Xaa
    675                 680                 685

Ala Xaa Ala Ser Xaa Xaa Xaa Xaa
    690                 695
```

```
<210> SEQ ID NO 39
<211> LENGTH: 11
<212> TYPE: PRT
<213> ORGANISM: Homo sapiens

<400> SEQUENCE: 39

Leu Val Leu Ala Leu Arg Ser Glu Glu Asp Gly
1               5                   10

<210> SEQ ID NO 40
<211> LENGTH: 11
<212> TYPE: PRT
<213> ORGANISM: Homo sapiens

<400> SEQUENCE: 40

Leu Val Leu Ala Leu Leu Ser Glu Glu Asp Gly
1               5                   10

<210> SEQ ID NO 41
<211> LENGTH: 11
<212> TYPE: PRT
<213> ORGANISM: Homo sapiens

<400> SEQUENCE: 41

Thr Phe His Arg Cys Ala Lys Asp Pro Trp Arg
1               5                   10

<210> SEQ ID NO 42
<211> LENGTH: 20
<212> TYPE: PRT
<213> ORGANISM: Homo sapiens

<400> SEQUENCE: 42

Thr Phe His Arg Cys Pro Arg Ile Arg Arg Gly Gly Cys Leu Ala Pro
1               5                   10                  15

Thr Trp Trp Cys
            20

<210> SEQ ID NO 43
<211> LENGTH: 12
<212> TYPE: PRT
<213> ORGANISM: Homo sapiens

<400> SEQUENCE: 43

Glu Arg Thr Ala Arg Arg Lys Leu Gln Ala Gln Ala
1               5                   10

<210> SEQ ID NO 44
<211> LENGTH: 11
<212> TYPE: PRT
<213> ORGANISM: Homo sapiens

<400> SEQUENCE: 44

Glu Arg Thr Ala Arg Lys Leu Gln Ala Gln Ala
1               5                   10

<210> SEQ ID NO 45
<211> LENGTH: 11
<212> TYPE: PRT
<213> ORGANISM: Homo sapiens

<400> SEQUENCE: 45

Gln Ala Ala Arg Arg Gly Tyr Leu Thr Lys Ile
1               5                   10
```

```
<210> SEQ ID NO 46
<211> LENGTH: 11
<212> TYPE: PRT
<213> ORGANISM: Homo sapiens

<400> SEQUENCE: 46

Gln Ala Ala Arg Arg Arg Tyr Leu Thr Lys Ile
1               5                   10

<210> SEQ ID NO 47
<211> LENGTH: 11
<212> TYPE: PRT
<213> ORGANISM: Homo sapiens

<400> SEQUENCE: 47

Leu Pro His Val Asp Tyr Ile Glu Glu Asp Ser
1               5                   10

<210> SEQ ID NO 48
<211> LENGTH: 5
<212> TYPE: PRT
<213> ORGANISM: Homo sapiens

<400> SEQUENCE: 48

Leu Pro His Val Asp
1               5

<210> SEQ ID NO 49
<211> LENGTH: 11
<212> TYPE: PRT
<213> ORGANISM: Homo sapiens

<400> SEQUENCE: 49

Arg Ser Leu Arg Val Leu Asn Cys Gln Gly Lys
1               5                   10

<210> SEQ ID NO 50
<211> LENGTH: 11
<212> TYPE: PRT
<213> ORGANISM: Homo sapiens

<400> SEQUENCE: 50

Arg Ser Leu Arg Val Phe Asn Cys Gln Gly Lys
1               5                   10

<210> SEQ ID NO 51
<211> LENGTH: 11
<212> TYPE: PRT
<213> ORGANISM: Homo sapiens

<400> SEQUENCE: 51

Ala Val Ala Ile Cys Cys Arg Ser Arg His Leu
1               5                   10

<210> SEQ ID NO 52
<211> LENGTH: 5
<212> TYPE: PRT
<213> ORGANISM: Homo sapiens

<400> SEQUENCE: 52

Ala Val Ala Ile Cys
1               5

<210> SEQ ID NO 53
<211> LENGTH: 11
<212> TYPE: PRT
```

<213> ORGANISM: Homo sapiens

<400> SEQUENCE: 53

Phe Leu Val Lys Met Ser Gly Asp Leu Leu Glu
1               5                   10

<210> SEQ ID NO 54
<211> LENGTH: 11
<212> TYPE: PRT
<213> ORGANISM: Homo sapiens

<400> SEQUENCE: 54

Phe Leu Val Lys Met Arg Gly Asp Leu Leu Glu
1               5                   10

<210> SEQ ID NO 55
<211> LENGTH: 11
<212> TYPE: PRT
<213> ORGANISM: Homo sapiens

<400> SEQUENCE: 55

Glu Asp Gly Thr Arg Phe His Arg Gln Ala Ser
1               5                   10

<210> SEQ ID NO 56
<211> LENGTH: 11
<212> TYPE: PRT
<213> ORGANISM: Homo sapiens

<400> SEQUENCE: 56

Glu Asp Gly Thr Arg Leu His Arg Gln Ala Ser
1               5                   10

<210> SEQ ID NO 57
<211> LENGTH: 12
<212> TYPE: PRT
<213> ORGANISM: Homo sapiens

<400> SEQUENCE: 57

Glu Asp Gly Thr Arg Phe His Arg Gln Ala Ser Lys
1               5                   10

<210> SEQ ID NO 58
<211> LENGTH: 12
<212> TYPE: PRT
<213> ORGANISM: Homo sapiens

<400> SEQUENCE: 58

Glu Asp Gly Thr Arg Phe His Ser Gln Ala Ser Lys
1               5                   10

<210> SEQ ID NO 59
<211> LENGTH: 11
<212> TYPE: PRT
<213> ORGANISM: Homo sapiens

<400> SEQUENCE: 59

Ile Gly Ala Ser Ser Asp Cys Ser Thr Cys Phe
1               5                   10

<210> SEQ ID NO 60
<211> LENGTH: 11
<212> TYPE: PRT
<213> ORGANISM: Homo sapiens

<400> SEQUENCE: 60

-continued

Ile Gly Ala Ser Ser Tyr Cys Ser Thr Cys Phe
1               5                   10

<210> SEQ ID NO 61
<211> LENGTH: 11
<212> TYPE: PRT
<213> ORGANISM: Homo sapiens

<400> SEQUENCE: 61

His Ser Gly Pro Thr Arg Met Ala Thr Ala Ile
1               5                   10

<210> SEQ ID NO 62
<211> LENGTH: 11
<212> TYPE: PRT
<213> ORGANISM: Homo sapiens

<400> SEQUENCE: 62

His Ser Gly Pro Thr Trp Met Ala Thr Ala Ile
1               5                   10

<210> SEQ ID NO 63
<211> LENGTH: 11
<212> TYPE: PRT
<213> ORGANISM: Homo sapiens

<400> SEQUENCE: 63

Arg Ser Gly Lys Arg Gly Glu Arg Met Glu
1               5                   10

<210> SEQ ID NO 64
<211> LENGTH: 11
<212> TYPE: PRT
<213> ORGANISM: Homo sapiens

<400> SEQUENCE: 64

Arg Ser Gly Lys Arg Trp Gly Glu Arg Met Glu
1               5                   10

<210> SEQ ID NO 65
<211> LENGTH: 9
<212> TYPE: PRT
<213> ORGANISM: Homo sapiens

<400> SEQUENCE: 65

Met Gly Thr Val Ser Ser Arg Arg Ser
1               5

<210> SEQ ID NO 66
<211> LENGTH: 9
<212> TYPE: PRT
<213> ORGANISM: Homo sapiens

<400> SEQUENCE: 66

Met Gly Thr Ile Ser Ser Arg Arg Ser
1               5

<210> SEQ ID NO 67
<211> LENGTH: 14
<212> TYPE: PRT
<213> ORGANISM: Homo sapiens

<400> SEQUENCE: 67

Leu Pro Leu Leu Leu Leu Leu Leu Leu Leu Leu Gly Pro Ala
1               5                   10

```
<210> SEQ ID NO 68
<211> LENGTH: 15
<212> TYPE: PRT
<213> ORGANISM: Homo sapiens

<400> SEQUENCE: 68

Leu Pro Leu Leu Leu Leu Leu Leu Leu Leu Leu Leu Gly Pro Ala
1               5                   10                  15

<210> SEQ ID NO 69
<211> LENGTH: 13
<212> TYPE: PRT
<213> ORGANISM: Homo sapiens

<400> SEQUENCE: 69

Leu Pro Leu Leu Leu Leu Leu Leu Leu Leu Leu Gly Pro
1               5                   10

<210> SEQ ID NO 70
<211> LENGTH: 15
<212> TYPE: PRT
<213> ORGANISM: Homo sapiens

<400> SEQUENCE: 70

Leu Pro Leu Leu Leu Leu Leu Leu Leu Leu Leu Leu Leu Gly Pro
1               5                   10                  15

<210> SEQ ID NO 71
<211> LENGTH: 11
<212> TYPE: PRT
<213> ORGANISM: Homo sapiens

<400> SEQUENCE: 71

Glu Glu Asp Gly Leu Val Glu Ala Pro Glu His
1               5                   10

<210> SEQ ID NO 72
<211> LENGTH: 11
<212> TYPE: PRT
<213> ORGANISM: Homo sapiens

<400> SEQUENCE: 72

Glu Glu Asp Gly Leu Ala Glu Ala Pro Glu His
1               5                   10

<210> SEQ ID NO 73
<211> LENGTH: 11
<212> TYPE: PRT
<213> ORGANISM: Homo sapiens

<400> SEQUENCE: 73

Glu Glu Asp Gly Leu Val Glu Ala Pro Glu His
1               5                   10

<210> SEQ ID NO 74
<211> LENGTH: 11
<212> TYPE: PRT
<213> ORGANISM: Homo sapiens

<400> SEQUENCE: 74

Leu Ala Glu Ala Pro Glu His Gly Thr Thr Ala
1               5                   10

<210> SEQ ID NO 75
```

```
<211> LENGTH: 11
<212> TYPE: PRT
<213> ORGANISM: Homo sapiens

<400> SEQUENCE: 75

Leu Ala Glu Ala Pro Lys His Gly Thr Thr Ala
1               5                   10

<210> SEQ ID NO 76
<211> LENGTH: 11
<212> TYPE: PRT
<213> ORGANISM: Homo sapiens

<400> SEQUENCE: 76

Trp Arg Leu Pro Gly Thr Tyr Val Val Val Leu
1               5                   10

<210> SEQ ID NO 77
<211> LENGTH: 15
<212> TYPE: PRT
<213> ORGANISM: Homo sapiens

<400> SEQUENCE: 77

Trp Arg Leu Pro Gly Ile Tyr Val Val Val Leu Lys Glu Glu Thr
1               5                   10                  15

<210> SEQ ID NO 78
<211> LENGTH: 11
<212> TYPE: PRT
<213> ORGANISM: Homo sapiens

<400> SEQUENCE: 78

Thr Lys Ile Leu His Val Phe His Gly Leu Leu
1               5                   10

<210> SEQ ID NO 79
<211> LENGTH: 11
<212> TYPE: PRT
<213> ORGANISM: Homo sapiens

<400> SEQUENCE: 79

Thr Lys Ile Leu His Ala Phe His Gly Leu Leu
1               5                   10

<210> SEQ ID NO 80
<211> LENGTH: 11
<212> TYPE: PRT
<213> ORGANISM: Homo sapiens

<400> SEQUENCE: 80

Gln Ser Ile Pro Trp Asn Leu Glu Arg Ile Thr
1               5                   10

<210> SEQ ID NO 81
<211> LENGTH: 11
<212> TYPE: PRT
<213> ORGANISM: Homo sapiens

<400> SEQUENCE: 81

Gln Ser Ile Pro Trp Lys Leu Glu Arg Ile Thr
1               5                   10

<210> SEQ ID NO 82
<211> LENGTH: 11
<212> TYPE: PRT
<213> ORGANISM: Homo sapiens
```

```
<400> SEQUENCE: 82

Gly Val Val Ser Gly Arg Asp Ala Gly Val Ala
1               5                   10

<210> SEQ ID NO 83
<211> LENGTH: 11
<212> TYPE: PRT
<213> ORGANISM: Homo sapiens

<400> SEQUENCE: 83

Gly Val Val Ser Gly Trp Asp Ala Gly Val Ala
1               5                   10

<210> SEQ ID NO 84
<211> LENGTH: 11
<212> TYPE: PRT
<213> ORGANISM: Homo sapiens

<400> SEQUENCE: 84

Gly Thr Asn Phe Gly Arg Cys Val Asp Leu Phe
1               5                   10

<210> SEQ ID NO 85
<211> LENGTH: 11
<212> TYPE: PRT
<213> ORGANISM: Homo sapiens

<400> SEQUENCE: 85

Gly Thr Asn Phe Gly His Cys Val Asp Leu Phe
1               5                   10

<210> SEQ ID NO 86
<211> LENGTH: 11
<212> TYPE: PRT
<213> ORGANISM: Homo sapiens

<400> SEQUENCE: 86

Ser Gln Ala Ala Ala His Val Ala Gly Ile Ala
1               5                   10

<210> SEQ ID NO 87
<211> LENGTH: 11
<212> TYPE: PRT
<213> ORGANISM: Homo sapiens

<400> SEQUENCE: 87

Ser Gln Ala Ala Ala Asn Val Ala Gly Ile Ala
1               5                   10

<210> SEQ ID NO 88
<211> LENGTH: 11
<212> TYPE: PRT
<213> ORGANISM: Homo sapiens

<400> SEQUENCE: 88

Arg Gln Arg Leu Ile His Phe Ser Ala Lys Asp
1               5                   10

<210> SEQ ID NO 89
<211> LENGTH: 11
<212> TYPE: PRT
<213> ORGANISM: Homo sapiens

<400> SEQUENCE: 89
```

```
Arg Gln Arg Leu Ile Gln Phe Ser Ala Lys Asp
1               5                   10
```

<210> SEQ ID NO 90
<211> LENGTH: 11
<212> TYPE: PRT
<213> ORGANISM: Homo sapiens

<400> SEQUENCE: 90

```
Ser Ala Lys Asp Val Ile Asn Glu Ala Trp Phe
1               5                   10
```

<210> SEQ ID NO 91
<211> LENGTH: 11
<212> TYPE: PRT
<213> ORGANISM: Homo sapiens

<400> SEQUENCE: 91

```
Ser Ala Lys Asp Val Val Asn Glu Ala Trp Phe
1               5                   10
```

<210> SEQ ID NO 92
<211> LENGTH: 11
<212> TYPE: PRT
<213> ORGANISM: Homo sapiens

<400> SEQUENCE: 92

```
Ala Gln Asp Val Ile Asn Glu Ala Trp Phe Pro
1               5                   10
```

<210> SEQ ID NO 93
<211> LENGTH: 11
<212> TYPE: PRT
<213> ORGANISM: Homo sapiens

<400> SEQUENCE: 93

```
Ala Gln Asp Val Ile Ser Glu Ala Trp Phe Pro
1               5                   10
```

<210> SEQ ID NO 94
<211> LENGTH: 11
<212> TYPE: PRT
<213> ORGANISM: Homo sapiens

<400> SEQUENCE: 94

```
Pro Asn Leu Val Ala Ala Leu Pro Pro Ser Thr
1               5                   10
```

<210> SEQ ID NO 95
<211> LENGTH: 11
<212> TYPE: PRT
<213> ORGANISM: Homo sapiens

<400> SEQUENCE: 95

```
Pro Asn Leu Val Ala Thr Leu Pro Pro Ser Thr
1               5                   10
```

<210> SEQ ID NO 96
<211> LENGTH: 11
<212> TYPE: PRT
<213> ORGANISM: Homo sapiens

<400> SEQUENCE: 96

```
Arg Met Ala Thr Ala Ile Ala Arg Cys Ala Pro
1               5                   10
```

<210> SEQ ID NO 97
<211> LENGTH: 11
<212> TYPE: PRT
<213> ORGANISM: Homo sapiens

<400> SEQUENCE: 97

Arg Met Ala Thr Ala Val Ala Arg Cys Ala Pro
1               5                   10

<210> SEQ ID NO 98
<211> LENGTH: 11
<212> TYPE: PRT
<213> ORGANISM: Homo sapiens

<400> SEQUENCE: 98

Cys Ala Pro Asp Glu Glu Leu Leu Ser Cys Ser
1               5                   10

<210> SEQ ID NO 99
<211> LENGTH: 11
<212> TYPE: PRT
<213> ORGANISM: Homo sapiens

<400> SEQUENCE: 99

Cys Ala Pro Asp Glu Gly Leu Leu Ser Cys Ser
1               5                   10

<210> SEQ ID NO 100
<211> LENGTH: 11
<212> TYPE: PRT
<213> ORGANISM: Homo sapiens

<400> SEQUENCE: 100

Arg Ala His Asn Ala Phe Gly Gly Glu Gly Val
1               5                   10

<210> SEQ ID NO 101
<211> LENGTH: 11
<212> TYPE: PRT
<213> ORGANISM: Homo sapiens

<400> SEQUENCE: 101

Arg Ala His Asn Ala Leu Gly Gly Glu Gly Val
1               5                   10

<210> SEQ ID NO 102
<211> LENGTH: 11
<212> TYPE: PRT
<213> ORGANISM: Homo sapiens

<400> SEQUENCE: 102

Gly Glu Gly Val Tyr Ala Ile Ala Arg Cys Cys
1               5                   10

<210> SEQ ID NO 103
<211> LENGTH: 11
<212> TYPE: PRT
<213> ORGANISM: Homo sapiens

<400> SEQUENCE: 103

Gly Glu Gly Val Tyr Thr Ile Ala Arg Cys Cys
1               5                   10

<210> SEQ ID NO 104
<211> LENGTH: 11

```
<212> TYPE: PRT
<213> ORGANISM: Homo sapiens

<400> SEQUENCE: 104

Thr Arg Val His Cys His Gln Gln Gly His Val
1               5                   10

<210> SEQ ID NO 105
<211> LENGTH: 11
<212> TYPE: PRT
<213> ORGANISM: Homo sapiens

<400> SEQUENCE: 105

Thr Arg Val His Cys Arg Gln Gln Gly His Val
1               5                   10

<210> SEQ ID NO 106
<211> LENGTH: 11
<212> TYPE: PRT
<213> ORGANISM: Homo sapiens

<400> SEQUENCE: 106

Arg Val His Cys His Gln Gln Gly His Val Leu
1               5                   10

<210> SEQ ID NO 107
<211> LENGTH: 11
<212> TYPE: PRT
<213> ORGANISM: Homo sapiens

<400> SEQUENCE: 107

Arg Val His Cys His Glu Gln Gly His Val Leu
1               5                   10

<210> SEQ ID NO 108
<211> LENGTH: 11
<212> TYPE: PRT
<213> ORGANISM: Homo sapiens

<400> SEQUENCE: 108

Lys Glu His Gly Ile Pro Ala Pro Gln Glu Gln
1               5                   10

<210> SEQ ID NO 109
<211> LENGTH: 11
<212> TYPE: PRT
<213> ORGANISM: Homo sapiens

<400> SEQUENCE: 109

Lys Glu His Gly Ile Leu Ala Pro Gln Glu Gln
1               5                   10

<210> SEQ ID NO 110
<211> LENGTH: 11
<212> TYPE: PRT
<213> ORGANISM: Homo sapiens

<400> SEQUENCE: 110

Gly Ile Pro Ala Pro Gln Glu Gln Val Thr Val
1               5                   10

<210> SEQ ID NO 111
<211> LENGTH: 11
<212> TYPE: PRT
<213> ORGANISM: Homo sapiens
```

```
<400> SEQUENCE: 111

Gly Ile Pro Ala Pro Pro Glu Gln Val Thr Val
1               5                   10

<210> SEQ ID NO 112
<211> LENGTH: 11
<212> TYPE: PRT
<213> ORGANISM: Homo sapiens

<400> SEQUENCE: 112

Gly Ser Thr Ser Glu Glu Ala Val Thr Ala Val
1               5                   10

<210> SEQ ID NO 113
<211> LENGTH: 11
<212> TYPE: PRT
<213> ORGANISM: Homo sapiens

<400> SEQUENCE: 113

Gly Ser Thr Ser Glu Gly Ala Val Thr Ala Val
1               5                   10

<210> SEQ ID NO 114
<211> LENGTH: 6
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (2)..(5)
<223> OTHER INFORMATION: Xaa can be any naturally occurring amino acid

<400> SEQUENCE: 114

Lys Xaa Xaa Xaa Xaa Arg
1               5

<210> SEQ ID NO 115
<211> LENGTH: 6
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be arginine or lysine
<220> FEATURE:
<221> NAME/KEY: misc_feature
<222> LOCATION: (5)..(5)
<223> OTHER INFORMATION: Xaa can be glutamate or aspartate

<400> SEQUENCE: 115

Arg Xaa Xaa Arg Xaa Leu
1               5

<210> SEQ ID NO 116
<211> LENGTH: 4
<212> TYPE: PRT
<213> ORGANISM: Artificial sequence
<220> FEATURE:
<223> OTHER INFORMATION: Synthetic Construct

<400> SEQUENCE: 116

Val Phe Ala Gln
```

<210> SEQ ID NO 117
<211> LENGTH: 11
<212> TYPE: PRT
<213> ORGANISM: Artificial sequence
<220> FEATURE:
<223> OTHER INFORMATION: Synthetic Construct

<400> SEQUENCE: 117

Ser Ser Val Phe Ala Gln Ser Ile Pro Trp Asn
1               5                   10

<210> SEQ ID NO 118
<211> LENGTH: 860
<212> TYPE: PRT
<213> ORGANISM: Homo sapiens

<400> SEQUENCE: 118

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
        50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

-continued

```
Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735
```

```
Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
                820                 825                 830

Glu Asp Glu Val His Ile Cys His Asn Gln Asp Gly Tyr Ser Tyr Pro
                835                 840                 845

Ser Arg Gln Met Val Ser Leu Glu Asp Asp Val Ala
                850                 855                 860

<210> SEQ ID NO 119
<211> LENGTH: 873
<212> TYPE: PRT
<213> ORGANISM: Homo sapiens

<400> SEQUENCE: 119

Met Gly Thr Ser Ala Leu Trp Ala Leu Trp Leu Leu Leu Ala Leu Cys
1               5                   10                  15

Trp Ala Pro Arg Glu Ser Gly Ala Thr Gly Thr Gly Arg Lys Ala Lys
                20                  25                  30

Cys Glu Pro Ser Gln Phe Gln Cys Thr Asn Gly Arg Cys Ile Thr Leu
            35                  40                  45

Leu Trp Lys Cys Asp Gly Asp Glu Asp Cys Val Asp Gly Ser Asp Glu
    50                  55                  60

Lys Asn Cys Val Lys Lys Thr Cys Ala Glu Ser Asp Phe Val Cys Asn
65                  70                  75                  80

Asn Gly Gln Cys Val Pro Ser Arg Trp Lys Cys Asp Gly Asp Pro Asp
                85                  90                  95

Cys Glu Asp Gly Ser Asp Glu Ser Pro Glu Gln Cys His Met Arg Thr
            100                 105                 110

Cys Arg Ile His Glu Ile Ser Cys Gly Ala His Ser Thr Gln Cys Ile
        115                 120                 125

Pro Val Ser Trp Arg Cys Asp Gly Glu Asn Asp Cys Asp Ser Gly Glu
    130                 135                 140

Asp Glu Glu Asn Cys Gly Asn Ile Thr Cys Ser Pro Asp Glu Phe Thr
145                 150                 155                 160

Cys Ser Ser Gly Arg Cys Ile Ser Arg Asn Phe Val Cys Asn Gly Gln
                165                 170                 175

Asp Asp Cys Ser Asp Gly Ser Asp Glu Leu Asp Cys Ala Pro Pro Thr
            180                 185                 190

Cys Gly Ala His Glu Phe Gln Cys Ser Thr Ser Ser Cys Ile Pro Ile
        195                 200                 205

Ser Trp Val Cys Asp Asp Asp Ala Asp Cys Ser Asp Gln Ser Asp Glu
    210                 215                 220

Ser Leu Glu Gln Cys Gly Arg Gln Pro Val Ile His Thr Lys Cys Pro
225                 230                 235                 240

Ala Ser Glu Ile Gln Cys Gly Ser Gly Glu Cys Ile His Lys Lys Trp
                245                 250                 255
```

```
Arg Cys Asp Gly Asp Pro Asp Cys Lys Asp Gly Ser Asp Glu Val Asn
            260                 265                 270
Cys Pro Ser Arg Thr Cys Arg Pro Asp Gln Phe Glu Cys Glu Asp Gly
            275                 280                 285
Ser Cys Ile His Gly Ser Arg Gln Cys Asn Gly Ile Arg Asp Cys Val
            290                 295                 300
Asp Gly Ser Asp Glu Val Asn Cys Lys Asn Val Asn Gln Cys Leu Gly
305                 310                 315                 320
Pro Gly Lys Phe Lys Cys Arg Ser Gly Glu Cys Ile Asp Ile Ser Lys
            325                 330                 335
Val Cys Asn Gln Glu Gln Asp Cys Arg Asp Trp Ser Asp Glu Pro Leu
            340                 345                 350
Lys Glu Cys His Ile Asn Glu Cys Leu Val Asn Asn Gly Gly Cys Ser
            355                 360                 365
His Ile Cys Lys Asp Leu Val Ile Gly Tyr Glu Cys Asp Cys Ala Ala
            370                 375                 380
Gly Phe Glu Leu Ile Asp Arg Lys Thr Cys Gly Asp Ile Asp Glu Cys
385                 390                 395                 400
Gln Asn Pro Gly Ile Cys Ser Gln Ile Cys Ile Asn Leu Lys Gly Gly
            405                 410                 415
Tyr Lys Cys Glu Cys Ser Arg Gly Tyr Gln Met Asp Leu Ala Thr Gly
            420                 425                 430
Val Cys Lys Ala Val Gly Lys Glu Pro Ser Leu Ile Phe Thr Asn Arg
            435                 440                 445
Arg Asp Ile Arg Lys Ile Gly Leu Glu Arg Lys Glu Tyr Ile Gln Leu
            450                 455                 460
Val Glu Gln Leu Arg Asn Thr Val Ala Leu Asp Ala Asp Ile Ala Ala
465                 470                 475                 480
Gln Lys Leu Phe Trp Ala Asp Leu Ser Gln Lys Ala Ile Phe Ser Ala
            485                 490                 495
Ser Ile Asp Asp Lys Val Gly Arg His Val Lys Met Ile Asp Asn Val
            500                 505                 510
Tyr Asn Pro Ala Ala Ile Ala Val Asp Trp Val Tyr Lys Thr Ile Tyr
            515                 520                 525
Trp Thr Asp Ala Ala Ser Lys Thr Ile Ser Val Ala Thr Leu Asp Gly
            530                 535                 540
Thr Lys Arg Lys Phe Leu Phe Asn Ser Asp Leu Arg Glu Pro Ala Ser
545                 550                 555                 560
Ile Ala Val Asp Pro Leu Ser Gly Phe Val Tyr Trp Ser Asp Trp Gly
            565                 570                 575
Glu Pro Ala Lys Ile Glu Lys Ala Gly Met Asn Gly Phe Asp Arg Arg
            580                 585                 590
Pro Leu Val Thr Ala Asp Ile Gln Trp Pro Asn Gly Ile Thr Leu Asp
            595                 600                 605
Leu Ile Lys Ser Arg Leu Tyr Trp Leu Asp Ser Lys Leu His Met Leu
            610                 615                 620
Ser Ser Val Asp Leu Asn Gly Gln Asp Arg Arg Ile Val Leu Lys Ser
625                 630                 635                 640
Leu Glu Phe Leu Ala His Pro Leu Ala Leu Thr Ile Phe Glu Asp Arg
            645                 650                 655
Val Tyr Trp Ile Asp Gly Glu Asn Glu Ala Val Tyr Gly Ala Asn Lys
            660                 665                 670
Phe Thr Gly Ser Glu Leu Ala Thr Leu Val Asn Asn Leu Asn Asp Ala
```

```
                675                 680                 685
Gln Asp Ile Ile Val Tyr His Glu Leu Val Gln Pro Ser Gly Lys Asn
            690                 695                 700
Trp Cys Glu Glu Asp Met Glu Asn Gly Gly Cys Glu Tyr Leu Cys Leu
705                 710                 715                 720
Pro Ala Pro Gln Ile Asn Asp His Ser Pro Lys Tyr Thr Cys Ser Cys
                725                 730                 735
Pro Ser Gly Tyr Asn Val Glu Glu Asn Gly Arg Asp Cys Gln Ser Thr
            740                 745                 750
Ala Thr Thr Val Thr Tyr Ser Glu Thr Lys Asp Thr Asn Thr Thr Glu
            755                 760                 765
Ile Ser Ala Thr Ser Gly Leu Val Pro Gly Gly Ile Asn Val Thr Thr
770                 775                 780
Ala Val Ser Glu Val Ser Val Pro Pro Lys Gly Thr Ser Ala Ala Trp
785                 790                 795                 800
Ala Ile Leu Pro Leu Leu Leu Leu Val Met Ala Ala Val Gly Gly Tyr
            805                 810                 815
Leu Met Trp Arg Asn Trp Gln His Lys Asn Met Lys Ser Met Asn Phe
            820                 825                 830
Asp Asn Pro Val Tyr Leu Lys Thr Thr Glu Glu Asp Leu Ser Ile Asp
            835                 840                 845
Ile Gly Arg His Ser Ala Ser Val Gly His Thr Tyr Pro Ala Ile Ser
850                 855                 860
Val Val Ser Thr Asp Asp Leu Ala
865                 870

<210> SEQ ID NO 120
<211> LENGTH: 793
<212> TYPE: PRT
<213> ORGANISM: Homo sapiens

<400> SEQUENCE: 120

Met Gly Leu Pro Glu Pro Gly Pro Leu Arg Leu Leu Ala Leu Leu Leu
1               5                   10                  15
Leu Leu Leu Leu Leu Leu Leu Leu Gln Leu Gln His Leu Ala Ala Ala
                20                  25                  30
Ala Ala Asp Pro Leu Leu Gly Gly Gln Gly Pro Ala Lys Asp Cys Glu
            35                  40                  45
Lys Asp Gln Phe Gln Cys Arg Asn Glu Arg Cys Ile Pro Ser Val Trp
        50                  55                  60
Arg Cys Asp Glu Asp Asp Asp Cys Leu Asp His Ser Asp Glu Asp Asp
65                  70                  75                  80
Cys Pro Lys Lys Thr Cys Ala Asp Ser Asp Phe Thr Cys Asp Asn Gly
                85                  90                  95
His Cys Ile His Glu Arg Trp Lys Cys Asp Gly Glu Glu Glu Cys Pro
            100                 105                 110
Asp Gly Ser Asp Glu Ser Glu Ala Thr Cys Thr Lys Gln Val Cys Pro
        115                 120                 125
Ala Glu Lys Leu Ser Cys Gly Pro Thr Ser His Lys Cys Val Pro Ala
    130                 135                 140
Ser Trp Arg Cys Asp Gly Glu Lys Asp Cys Glu Gly Gly Ala Asp Glu
145                 150                 155                 160
Ala Gly Cys Ala Thr Trp Leu Asn Glu Cys Leu His Asn Asn Gly Gly
                165                 170                 175
Cys Ser His Ile Cys Thr Asp Leu Lys Ile Gly Phe Glu Cys Thr Cys
```

-continued

Pro Ala Gly Phe Gln Leu Leu Asp Gln Lys Thr Cys Gly Asp Ile Asp
                    180                 185                 190
195

Glu Cys Lys Asp Pro Asp Ala Cys Ser Gln Ile Cys Val Asn Tyr Lys
        210                 215                 220

Gly Tyr Phe Lys Cys Glu Cys Tyr Pro Gly Tyr Glu Met Asp Leu Leu
225                 230                 235                 240

Thr Lys Asn Cys Lys Ala Ala Gly Lys Ser Pro Ser Leu Ile Phe
            245                 250                 255

Thr Asn Arg His Glu Val Arg Arg Ile Asp Leu Val Lys Arg Asn Tyr
                260                 265                 270

Ser Arg Leu Ile Pro Met Leu Lys Asn Val Val Ala Leu Asp Val Glu
        275                 280                 285

Val Ala Thr Asn Arg Ile Tyr Trp Cys Asp Leu Ser Tyr Arg Lys Ile
        290                 295                 300

Tyr Ser Ala Tyr Met Asp Lys Ala Ser Asp Pro Lys Glu Gln Glu Val
305                 310                 315                 320

Leu Ile Asp Glu Gln Leu His Ser Pro Glu Gly Leu Ala Val Asp Trp
                325                 330                 335

Val His Lys His Ile Tyr Trp Thr Asp Ser Gly Asn Lys Thr Ile Ser
                340                 345                 350

Val Ala Thr Val Asp Gly Gly Arg Arg Thr Leu Phe Ser Arg Asn
        355                 360                 365

Leu Ser Glu Pro Arg Ala Ile Ala Val Asp Pro Leu Arg Gly Phe Met
        370                 375                 380

Tyr Trp Ser Asp Trp Gly Asp Gln Ala Lys Ile Glu Lys Ser Gly Leu
385                 390                 395                 400

Asn Gly Val Asp Arg Gln Thr Leu Val Ser Asp Asn Ile Glu Trp Pro
                405                 410                 415

Asn Gly Ile Thr Leu Asp Leu Leu Ser Gln Arg Leu Tyr Trp Val Asp
                420                 425                 430

Ser Lys Leu His Gln Leu Ser Ser Ile Asp Phe Ser Gly Gly Asn Arg
        435                 440                 445

Lys Thr Leu Ile Ser Ser Thr Asp Phe Leu Ser His Pro Phe Gly Ile
        450                 455                 460

Ala Val Phe Glu Asp Lys Val Phe Trp Thr Asp Leu Glu Asn Glu Ala
465                 470                 475                 480

Ile Phe Ser Ala Asn Arg Leu Asn Gly Leu Glu Ile Ser Ile Leu Ala
                485                 490                 495

Glu Asn Leu Asn Asn Pro His Asp Ile Val Ile Phe His Glu Leu Lys
                500                 505                 510

Gln Pro Arg Ala Pro Asp Ala Cys Glu Leu Ser Val Gln Pro Asn Gly
        515                 520                 525

Gly Cys Glu Tyr Leu Cys Leu Pro Ala Pro Gln Ile Ser Ser His Ser
        530                 535                 540

Pro Lys Tyr Thr Cys Ala Cys Pro Asp Thr Met Trp Leu Gly Pro Asp
545                 550                 555                 560

Met Lys Arg Cys Tyr Arg Ala Pro Gln Ser Thr Ser Thr Thr Thr Leu
                565                 570                 575

Ala Ser Thr Met Thr Arg Thr Val Pro Ala Thr Thr Arg Ala Pro Gly
                580                 585                 590

Thr Thr Val His Arg Ser Thr Tyr Gln Asn His Ser Thr Glu Thr Pro
        595                 600                 605

-continued

```
Ser Leu Thr Ala Ala Val Pro Ser Val Ser Val Pro Arg Ala Pro
    610                 615                 620

Ser Ile Ser Pro Ser Thr Leu Ser Pro Ala Thr Ser Asn His Ser Gln
625                 630                 635                 640

His Tyr Ala Asn Glu Asp Ser Lys Met Gly Ser Thr Val Thr Ala Ala
                645                 650                 655

Val Ile Gly Ile Ile Val Pro Ile Val Val Ile Ala Leu Leu Cys Met
            660                 665                 670

Ser Gly Tyr Leu Ile Trp Arg Asn Trp Lys Arg Lys Asn Thr Lys Ser
        675                 680                 685

Met Asn Phe Asp Asn Pro Val Tyr Arg Lys Thr Thr Glu Glu Glu Asp
    690                 695                 700

Glu Asp Glu Leu His Ile Gly Arg Thr Ala Gln Ile Gly His Val Tyr
705                 710                 715                 720

Pro Ala Ala Ile Ser Ser Phe Asp Arg Pro Leu Trp Ala Glu Pro Cys
                725                 730                 735

Leu Gly Glu Thr Arg Glu Pro Glu Asp Pro Ala Pro Ala Leu Lys Glu
            740                 745                 750

Leu Phe Val Leu Pro Gly Glu Pro Arg Ser Gln Leu His Gln Leu Pro
        755                 760                 765

Lys Asn Pro Leu Ser Glu Leu Pro Val Val Lys Ser Lys Arg Val Ala
    770                 775                 780

Leu Ser Leu Glu Asp Asp Gly Leu Pro
785                 790
```

```
<210> SEQ ID NO 121
<211> LENGTH: 34
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(10)
<223> OTHER INFORMATION: Xaa can be any naturally occurring amino acid
<220> FEATURE:
<221> NAME/KEY: MISC_FEATURE
<222> LOCATION: (15)..(18)
<223> OTHER INFORMATION: Xaa is any naturally occurring amino acid or is
      absent
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(33)
<223> OTHER INFORMATION: Xaa can be any naturally occurring amino acid

<400> SEQUENCE: 121

Met Gly Xaa Xaa Xaa Ser Xaa Xaa Xaa Trp Pro Leu Pro Xaa Xaa
1               5                   10                  15

Xaa Xaa Xaa Xaa Leu Leu Leu Leu Leu Leu Leu Xaa Pro Xaa Gly Xaa
                20                  25                  30
```

Xaa Ala

```
<210> SEQ ID NO 122
<211> LENGTH: 662
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid or is
      absent
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (70)..(71)
<223> OTHER INFORMATION: Xaa can be any naturally occurring amino acid
<220> FEATURE:
```

```
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (134)..(139)
<223> OTHER INFORMATION: Xaa can be any naturally occurring amino acid
<220> FEATURE:
<221> NAME/KEY: misc_feature
<222> LOCATION: (141)..(143)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (161)..(162)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
<221> NAME/KEY: misc_feature
<222> LOCATION: (176)..(177)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (217)..(218)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
```

```
<221> NAME/KEY: misc_feature
<222> LOCATION: (250)..(250)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (272)..(273)
<223> OTHER INFORMATION: Xaa can be any naturally occurring amino acid
<220> FEATURE:
<221> NAME/KEY: misc_feature
<222> LOCATION: (277)..(277)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (336)..(336)
<223> OTHER INFORMATION: Xaa can be any naturally occurring amino acid
<220> FEATURE:
<221> NAME/KEY: misc_feature
<222> LOCATION: (349)..(350)
<223> OTHER INFORMATION: Xaa can be any naturally occurring amino acid
<220> FEATURE:
<221> NAME/KEY: misc_feature
<222> LOCATION: (366)..(366)
<223> OTHER INFORMATION: Xaa can be any naturally occurring amino acid
<220> FEATURE:
<221> NAME/KEY: misc_feature
<222> LOCATION: (371)..(373)
<223> OTHER INFORMATION: Xaa can be any naturally occurring amino acid
<220> FEATURE:
<221> NAME/KEY: misc_feature
<222> LOCATION: (375)..(375)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (390)..(390)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid
<220> FEATURE:
<221> NAME/KEY: misc_feature
<222> LOCATION: (404)..(404)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (413)..(413)
<223> OTHER INFORMATION: Xaa can be any naturally occurring amino acid
<220> FEATURE:
<221> NAME/KEY: misc_feature
<222> LOCATION: (419)..(421)
<223> OTHER INFORMATION: Xaa can be any naturally occurring amino acid
<220> FEATURE:
<221> NAME/KEY: misc_feature
<222> LOCATION: (423)..(423)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
```

```
<221> NAME/KEY: misc_feature
<222> LOCATION: (440)..(440)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (450)..(450)
<223> OTHER INFORMATION: Xaa can be any naturally occurring amino acid
<220> FEATURE:
<221> NAME/KEY: misc_feature
<222> LOCATION: (464)..(464)
<223> OTHER INFORMATION: Xaa can be any naturally occurring amino acid
<220> FEATURE:
<221> NAME/KEY: misc_feature
<222> LOCATION: (468)..(470)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (476)..(477)
<223> OTHER INFORMATION: Xaa can be any naturally occurring amino acid
<220> FEATURE:
<221> NAME/KEY: misc_feature
<222> LOCATION: (480)..(480)
<223> OTHER INFORMATION: Xaa can be any naturally occurring amino acid
<220> FEATURE:
<221> NAME/KEY: misc_feature
<222> LOCATION: (482)..(482)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid
<220> FEATURE:
<221> NAME/KEY: misc_feature
<222> LOCATION: (501)..(502)
<223> OTHER INFORMATION: Xaa can be any naturally occurring amino acid
<220> FEATURE:
<221> NAME/KEY: misc_feature
<222> LOCATION: (506)..(506)
<223> OTHER INFORMATION: Xaa can be any naturally occurring amino acid
<220> FEATURE:
<221> NAME/KEY: misc_feature
<222> LOCATION: (508)..(509)
<223> OTHER INFORMATION: Xaa can be any naturally occurring amino acid
<220> FEATURE:
<221> NAME/KEY: misc_feature
<222> LOCATION: (511)..(511)
<223> OTHER INFORMATION: Xaa can be any naturally occurring amino acid
<220> FEATURE:
<221> NAME/KEY: misc_feature
<222> LOCATION: (513)..(513)
<223> OTHER INFORMATION: Xaa can be any naturally occurring amino acid
<220> FEATURE:
<221> NAME/KEY: misc_feature
<222> LOCATION: (515)..(517)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid
<220> FEATURE:
<221> NAME/KEY: misc_feature
<222> LOCATION: (525)..(526)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
```

```
<221> NAME/KEY: misc_feature
<222> LOCATION: (540)..(540)
<223> OTHER INFORMATION: Xaa can be any naturally occurring amino acid
<220> FEATURE:
<221> NAME/KEY: misc_feature
<222> LOCATION: (542)..(546)
<223> OTHER INFORMATION: Xaa can be any naturally occurring amino acid
<220> FEATURE:
<221> NAME/KEY: misc_feature
<222> LOCATION: (548)..(548)
<223> OTHER INFORMATION: Xaa can be any naturally occurring amino acid
<220> FEATURE:
<221> NAME/KEY: misc_feature
<222> LOCATION: (551)..(551)
<223> OTHER INFORMATION: Xaa can be any naturally occurring amino acid
<220> FEATURE:
<221> NAME/KEY: misc_feature
<222> LOCATION: (553)..(553)
<223> OTHER INFORMATION: Xaa can be any naturally occurring amino acid
<220> FEATURE:
<221> NAME/KEY: misc_feature
<222> LOCATION: (556)..(556)
<223> OTHER INFORMATION: Xaa can be any naturally occurring amino acid
<220> FEATURE:
<221> NAME/KEY: misc_feature
<222> LOCATION: (562)..(563)
<223> OTHER INFORMATION: Xaa can be any naturally occurring amino acid
<220> FEATURE:
<221> NAME/KEY: misc_feature
<222> LOCATION: (566)..(567)
<223> OTHER INFORMATION: Xaa can be any naturally occurring amino acid
<220> FEATURE:
<221> NAME/KEY: misc_feature
<222> LOCATION: (572)..(572)
<223> OTHER INFORMATION: Xaa can be any naturally occurring amino acid
<220> FEATURE:
<221> NAME/KEY: misc_feature
<222> LOCATION: (580)..(580)
<223> OTHER INFORMATION: Xaa can be any naturally occurring amino acid
<220> FEATURE:
<221> NAME/KEY: misc_feature
<222> LOCATION: (586)..(587)
<223> OTHER INFORMATION: Xaa can be any naturally occurring amino acid
<220> FEATURE:
<221> NAME/KEY: misc_feature
<222> LOCATION: (589)..(589)
<223> OTHER INFORMATION: Xaa can be any naturally occurring amino acid
<220> FEATURE:
<221> NAME/KEY: misc_feature
<222> LOCATION: (598)..(598)
<223> OTHER INFORMATION: Xaa can be any naturally occurring amino acid
<220> FEATURE:
<221> NAME/KEY: misc_feature
<222> LOCATION: (606)..(607)
<223> OTHER INFORMATION: Xaa can be any naturally occurring amino acid
<220> FEATURE:
<221> NAME/KEY: misc_feature
<222> LOCATION: (611)..(611)
<223> OTHER INFORMATION: Xaa can be any naturally occurring amino acid
<220> FEATURE:
<221> NAME/KEY: misc_feature
<222> LOCATION: (613)..(614)
<223> OTHER INFORMATION: Xaa can be any naturally occurring amino acid
<220> FEATURE:
<221> NAME/KEY: misc_feature
<222> LOCATION: (619)..(619)
<223> OTHER INFORMATION: Xaa can be any naturally occurring amino acid
<220> FEATURE:
<221> NAME/KEY: misc_feature
<222> LOCATION: (623)..(623)
<223> OTHER INFORMATION: Xaa can be any naturally occurring amino acid
<220> FEATURE:
<221> NAME/KEY: misc_feature
<222> LOCATION: (626)..(626)
<223> OTHER INFORMATION: Xaa can be any naturally occurring amino acid
<220> FEATURE:
<221> NAME/KEY: misc_feature
<222> LOCATION: (628)..(629)
<223> OTHER INFORMATION: Xaa can be any naturally occurring amino acid
<220> FEATURE:
```

<221> NAME/KEY: misc_feature
<222> LOCATION: (631)..(636)
<223> OTHER INFORMATION: Xaa can be any naturally occurring amino acid
<220> FEATURE:
<221> NAME/KEY: misc_feature
<222> LOCATION: (639)..(640)
<223> OTHER INFORMATION: Xaa can be any naturally occurring amino acid
<220> FEATURE:
<221> NAME/KEY: misc_feature
<222> LOCATION: (642)..(643)
<223> OTHER INFORMATION: Xaa can be any naturally occurring amino acid
<220> FEATURE:
<221> NAME/KEY: misc_feature
<222> LOCATION: (645)..(645)
<223> OTHER INFORMATION: Xaa can be any naturally occurring amino acid
<220> FEATURE:
<221> NAME/KEY: misc_feature
<222> LOCATION: (653)..(654)
<223> OTHER INFORMATION: Xaa can be any naturally occurring amino acid
<220> FEATURE:
<221> NAME/KEY: misc_feature
<222> LOCATION: (656)..(656)
<223> OTHER INFORMATION: Xaa can be any naturally occurring amino acid
<220> FEATURE:
<221> NAME/KEY: MISC_FEATURE
<222> LOCATION: (659)..(662)
<223> OTHER INFORMATION: Xaa is any naturally occurring amino acid or is absent

<400> SEQUENCE: 122

```
Gln Xaa Asp Glu Asp Gly Asp Tyr Glu Glu Leu Xaa Leu Ala Leu Xaa
1               5                   10                  15

Ser Xaa Glu Asp Xaa Leu Xaa Xaa Xaa Xaa His Xaa Xaa Thr Ala
            20                  25                  30

Thr Phe Xaa Arg Cys Xaa Lys Xaa Xaa Trp Arg Leu Pro Gly Thr Tyr
        35                  40                  45

Xaa Val Val Leu Xaa Glu Glu Thr Xaa Xaa Xaa Gln Xaa Glu Xaa Thr
50                  55                  60

Ala Xaa Arg Leu Gln Xaa Xaa Ala Ala Arg Gly Tyr Xaa Xaa Lys
65                  70                  75                  80

Xaa Leu His Xaa Phe Xaa Xaa Leu Xaa Pro Gly Phe Leu Val Lys Met
                85                  90                  95

Ser Xaa Asp Leu Leu Xaa Leu Ala Leu Lys Leu Pro His Val Xaa Tyr
            100                 105                 110

Ile Glu Glu Asp Ser Xaa Val Phe Ala Gln Ser Ile Pro Trp Asn Leu
            115                 120                 125

Glu Arg Ile Xaa Pro Xaa Xaa Xaa Xaa Xaa Glu Xaa Xaa Xaa Pro
130                 135                 140

Asp Gly Xaa Ser Xaa Val Glu Val Tyr Leu Leu Asp Thr Ser Ile Gln
145                 150                 155                 160

Xaa Xaa His Arg Glu Ile Glu Gly Arg Val Xaa Xaa Thr Asp Phe Xaa
                165                 170                 175

Xaa Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
            195                 200                 205

Ala Gly Val Ala Lys Gly Xaa Ser Xaa Xaa Ser Leu Arg Val Leu Asn
210                 215                 220

Cys Gln Gly Lys Gly Thr Val Ser Gly Thr Leu Ile Gly Leu Glu Phe
225                 230                 235                 240

Ile Arg Lys Ser Gln Leu Xaa Gln Pro Xaa Gly Pro Leu Val Val Leu
            245                 250                 255

Leu Pro Leu Ala Gly Gly Tyr Ser Arg Xaa Leu Asn Xaa Ala Cys Xaa
```

```
                    260                 265                 270
Xaa Leu Ala Arg Xaa Gly Val Val Leu Val Xaa Ala Ala Gly Asn Phe
                275                 280                 285

Arg Asp Asp Ala Cys Leu Tyr Ser Pro Ala Ser Ala Pro Glu Val Ile
290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Xaa
                325                 330                 335

Asp Ile Ile Gly Ala Ser Ser Asp Cys Ser Thr Cys Xaa Xaa Ser Gln
                340                 345                 350

Ser Gly Thr Ser Gln Ala Ala His Val Ala Gly Ile Xaa Ala Met
                355                 360                 365

Met Leu Xaa Xaa Xaa Pro Xaa Leu Thr Leu Ala Glu Leu Arg Gln Arg
        370                 375                 380

Leu Ile Xaa Phe Ser Xaa Lys Asp Val Ile Asn Xaa Ala Trp Phe Pro
385                 390                 395                 400

Glu Asp Gln Xaa Val Leu Thr Pro Asn Xaa Val Ala Xaa Leu Pro Pro
                405                 410                 415

Ser Thr Xaa Xaa Xaa Gly Xaa Gln Leu Xaa Cys Arg Thr Val Trp Ser
                420                 425                 430

Ala His Ser Gly Pro Thr Arg Xaa Ala Thr Ala Xaa Ala Arg Cys Ala
        435                 440                 445

Pro Xaa Glu Glu Leu Leu Ser Cys Ser Ser Phe Ser Arg Ser Gly Xaa
    450                 455                 460

Arg Arg Gly Xaa Xaa Xaa Glu Ala Xaa Gly Gly Xaa Xaa Val Cys Xaa
465                 470                 475                 480

Ala Xaa Asn Ala Phe Gly Gly Glu Gly Val Tyr Ala Xaa Ala Arg Cys
                485                 490                 495

Cys Leu Xaa Pro Xaa Xaa Asn Cys Ser Xaa His Xaa Xaa Pro Xaa Ala
            500                 505                 510

Xaa Ala Xaa Xaa Xaa Thr Xaa Val His Cys His Gln Xaa Xaa His Val
        515                 520                 525

Leu Thr Gly Cys Ser Xaa His Trp Glu Val Glu Xaa Leu Xaa Xaa Xaa
        530                 535                 540

Xaa Xaa Pro Xaa Leu Arg Xaa Arg Xaa Gln Pro Xaa Gln Cys Val Gly
545                 550                 555                 560

His Xaa Xaa Ala Ser Xaa Xaa Ala Ser Cys Cys Xaa Ala Pro Gly Leu
                565                 570                 575

Glu Cys Lys Xaa Lys Glu His Gly Ile Xaa Xaa Pro Xaa Glu Gln Val
            580                 585                 590

Thr Val Ala Cys Glu Xaa Gly Trp Thr Leu Thr Gly Cys Xaa Xaa Leu
        595                 600                 605

Pro Gly Xaa Ser Xaa Xaa Leu Gly Ala Tyr Xaa Val Asp Asn Xaa Cys
        610                 615                 620

Val Xaa Arg Xaa Xaa Asp Xaa Xaa Xaa Xaa Xaa Thr Ser Xaa Xaa
625                 630                 635                 640

Ala Xaa Xaa Ala Xaa Ala Ile Cys Cys Arg Ser Arg Xaa Xaa Ala Xaa
            645                 650                 655

Ala Ser Xaa Xaa Xaa Xaa
            660

<210> SEQ ID NO 123
<211> LENGTH: 122
```

```
<212> TYPE: PRT
<213> ORGANISM: Artificial sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid or is
      absent
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(59)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (70)..(71)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(81)
```

```
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid

<400> SEQUENCE: 123

Gln Xaa Asp Glu Asp Gly Asp Tyr Glu Glu Leu Xaa Leu Ala Leu Xaa
1               5                   10                  15

Ser Xaa Glu Asp Xaa Leu Xaa Xaa Xaa Xaa His Xaa Xaa Thr Ala
        20                  25                  30

Thr Phe Xaa Arg Cys Xaa Lys Xaa Xaa Trp Arg Leu Pro Gly Thr Tyr
        35                  40                  45

Xaa Val Val Leu Xaa Glu Glu Thr Xaa Xaa Xaa Gln Xaa Glu Xaa Thr
    50                  55                  60

Ala Xaa Arg Leu Gln Xaa Xaa Ala Ala Arg Arg Gly Tyr Xaa Xaa Lys
65              70                  75                  80

Xaa Leu His Xaa Phe Xaa Xaa Leu Xaa Pro Gly Phe Leu Val Lys Met
            85                  90                  95

Ser Xaa Asp Leu Leu Xaa Leu Ala Leu Lys Leu Pro His Val Xaa Tyr
        100                 105                 110

Ile Glu Glu Asp Ser Xaa Val Phe Ala Gln
        115                 120

<210> SEQ ID NO 124
<211> LENGTH: 540
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
```

```
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(96)
<223> OTHER INFORMATION: Xaa can be any naturally occurring amino acid
<220> FEATURE:
<221> NAME/KEY: misc_feature
<222> LOCATION: (125)..(125)
<223> OTHER INFORMATION: Xaa can be any naturally occurring amino acid
<220> FEATURE:
<221> NAME/KEY: misc_feature
<222> LOCATION: (128)..(128)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (150)..(151)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (161)..(161)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (227)..(228)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (249)..(251)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
```

```
<221> NAME/KEY: misc_feature
<222> LOCATION: (274)..(274)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (291)..(291)
<223> OTHER INFORMATION: Xaa can be any naturally occurring amino acid
<220> FEATURE:
<221> NAME/KEY: misc_feature
<222> LOCATION: (297)..(299)
<223> OTHER INFORMATION: Xaa can be any naturally occurring amino acid
<220> FEATURE:
<221> NAME/KEY: misc_feature
<222> LOCATION: (301)..(301)
<223> OTHER INFORMATION: Xaa can be any naturally occurring amino acid
<220> FEATURE:
<221> NAME/KEY: misc_feature
<222> LOCATION: (304)..(304)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (322)..(322)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (342)..(342)
<223> OTHER INFORMATION: Xaa can be any naturally occurring amino acid
<220> FEATURE:
<221> NAME/KEY: misc_feature
<222> LOCATION: (346)..(348)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (354)..(355)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (371)..(371)
<223> OTHER INFORMATION: Xaa can be any naturally occurring amino acid
<220> FEATURE:
<221> NAME/KEY: misc_feature
<222> LOCATION: (377)..(377)
<223> OTHER INFORMATION: Xaa can be any naturally occurring amino acid
<220> FEATURE:
<221> NAME/KEY: misc_feature
<222> LOCATION: (379)..(380)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
```

```
<221> NAME/KEY: misc_feature
<222> LOCATION: (386)..(387)
<223> OTHER INFORMATION: Xaa can be any naturally occurring amino acid
<220> FEATURE:
<221> NAME/KEY: misc_feature
<222> LOCATION: (389)..(389)
<223> OTHER INFORMATION: Xaa can be any naturally occurring amino acid
<220> FEATURE:
<221> NAME/KEY: misc_feature
<222> LOCATION: (391)..(391)
<223> OTHER INFORMATION: Xaa can be any naturally occurring amino acid
<220> FEATURE:
<221> NAME/KEY: misc_feature
<222> LOCATION: (393)..(395)
<223> OTHER INFORMATION: Xaa can be any naturally occurring amino acid
<220> FEATURE:
<221> NAME/KEY: misc_feature
<222> LOCATION: (397)..(397)
<223> OTHER INFORMATION: Xaa can be any naturally occurring amino acid
<220> FEATURE:
<221> NAME/KEY: misc_feature
<222> LOCATION: (403)..(404)
<223> OTHER INFORMATION: Xaa can be any naturally occurring amino acid
<220> FEATURE:
<221> NAME/KEY: misc_feature
<222> LOCATION: (412)..(412)
<223> OTHER INFORMATION: Xaa can be any naturally occurring amino acid
<220> FEATURE:
<221> NAME/KEY: misc_feature
<222> LOCATION: (418)..(418)
<223> OTHER INFORMATION: Xaa can be any naturally occurring amino acid
<220> FEATURE:
<221> NAME/KEY: misc_feature
<222> LOCATION: (420)..(424)
<223> OTHER INFORMATION: Xaa can be any naturally occurring amino acid
<220> FEATURE:
<221> NAME/KEY: misc_feature
<222> LOCATION: (426)..(426)
<223> OTHER INFORMATION: Xaa can be any naturally occurring amino acid
<220> FEATURE:
<221> NAME/KEY: misc_feature
<222> LOCATION: (429)..(429)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (434)..(434)
<223> OTHER INFORMATION: Xaa can be any naturally occurring amino acid
<220> FEATURE:
<221> NAME/KEY: misc_feature
<222> LOCATION: (440)..(441)
<223> OTHER INFORMATION: Xaa can be any naturally occurring amino acid
<220> FEATURE:
<221> NAME/KEY: misc_feature
<222> LOCATION: (444)..(445)
<223> OTHER INFORMATION: Xaa can be any naturally occurring amino acid
<220> FEATURE:
<221> NAME/KEY: misc_feature
<222> LOCATION: (450)..(450)
<223> OTHER INFORMATION: Xaa can be any naturally occurring amino acid
<220> FEATURE:
<221> NAME/KEY: misc_feature
<222> LOCATION: (458)..(458)
<223> OTHER INFORMATION: Xaa can be any naturally occurring amino acid
<220> FEATURE:
<221> NAME/KEY: misc_feature
<222> LOCATION: (464)..(465)
<223> OTHER INFORMATION: Xaa can be any naturally occurring amino acid
<220> FEATURE:
<221> NAME/KEY: misc_feature
<222> LOCATION: (467)..(467)
<223> OTHER INFORMATION: Xaa can be any naturally occurring amino acid
<220> FEATURE:
<221> NAME/KEY: misc_feature
<222> LOCATION: (476)..(476)
<223> OTHER INFORMATION: Xaa can be any naturally occurring amino acid
<220> FEATURE:
```

```
<221> NAME/KEY: misc_feature
<222> LOCATION: (484)..(485)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid
<220> FEATURE:
<221> NAME/KEY: misc_feature
<222> LOCATION: (491)..(492)
<223> OTHER INFORMATION: Xaa can be any naturally occurring amino acid
<220> FEATURE:
<221> NAME/KEY: misc_feature
<222> LOCATION: (497)..(497)
<223> OTHER INFORMATION: Xaa can be any naturally occurring amino acid
<220> FEATURE:
<221> NAME/KEY: misc_feature
<222> LOCATION: (501)..(501)
<223> OTHER INFORMATION: Xaa can be any naturally occurring amino acid
<220> FEATURE:
<221> NAME/KEY: misc_feature
<222> LOCATION: (504)..(504)
<223> OTHER INFORMATION: Xaa can be any naturally occurring amino acid
<220> FEATURE:
<221> NAME/KEY: misc_feature
<222> LOCATION: (506)..(507)
<223> OTHER INFORMATION: Xaa can be any naturally occurring amino acid
<220> FEATURE:
<221> NAME/KEY: misc_feature
<222> LOCATION: (509)..(514)
<223> OTHER INFORMATION: Xaa can be any naturally occurring amino acid
<220> FEATURE:
<221> NAME/KEY: misc_feature
<222> LOCATION: (517)..(518)
<223> OTHER INFORMATION: Xaa can be any naturally occurring amino acid
<220> FEATURE:
<221> NAME/KEY: misc_feature
<222> LOCATION: (520)..(521)
<223> OTHER INFORMATION: Xaa can be any naturally occurring amino acid
<220> FEATURE:
<221> NAME/KEY: misc_feature
<222> LOCATION: (523)..(523)
<223> OTHER INFORMATION: Xaa can be any naturally occurring amino acid
<220> FEATURE:
<221> NAME/KEY: misc_feature
<222> LOCATION: (531)..(532)
<223> OTHER INFORMATION: Xaa can be any naturally occurring amino acid
<220> FEATURE:
<221> NAME/KEY: misc_feature
<222> LOCATION: (534)..(534)
<223> OTHER INFORMATION: Xaa can be any naturally occurring amino acid
<220> FEATURE:
<221> NAME/KEY: MISC_FEATURE
<222> LOCATION: (537)..(540)
<223> OTHER INFORMATION: Xaa is any naturally occurring amino acid or is
      absent

<400> SEQUENCE: 124

Ser Ile Pro Trp Asn Leu Glu Arg Ile Xaa Pro Xaa Xaa Xaa Xaa Xaa
1               5                   10                  15

Xaa Glu Xaa Xaa Xaa Pro Asp Gly Xaa Ser Xaa Val Glu Val Tyr Leu
            20                  25                  30

Leu Asp Thr Ser Ile Gln Xaa Xaa His Arg Glu Ile Glu Gly Arg Val
        35                  40                  45

Xaa Xaa Thr Asp Phe Xaa Xaa Val Pro Glu Glu Asp Gly Thr Arg Phe
    50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Xaa Ser Xaa Xaa
                85                  90                  95

Ser Leu Arg Val Leu Asn Cys Gln Gly Lys Gly Thr Val Ser Gly Thr
            100                 105                 110
```

-continued

```
Leu Ile Gly Leu Glu Phe Ile Arg Lys Ser Gln Leu Xaa Gln Pro Xaa
            115                 120                 125

Gly Pro Leu Val Val Leu Pro Leu Ala Gly Tyr Ser Arg Xaa
130                 135                 140

Leu Asn Xaa Ala Cys Xaa Xaa Leu Ala Arg Xaa Gly Val Val Leu Val
145                 150                 155                 160

Xaa Ala Ala Gly Asn Phe Arg Asp Asp Ala Cys Leu Tyr Ser Pro Ala
                165                 170                 175

Ser Ala Pro Glu Val Ile Thr Val Gly Ala Thr Asn Ala Gln Asp Gln
            180                 185                 190

Pro Val Thr Leu Gly Thr Leu Gly Thr Asn Phe Gly Arg Cys Val Asp
            195                 200                 205

Leu Phe Ala Pro Gly Xaa Asp Ile Ile Gly Ala Ser Ser Asp Cys Ser
210                 215                 220

Thr Cys Xaa Xaa Ser Gln Ser Gly Thr Ser Gln Ala Ala His Val
225                 230                 235                 240

Ala Gly Ile Xaa Ala Met Met Leu Xaa Xaa Pro Xaa Leu Thr Leu
                245                 250                 255

Ala Glu Leu Arg Gln Arg Leu Ile Xaa Phe Ser Xaa Lys Asp Val Ile
            260                 265                 270

Asn Xaa Ala Trp Phe Pro Glu Asp Gln Xaa Val Leu Thr Pro Asn Xaa
            275                 280                 285

Val Ala Xaa Leu Pro Pro Ser Thr Xaa Xaa Gly Xaa Gln Leu Xaa
290                 295                 300

Cys Arg Thr Val Trp Ser Ala His Ser Gly Pro Thr Arg Xaa Ala Thr
305                 310                 315                 320

Ala Xaa Ala Arg Cys Ala Pro Xaa Glu Glu Leu Leu Ser Cys Ser Ser
                325                 330                 335

Phe Ser Arg Ser Gly Xaa Arg Arg Gly Xaa Xaa Xaa Glu Ala Xaa Gly
            340                 345                 350

Gly Xaa Xaa Val Cys Xaa Ala Xaa Asn Ala Phe Gly Gly Glu Gly Val
    355                 360                 365

Tyr Ala Xaa Ala Arg Cys Cys Leu Xaa Pro Xaa Xaa Asn Cys Ser Xaa
370                 375                 380

His Xaa Xaa Pro Xaa Ala Xaa Ala Xaa Xaa Xaa Thr Xaa Val His Cys
385                 390                 395                 400

His Gln Xaa Xaa His Val Leu Thr Gly Cys Ser Xaa His Trp Glu Val
                405                 410                 415

Glu Xaa Leu Xaa Xaa Xaa Xaa Pro Xaa Leu Arg Xaa Arg Xaa Gln
            420                 425                 430

Pro Xaa Gln Cys Val Gly His Xaa Xaa Ala Ser Xaa Xaa Ala Ser Cys
    435                 440                 445

Cys Xaa Ala Pro Gly Leu Glu Cys Lys Xaa Lys Glu His Gly Ile Xaa
450                 455                 460

Xaa Pro Xaa Glu Gln Val Thr Val Ala Cys Glu Xaa Gly Trp Thr Leu
465                 470                 475                 480

Thr Gly Cys Xaa Xaa Leu Pro Gly Xaa Ser Xaa Leu Gly Ala Tyr
                485                 490                 495

Xaa Val Asp Asn Xaa Cys Val Xaa Arg Xaa Xaa Asp Xaa Xaa Xaa Xaa
            500                 505                 510

Xaa Xaa Thr Ser Xaa Xaa Ala Xaa Xaa Ala Xaa Ala Ile Cys Cys Arg
            515                 520                 525

Ser Arg Xaa Xaa Ala Xaa Ala Ser Xaa Xaa Xaa Xaa
530                 535                 540
```

```
<210> SEQ ID NO 125
<211> LENGTH: 66
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (54)..(55)
<223> OTHER INFORMATION: Xaa can be any naturally occurring amino acid

<400> SEQUENCE: 125

Ser Ile Pro Trp Asn Leu Glu Arg Ile Xaa Pro Xaa Xaa Xaa Xaa Xaa
1               5                   10                  15

Xaa Glu Xaa Xaa Xaa Pro Asp Gly Xaa Ser Xaa Val Glu Val Tyr Leu
            20                  25                  30

Leu Asp Thr Ser Ile Gln Xaa Xaa His Arg Glu Ile Glu Gly Arg Val
        35                  40                  45

Xaa Xaa Thr Asp Phe Xaa Xaa Val Pro Glu Glu Asp Gly Thr Arg Phe
    50                  55                  60

His Arg
65

<210> SEQ ID NO 126
<211> LENGTH: 474
<212> TYPE: PRT
<213> ORGANISM: Artificial sequence
<220> FEATURE:
<223> OTHER INFORMATION: Synthetic Construct
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (62)..(62)
```

```
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid
<220> FEATURE:
<221> NAME/KEY: misc_feature
<222> LOCATION: (84)..(85)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (95)..(95)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (161)..(162)
<223> OTHER INFORMATION: Xaa can be any naturally occurring amino acid
<220> FEATURE:
<221> NAME/KEY: misc_feature
<222> LOCATION: (178)..(178)
<223> OTHER INFORMATION: Xaa can be any naturally occurring amino acid
<220> FEATURE:
<221> NAME/KEY: misc_feature
<222> LOCATION: (183)..(185)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (199)..(199)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (208)..(208)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (222)..(222)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (231)..(233)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (252)..(252)
```

-continued

```
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (276)..(276)
<223> OTHER INFORMATION: Xaa can be any naturally occurring amino acid
<220> FEATURE:
<221> NAME/KEY: misc_feature
<222> LOCATION: (280)..(282)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (288)..(289)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (313)..(314)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (320)..(321)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid
<220> FEATURE:
<221> NAME/KEY: misc_feature
<222> LOCATION: (325)..(325)
<223> OTHER INFORMATION: Xaa can be any naturally occurring amino acid
<220> FEATURE:
<221> NAME/KEY: misc_feature
<222> LOCATION: (327)..(329)
<223> OTHER INFORMATION: Xaa can be any naturally occurring amino acid
<220> FEATURE:
<221> NAME/KEY: misc_feature
<222> LOCATION: (331)..(331)
<223> OTHER INFORMATION: Xaa can be any naturally occurring amino acid
<220> FEATURE:
<221> NAME/KEY: misc_feature
<222> LOCATION: (337)..(338)
<223> OTHER INFORMATION: Xaa can be any naturally occurring amino acid
<220> FEATURE:
<221> NAME/KEY: misc_feature
<222> LOCATION: (346)..(346)
<223> OTHER INFORMATION: Xaa can be any naturally occurring amino acid
<220> FEATURE:
<221> NAME/KEY: misc_feature
<222> LOCATION: (352)..(352)
```

-continued

```
<223> OTHER INFORMATION: Xaa can be any naturally occurring amino acid
<220> FEATURE:
<221> NAME/KEY: misc_feature
<222> LOCATION: (354)..(358)
<223> OTHER INFORMATION: Xaa can be any naturally occurring amino acid
<220> FEATURE:
<221> NAME/KEY: misc_feature
<222> LOCATION: (360)..(360)
<223> OTHER INFORMATION: Xaa can be any naturally occurring amino acid
<220> FEATURE:
<221> NAME/KEY: misc_feature
<222> LOCATION: (363)..(363)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (374)..(375)
<223> OTHER INFORMATION: Xaa can be any naturally occurring amino acid
<220> FEATURE:
<221> NAME/KEY: misc_feature
<222> LOCATION: (378)..(379)
<223> OTHER INFORMATION: Xaa can be any naturally occurring amino acid
<220> FEATURE:
<221> NAME/KEY: misc_feature
<222> LOCATION: (384)..(384)
<223> OTHER INFORMATION: Xaa can be any naturally occurring amino acid
<220> FEATURE:
<221> NAME/KEY: misc_feature
<222> LOCATION: (392)..(392)
<223> OTHER INFORMATION: Xaa can be any naturally occurring amino acid
<220> FEATURE:
<221> NAME/KEY: misc_feature
<222> LOCATION: (398)..(399)
<223> OTHER INFORMATION: Xaa can be any naturally occurring amino acid
<220> FEATURE:
<221> NAME/KEY: misc_feature
<222> LOCATION: (401)..(401)
<223> OTHER INFORMATION: Xaa can be any naturally occurring amino acid
<220> FEATURE:
<221> NAME/KEY: misc_feature
<222> LOCATION: (410)..(410)
<223> OTHER INFORMATION: Xaa can be any naturally occurring amino acid
<220> FEATURE:
<221> NAME/KEY: misc_feature
<222> LOCATION: (418)..(419)
<223> OTHER INFORMATION: Xaa can be any naturally occurring amino acid
<220> FEATURE:
<221> NAME/KEY: misc_feature
<222> LOCATION: (423)..(423)
<223> OTHER INFORMATION: Xaa can be any naturally occurring amino acid
<220> FEATURE:
<221> NAME/KEY: misc_feature
<222> LOCATION: (425)..(426)
<223> OTHER INFORMATION: Xaa can be any naturally occurring amino acid
<220> FEATURE:
<221> NAME/KEY: misc_feature
<222> LOCATION: (431)..(431)
<223> OTHER INFORMATION: Xaa can be any naturally occurring amino acid
<220> FEATURE:
<221> NAME/KEY: misc_feature
<222> LOCATION: (435)..(435)
<223> OTHER INFORMATION: Xaa can be any naturally occurring amino acid
<220> FEATURE:
<221> NAME/KEY: misc_feature
<222> LOCATION: (438)..(438)
<223> OTHER INFORMATION: Xaa can be any naturally occurring amino acid
<220> FEATURE:
<221> NAME/KEY: misc_feature
<222> LOCATION: (440)..(441)
<223> OTHER INFORMATION: Xaa can be any naturally occurring amino acid
<220> FEATURE:
<221> NAME/KEY: misc_feature
<222> LOCATION: (443)..(448)
```

```
<223> OTHER INFORMATION: Xaa can be any naturally occurring amino acid
<220> FEATURE:
<221> NAME/KEY: misc_feature
<222> LOCATION: (451)..(452)
<223> OTHER INFORMATION: Xaa can be any naturally occurring amino acid
<220> FEATURE:
<221> NAME/KEY: misc_feature
<222> LOCATION: (454)..(455)
<223> OTHER INFORMATION: Xaa can be any naturally occurring amino acid
<220> FEATURE:
<221> NAME/KEY: misc_feature
<222> LOCATION: (457)..(457)
<223> OTHER INFORMATION: Xaa can be any naturally occurring amino acid
<220> FEATURE:
<221> NAME/KEY: misc_feature
<222> LOCATION: (465)..(466)
<223> OTHER INFORMATION: Xaa can be any naturally occurring amino acid
<220> FEATURE:
<221> NAME/KEY: misc_feature
<222> LOCATION: (468)..(468)
<223> OTHER INFORMATION: Xaa can be any naturally occurring amino acid
<220> FEATURE:
<221> NAME/KEY: MISC_FEATURE
<222> LOCATION: (471)..(474)
<223> OTHER INFORMATION: Xaa is any naturally occurring amino acid or is
      absent

<400> SEQUENCE: 126

Gln Ala Ser Lys Cys Asp Ser His Gly Thr His Leu Ala Gly Val Val
1               5                   10                  15

Ser Gly Arg Asp Ala Gly Val Ala Lys Gly Xaa Ser Xaa Xaa Ser Leu
            20                  25                  30

Arg Val Leu Asn Cys Gln Gly Lys Gly Thr Val Ser Gly Thr Leu Ile
        35                  40                  45

Gly Leu Glu Phe Ile Arg Lys Ser Gln Leu Xaa Gln Pro Xaa Gly Pro
    50                  55                  60

Leu Val Val Leu Leu Pro Leu Ala Gly Gly Tyr Ser Arg Xaa Leu Asn
65                  70                  75                  80

Xaa Ala Cys Xaa Xaa Leu Ala Arg Xaa Gly Val Val Leu Val Xaa Ala
                85                  90                  95

Ala Gly Asn Phe Arg Asp Asp Ala Cys Leu Tyr Ser Pro Ala Ser Ala
            100                 105                 110

Pro Glu Val Ile Thr Val Gly Ala Thr Asn Ala Gln Asp Gln Pro Val
        115                 120                 125

Thr Leu Gly Thr Leu Gly Thr Asn Phe Gly Arg Cys Val Asp Leu Phe
130                 135                 140

Ala Pro Gly Xaa Asp Ile Ile Gly Ala Ser Ser Asp Cys Ser Thr Cys
145                 150                 155                 160

Xaa Xaa Ser Gln Ser Gly Thr Ser Gln Ala Ala Ala His Val Ala Gly
                165                 170                 175

Ile Xaa Ala Met Met Leu Xaa Xaa Xaa Pro Xaa Leu Thr Leu Ala Glu
            180                 185                 190

Leu Arg Gln Arg Leu Ile Xaa Phe Ser Xaa Lys Asp Val Ile Asn Xaa
        195                 200                 205

Ala Trp Phe Pro Glu Asp Gln Xaa Val Leu Thr Pro Asn Xaa Val Ala
    210                 215                 220

Xaa Leu Pro Pro Ser Thr Xaa Xaa Gly Xaa Gln Leu Xaa Cys Arg
225                 230                 235                 240

Thr Val Trp Ser Ala His Ser Gly Pro Thr Arg Xaa Ala Thr Ala Xaa
                245                 250                 255

Ala Arg Cys Ala Pro Xaa Glu Glu Leu Leu Ser Cys Ser Ser Phe Ser
            260                 265                 270
```

-continued

```
Arg Ser Gly Xaa Arg Arg Gly Xaa Xaa Xaa Glu Ala Xaa Gly Gly Xaa
        275                 280                 285

Xaa Val Cys Xaa Ala Xaa Asn Ala Phe Gly Gly Glu Gly Val Tyr Ala
    290                 295                 300

Xaa Ala Arg Cys Cys Leu Xaa Pro Xaa Xaa Asn Cys Ser Xaa His Xaa
305                 310                 315                 320

Xaa Pro Xaa Ala Xaa Ala Xaa Xaa Xaa Thr Xaa Val His Cys His Gln
            325                 330                 335

Xaa Xaa His Val Leu Thr Gly Cys Ser Xaa His Trp Glu Val Glu Xaa
        340                 345                 350

Leu Xaa Xaa Xaa Xaa Pro Xaa Leu Arg Xaa Arg Xaa Gln Pro Xaa
        355                 360                 365

Gln Cys Val Gly His Xaa Xaa Ala Ser Xaa Xaa Ala Ser Cys Cys Xaa
    370                 375                 380

Ala Pro Gly Leu Glu Cys Lys Xaa Lys Glu His Gly Ile Xaa Xaa Pro
385                 390                 395                 400

Xaa Glu Gln Val Thr Val Ala Cys Glu Xaa Gly Trp Thr Leu Thr Gly
                405                 410                 415

Cys Xaa Xaa Leu Pro Gly Xaa Ser Xaa Xaa Leu Gly Ala Tyr Xaa Val
        420                 425                 430

Asp Asn Xaa Cys Val Xaa Arg Xaa Xaa Asp Xaa Xaa Xaa Xaa Xaa
        435                 440                 445

Thr Ser Xaa Xaa Ala Xaa Xaa Ala Xaa Ala Ile Cys Cys Arg Ser Arg
    450                 455                 460

Xaa Xaa Ala Xaa Ala Ser Xaa Xaa Xaa Xaa
465                 470
```